(12) United States Patent
Tanaka et al.

(10) Patent No.: US 6,187,774 B1
(45) Date of Patent: Feb. 13, 2001

(54) FUSED HETEROCYCLIC COMPOUNDS AND PHARMACEUTICAL APPLICATIONS THEREOF

(75) Inventors: Hiroshi Tanaka; Takanobu Kuroita, both of Iruma; Yoshifumi Togo, Osaka; Seigo Ishibuchi; Masakazu Fujio, both of Fukuoka; Takashi Futamura, Iruma, all of (JP)

(73) Assignee: Yoshitomi Pharmaceutical Industries, Ltd., Osaka (JP)

(*) Notice: Under 35 U.S.C. 154(b), the term of this patent shall be extended for 0 days.

(21) Appl. No.: 09/142,203

(22) PCT Filed: Feb. 3, 1997

(86) PCT No.: PCT/JP97/00641

§ 371 Date: Sep. 3, 1998

§ 102(e) Date: Sep. 3, 1998

(87) PCT Pub. No.: WO97/32848

PCT Pub. Date: Sep. 12, 1997

(30) Foreign Application Priority Data

Mar. 4, 1996 (JP) ..................................................... 8-46271

(51) Int. Cl.$^7$ .................. A61K 31/416; A61K 31/4162; C07D 403/06; C07D 401/14; C07D 403/00

(52) U.S. Cl. .............................. 514/253.01; 514/253.04; 514/253.09; 514/253.11; 514/254.06; 544/359; 544/362; 544/366; 544/371; 544/376

(58) Field of Search ................................ 544/359, 362, 544/366, 371, 376; 514/252, 253, 254, 255

(56) References Cited

U.S. PATENT DOCUMENTS

| | | |
|---|---|---|
| 4,307,095 | 12/1981 | Silvestrini et al. ................... 424/250 |
| 4,307,096 | 12/1981 | Silvestrini et al. ................... 424/250 |
| 4,325,952 | 4/1982 | Silvestrini et al. ................... 424/250 |
| 4,831,034 | 5/1989 | Barreau et al. ....................... 514/255 |
| 5,234,927 | 8/1993 | Angeli et al. ......................... 514/253 |

FOREIGN PATENT DOCUMENTS

| | | |
|---|---|---|
| 54-157576 | 12/1979 | (JP) . |
| 63-48267 | 2/1988 | (JP) . |
| 5-194228 | 8/1993 | (JP) . |
| WO94/10145 | 5/1994 | (WO) . |
| WO94/10162 | 5/1994 | (WO) . |
| WO 95/07893 | * 3/1995 | (WO) . |

OTHER PUBLICATIONS

R. Lisciani et al., *Arzneim.–Forsch./Drug Res.*, 32(6), 674–678 (1982).

F. Troxler et al., *Helvetica Chimica Acta*, 51(8), 1870–1881 (1968).

*Derwent Abstracts*, Abstract No. 94–316898/39 (Abstract of WO94/21630).
*Derwent Abstracts*, Abstract No. 94–316894/39 (Abstract of WO94/21626).
*Derwent Abstracts*, Abstract No. 94–316895/39 (Abstract of WO94/21627).
*Derwent Abstracts*, Abstract No. 94–316896/39 (Abstract of WO94/21628).
*Derwent Abstracts*, Abstract No. 94–341726/42 (Abstract of WO94/24105).
*Derwent Abstracts*, Abstract No. 94–302909/37 (Abstract of WO94/20459).
*Derwent Abstracts*, Abstract No. 94–302935/37 (Abstract of WO94/20497).
*Derwent Abstracts*, Abstract No. 94–316885/39 (Abstract of WO94/21615).
*Derwent Abstracts*, Abstract No. 94–333055/41 (Abstract of WO94/22839).
*Derwent Abstracts*, Abstract No. 94–302916/37 (Abstract of WO94/20471).

* cited by examiner

*Primary Examiner*—Bruck Kifle
(74) *Attorney, Agent, or Firm*—Wenderoth, Lind & Ponack, L.L.P.

(57) ABSTRACT

The present invention relates to a fused heterocyclic compound of the formula (I)

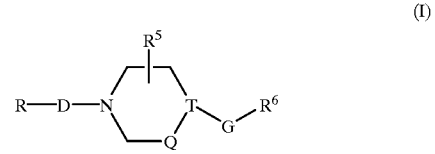

wherein each symbol is as defined in the specification, an optical isomer thereof, a pharmaceutically acceptable salt thereof, a pharmaceutical composition containing a compound of the formula (I), an optical isomer thereof or a pharmaceutically acceptable salt thereof, and a pharmaceutically acceptable additive, and a medicament containing a compound of the formula (I), an optical isomer thereof or a pharmaceutically acceptable salt thereof. The compound of the present invention is a useful antipsychotic agent effective not only for positive symptoms centering on hallucination and delusion characteristic of the acute stage of schizophrenia, but also negative symptoms of apathy, abulia and autism. The inventive compound is expected to make a highly safe antipsychotic agent associated with less side effects, such as extrapyramidal symptoms and endocrine disturbance, which are observed when a conventional antipsychotic agent having a $D_2$ receptor blocking action is administered. Therefore, the inventive compound can be used as a therapeutic agent for the diseases such as schizophrenia.

9 Claims, No Drawings

FUSED HETEROCYCLIC COMPOUNDS AND PHARMACEUTICAL APPLICATIONS THEREOF

TECHNICAL FIELD

The present invention relates to a novel fused heterocyclic compound having affinity for dopamine $D_4$ (hereinafter to be referred to as $D_4$, the same abbreviation to be employed with regard to the following dopamine receptor subtypes) receptor and serotonin 2 (hereinafter to be referred to as 5-$HT_2$) receptor, which blocks NMDA receptor hypofunction, and which is used in the medical field as a central nervous agent, particularly as an antipsychotic agent.

BACKGROUND ART

The following patent applications have been published with regard to central nervous agents having affinity for $D_4$ receptor. WO94/10162, WO94/21630 and WO94/21626 disclose heterotricyclic aromatic compounds having affinity for $D_4$ receptor; WO94/21627, WO94/21628 and WO94/24105 disclose indole derivatives having affinity for $D_4$receptor; WO94/20459 and WO94/20497 disclose pyrropyridine derivatives having affinity for $D_4$ receptor; and WO94/21615 and WO94/22839 disclose benzimidazol derivatives having affinity for $D_4$ receptor. WO94/10145 and WO94/20471 disclose pyrazole derivatives and quinolone derivatives each having affinity for $D_4$ receptor.

Japanese Patent Unexamined Publication No. 157576/1979 discloses that cydoalkyltriazoles represented by dapiprazole [3-(2-(4-(2-tolyl)-1-piperazinyl)ethyl)-5,6,7,8-tetrahydro-s-triazole-[4,3-a]pyridine] can be used for the therapy of glaucoma, psychosis and the like.

Almost all antipsychotic agents applicable to schizophrenia show a common pharmacological action of blocking the receptor of dopamine which is one of the cerebral neurotransmitters, and exhibit particularly potent $D_2$ receptor blocking action. These medicaments (typical antipsychotic agents) are effective against positive symptoms centering on hallucination and delusion characteristic of the acute stage of schizophrenia, but are barely effective against negative symptoms of apathy, abulia and autism. In addition, they are associated with serious problems of side effects such as extrapyramidal symptoms (e.g., delayed dyskinesia, acute dystonia, akathisia, etc.) and endocrine disturbance (e.g., hyperprolactinemia) observed upon acute administration and long term consecutive administration.

Dopamine receptor has been conventionally classified into two receptor subtypes by pharmacological methods according to the type of ligand binding and association mode with adenylate cyclase [Nature, vol. 227, p. 93 (1979)]. That is, a $D_1$ receptor type that promotes adenylate cyclase via acceleratory G protein to produce cyclic AMP, and a $D_2$ receptor type that suppresses adenylate cyclase via suppressive G protein to suppress production of cyclic AMP. Due to the revolutionary development of molecular biology in recent years, five different genes of dopamine receptors were cloned and the dopamine receptors are now classified into $D_1$ and $D_5$ receptors belonging to the $D_1$ fans, and $D_2$, $D_3$ and $D_4$ receptors belonging to the $D_2$ family [Trends in Pharmacol. Sci., vol. 15, p. 264 (1994)].

It has been documented that haloperidol, which is a typical antipsychotic agent, has higher affinity for $D_2$ receptor than for $D_4$ receptor, and clozapine, which is associated with less extrapyramidal side effects and also effective against negative symptoms, has 10 times higher affinity for $D_4$ receptor than for $D_2$ receptor [Nature, vol. 350, p. 610 (1991)], [Trends in Pharmacol. Sci., vol. 15, p. 264 (1994)]. It has been also reported that the effective therapeutic plasma concentration of clozapine correlates with the affinity constant for $D_4$ receptor [Trends in Pharmacol. Sci., vol. 15, p. 264 (1994)]. A report has been documented on a binding test using the postmortem brain of a schizophrenic patient, that $D_4$ receptor showed 6 times greater level than in a healthy subject [Nature, vol. 365, p. 441 (1993)]. Therefrom it appears that $D_4$ receptor highly likely causes schizophrenia or is present at the action site of a therapeutic agent. There have been found variations in the distribution of dopamine receptor in the brain due to subtypes, wherein $D_2$ receptor is most frequently found in the corpus striatum, and $D_4$ receptor is most often found in the frontal lobe of cerebral cortex which is responsible for the emotional functions.

From clinical applications, it has been made clear that the concurrent use of ritanserin (which is a 5-$HT_2$ receptor blocker) with a typical antipsychotic agent improves negative symptoms and emotional disorders such as anxiety [Current Therapeutics Research, vol. 10, p. 492 (1986)]. Of the side effects caused by antipsychotic agents, malignant syndromes that are most serious and deadly, though low in incidence is, according to one hypothetical view, caused by the imbalance of dopamine/serotonin nervous functions in the body temperature control center [Japanese Journal of Psychopharmacology, vol. 11, p. 17 (1989)], and suppression of the onset of the disease by the application of the 5-$HT_2$ receptor blocking action is expected.

There is also a hypothetical view on the cause of schizophrenia, that says that the degradation of the function of the NMDA (N-methyl-D-aspartic acid) nervous system that is projected from the cerebral cortex to subcortex impairs the suppressive feed-back function of the information control circuit, which in turn aggravates the schizophrenia state, like the excessive promotion of the activity of the subcortical dopamine nervous system, and clozapine has been reported to show blockage of NMDA receptor hypofunction besides the action on dopamine and serotonin nervous systems [Trends Neurosci., vol. 13, p. 272 (1990)].

From the foregoing, a compound having a $D_4$ receptor and 5-$HT_2$ receptor blocking action, and which blocks NMDA receptor hypofunction, is expected to make an antipsychotic agent associated with less extrapyramidal side effects and effective against both positive and negative symptoms. It is therefore an object of the present invention to provide a compound exhibiting strong blocking action on $D_4$ receptor and 5-$HT_2$ receptor, as well as blockage of NMDA receptor hypofunction, which is effective against both negative symptoms and positive symptoms as compared to conventional compounds and which is associated with less side effects.

DISCLOSURE OF THE INVENTION

The present inventors have conducted intensive studies and found that a novel fused heterocyclic compound of the following formula (I), an optical isomer thereof and a pharmaceutically acceptable salt thereof have stronger blocking action on $D_4$ receptor and 5-$HT_2$ receptor than on $D_2$ receptor, and that they show blockage of NMDA receptor hypofunction. The present inventors have further found that these compounds can make useful antipsychotic agents effective against not only positive symptoms centering on hallucination and delusion characteristic of the acute stage of schizophrenia, but also negative symptoms of apathy, abulia and autism, that cause less side effects such as extrapyramidal symptoms and endocrine disturbance observed when conventional antipsychotic agents having $D_2$ receptor blocking action are administered, which resulted in the completion of the present invention.

Accordingly, the present invention relates to a fused heterocyclic compound of the formula (I)

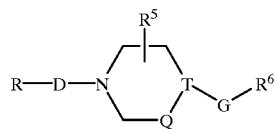

(I)

wherein

R is a group selected from the group consisting of the groups having the following formulas (1), (2), (3), (4), (5), (6), (7), (8) and (9)

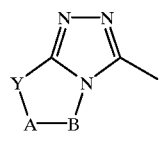

(1)

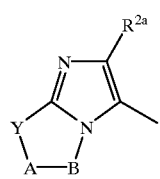

(2)

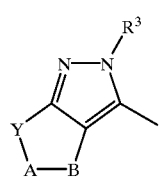

(3)

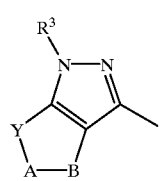

(4)

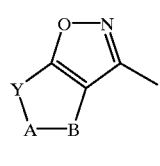

(5)

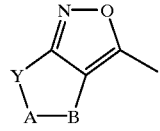

(6)

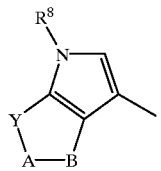

(7)

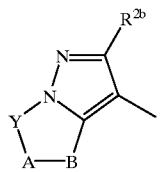

(8)

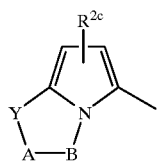

(9)

wherein

Y is a linear or branched $C_1$–$C_4$ alkylene optionally having a substituent $R^{1a}$ at an optional position, wherein $R^{1a}$ is hydrogen, alkyl, hydroxy, alkoxy, amino or alkylamino, A is void, or an oxygen atom, a sulfur atom, SO, $SO_2$ or N—$R^7$ wherein $R^7$ is hydrogen, alkyl, arylalkyl or acyl, B is a linear or branched $C_1$–$C_4$ alkylene optionally having a substituent $R^{1b}$ at an optional position, wherein $R^{1b}$ is hydrogen, alkyl, hydroxy, alkoxy, amino or alkylamino, $R^{2a}$, $R^{2b}$ and $R^{2c}$ are the same or different and each is a hydrogen or an alkyl, $R^3$ is a hydrogen, an alkyl, an acyl or an aryl, and $R^8$ is a hydrogen, an acyl or an alkyl;

D is void, or a linear or branched alkylene having 1 to 8 carbon atoms;

Q—T is a bond of CH, $CH_2$—N, $(CH_2)_2$—N, $CH_2$—C($R^4$) wherein $R^4$ is hydrogen, hydroxy, alkyl or alkoxy, or CH=C, provided that when R is a group of the formula (1) and A is void, the bond Q—T is CH, $(CH_2)_2$—N, $CH_2$—C($R^4$) wherein $R^4$ is as defined above, or CH=C;

G is void, or a linear or branched alkylene having 1 to 8 carbon atoms or a carbonyl;

$R^5$ is a hydrogen or an alkyl; and $R^6$ is an optionally substituted aryl, an optionally substituted heteroaryl or an optionally substituted fused heteroaryl, an optical isomer thereof or a pharmaceutically acceptable salt thereof.

The present invention also provides a pharmaceutical composition comprising a fused heterocyclic compound of the formula (I), an optical isomer thereof or a pharmaceutically acceptable salt thereof, and a pharmaceutically acceptable carrier, and a medicament comprising a fused heterocyclic compound of the formula (I), an optical isomer thereof or a pharmaceutically acceptable salt thereof.

The fused heterocyclic compound of the formula (I) includes the following 9 kinds of compounds.

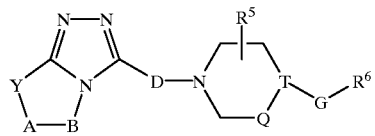
(I-1)

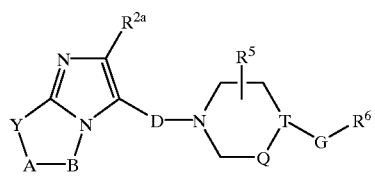
(I-2)

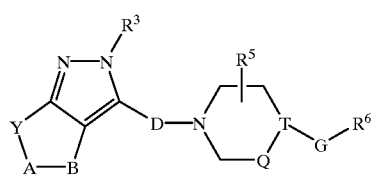
(I-3)

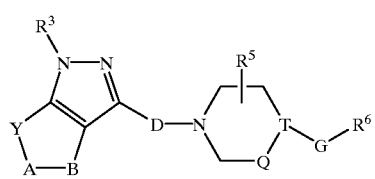
(I-4)

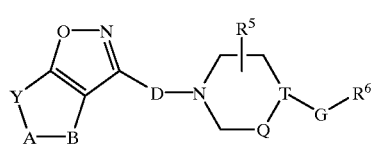
(I-5)

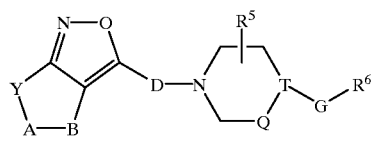
(I-6)

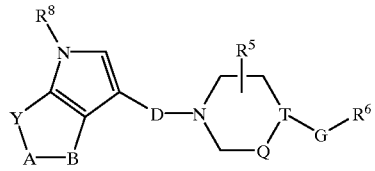
(I-7)

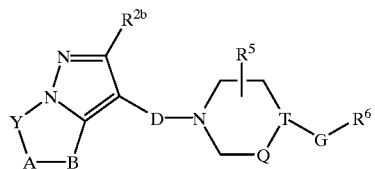
(I-8)

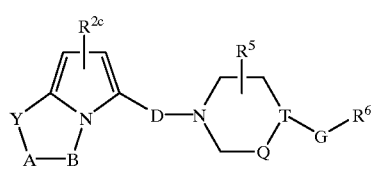
(I-9)

With regard to the above formula (I), alkyl at $R^{1a}$ is, for example, methyl, ethyl, propyl, isopropyl, butyl, isobutyl, tert-butyl, pentyl, hexyl, heptyl, octyl, decyl, hexadecyl, octadecyl and the like, with preference given to alkyl having 1 to 4 carbon atoms. The alkoxy is, for example, methoxy, ethoxy, propoxy, isopropoxy, butoxy, isobutoxy, tert-butoxy, pentyloxy, hexyloxy, heptyloxy, octyloxy and the like, with preference given to alkoxy having 1 to 4 carbon atoms. The alkylamino is, for example, methylamino, dimethylamino, ethylamino, diethylamino, propylamino, dipropylamino and the like.

The alkyl, alkoxy and alkylamino at $R^{1b}$ are exemplified by those mentioned with respect to alkyl, alkoxy and alkylamino at $R^{1a}$.

The alkyl at $R^{2a}$, $R^{2b}$ and $R^{2c}$ is exemplified by those mentioned with respect to alkyl at $R^{1a}$.

The alkyl at $R^3$ is exemplified by those mentioned with respect to alkyl at $R^{1a}$. The acyl is, for example, formyl, acetyl, propionyl, benzoyl, benzylcarbonyl and the like, with preference given to acetyl. The aryl is, for example, phenyl, naphthyl, 2-indanyl and the like, with preference given to phenyl having 1 or 2 substituent(s), such as halogen, methyl, trifluoromethyl and methoxy.

The alkyl and alkoxy at $R^4$ are exemplified by those mentioned with respect to alkyl and alkoxy at $R^{1a}$.

The alkyl at $R^5$ is exemplified by those mentioned with respect to alkyl at $R^{1a}$.

The alkyl at $R^6$ is, for example, phenyl, naphthyl, 2-indanyl and the like. The heteroaryl is, for example, pyridyl, furyl, thienyl, pyrimidinyl and the like. The fused heteroaryl is, for example, 1,2-benzoisoxazol-3-yl, 1,2-benzoisothiazol-3-yl, indol-3-yl, benzo[b]furan-3-yl, benzo[b]thiophen-3-yl and the like. The substituent therefor may be, for example, halogen (e.g., fluorine, chlorine and bromine), haloalkyl (e.g., trifluoromethyl), alkyl (e.g., methyl, ethyl, propyl, isopropyl, butyl, isobutyl and tert-butyl), alkoxy (e.g., methoxy, ethoxy, propoxy, isopropoxy, butoxy, isobutoxy, tert-butoxy, pentyloxy, hexyloxy, heptyloxy and octyloxy), hydroxy, nitro, amino, methylamino, dimethylamino and the like.

The alkyl at $R^7$ is exemplified by those mentioned with respect to alkyl at $R^{1a}$. The arylalkyl is, for example, benzyl, 2-phenylethyl, 3-phenylpropyl, 2-methyl-2-phenylethyl, 3-methyl-3-phenylpropyl, 4-chlorobenzyl, 2-(4-chlorophenyl)ethyl, 3-(4-chlorophenyl)propyl, 2-methyl-2-(4-chlorophenyl)ethyl, 3-methyl-3-(4-chlorophenyl)propyl and the like, with preference given to benzyl. The acyl is, for example, formyl, acetyl, propionyl, benzoyl, benzylcarbonyl and the like, with preference given to acetyl.

The alkyl at $R^8$ is exemplified by those mentioned with respect to alkyl at $R^{1a}$. The acyl is exemplified by those mentioned with respect to acyl at $R^3$.

The linear or branched alkylene having 1 to 4 carbon atoms at Y is exemplified by methylene, ethylene, trimethylene, tetramethylene, methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene and the like, with preference given to ethylene and trimethylene.

The linear or branched alkylene having 1 to 4 carbon atoms at B is exemplified by those mentioned with respect to the linear or branched alkylene having 1 to 4 carbon atoms at Y.

The linear or branched alkylene having 1 to 8 carbon atoms at D is exemplified by methylene, ethylene, trimethylene, tetramethylene, pentamethylene, hexamethylene, octamethylene, methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene and the like, with preference given to ethylene, trimethylene and tetramethylene.

The linear or branched alkylene having 1 to 8 carbon atoms at G is exemplified by those mentioned with respect to the linear or branched alkylene having 1 to 8 carbon atoms at D.

The group of the formula

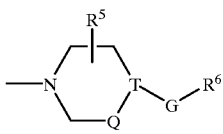

is specifically exemplified by the following groups.

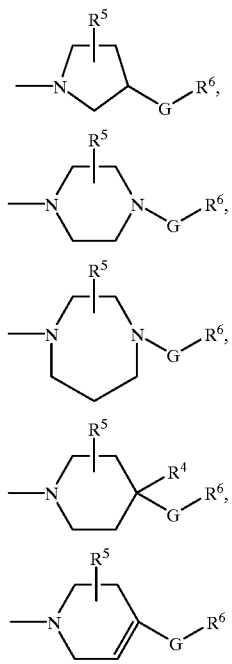

With regard to the formula (I), a preferable compound is the compound
wherein
R is a group selected from the group consisting of the groups having the formulas (1), (2), (3), (4), (5), (6), (7), (8) and (9),
wherein
Y is a linear or branched $C_1$–$C_4$ alkylene optionally having a substituent $R^{1a}$ at an optional position wherein $R^{1a}$ is hydrogen or alkyl,
A is void, or an oxygen atom, a sulfur atom or N—$R^7$ wherein $R^7$ is hydrogen, alkyl, arylalkyl or acyl,
B is a linear or branched $C_1$–$C_4$ alkylene optionally having a substituent
$R^{1b}$ at an optional position, wherein $R^{1b}$ is hydrogen or alkyl,
$R^{2a}$, $R^{2b}$ and $R^{2c}$ are the same or different and each is a hydrogen or an alkyl,
$R^3$ is a hydrogen, an alkyl, an acyl or an aryl, and
$R^8$ is a hydrogen, an acyl or an alkyl;
D is void, or a linear or branched alkylene having 1 to 8 carbon atoms;
Q—T is a bond of CH, $CH_2$—N, $(CH_2)_2$—N, $CH_2$—C($R^4$) wherein $R^4$ is hydrogen, hydroxy, alkyl or alkoxy, or CH=C,
provided that when R is a group of the formula (1) and A is void, the bond Q—T is CH, $(CH_2)_2$—N, $CH_2$—C($R^4$) wherein $R^4$ is as defined above, or CH=C;
G is void;
$R^5$ is a hydrogen or an alkyl; and
$R^6$ is an optionally substituted aryl, an optionally substituted heteroaryl or an optionally substituted fused heteroaryl.

With regard to the formula (I), a more preferable compound is the compound
wherein
R is a group selected from the group consisting of the groups having the formulas (1), (2), (3), (4), (5), (6), (7), (8) and (9),
wherein
Y is a linear alkylene having 1 to 4 carbon atoms,
A is void, or an oxygen atom or N—$R^7$ wherein $R^7$ is hydrogen or acyl,
B is a linear or branched alkylene having 1 to 4 carbon atoms,
$R^{2a}$, $R^{2b}$ and $R^{2c}$ are the same or different and each is a hydrogen or an alkyl having 1 to 4 carbon atoms,
$R^3$ is a hydrogen, an alkyl having 1 to 4 carbon atoms or an acyl, and
$R^8$ is a hydrogen or an alkyl having 1 to 4 carbon atoms;
D is void, or a linear or branched alkylene having 1 to 8 carbon atoms;
Q—T is a bond of $CH_2$—N, $CH_2$—C($R^4$) wherein $R^4$ is hydrogen, hydroxy, alkyl or alkoxy, or CH=C,
provided that when R is a group of the formula (1) and A is void, the bond Q—T is $CH_2$—C($R^4$) wherein $R^4$ is as defined above, or CH=C;
G is void;
$R^5$ is a hydrogen or an alkyl having 1 to 4 carbon atoms; and
$R^6$ is an optionally substituted aryl, an optionally substituted heteroaryl or an optionally substituted fused heteroaryl.

With regard to the formula (I), a still more preferable compound is the compound
wherein
R is a group selected from the group consisting of the groups having the formulas (1), (2), (3), (4), (6), (7) and (8),
wherein
Y is an ethylene,
A is void, or an oxygen atom or N—$R^7$ wherein $R^7$ is hydrogen or acyl,
B is a linear or branched alkylene having 1 to 3 carbon atoms,
$R^{2a}$ and $R^{2b}$ are the same or different and each is a hydrogen or an alkyl having 1 to 4 carbon atoms, $R^3$ is a hydrogen or an alkyl having 1 to 4 carbon atoms, and $R^8$ is a hydrogen or an alkyl having 1 to 4 carbon atoms;

D is void, or a linear or branched alkylene having 1 to 8 carbon atoms;

Q—T is a bond of $CH_2$—N, $CH_2$—$C(R^4)$ wherein $R^4$ is hydrogen, alkyl or alkoxy, or CH=C,
provided that when R is a group of the formula (1) and A is void, the bond Q—T is $CH_2$—$C(R^4)$ wherein $R^4$ is as defined above, or CH=C;

G is void;

$R^5$ is a hydrogen or an alkyl having 1 to 4 carbon atoms; and $R^6$ is an optionally substituted aryl, an optionally substituted heteroaryl or an optionally substituted fused heteroaryl.

With regard to the formula (I), a particularly preferable compound is the compound
wherein R is a group selected from the group consisting of the groups having the formulas (1), (2), (3), (4), (6), (7) and (8),
wherein
Y is an ethylene,
A is void, or an oxygen atom or N—$R^7$ wherein $R^7$ is hydrogen or acyl,
B is a linear alkylene having 1 to 3 carbon atoms,
$R^{2a}$ and $R^{2b}$ are the same or different and each is a hydrogen or a methyl,
$R^3$ is a hydrogen or a methyl, and
$R^8$ is a hydrogen or a methyl;

D is a trimethylene;

Q—T is a bond of $CH_2$—N, $CH_2$—CH or CH=C,
provided that when R is a group of the formula (1) and A is void, the bond Q—T is $CH_2$—CH or CH=C;

G is void;

$R^5$ is a hydrogen; and $R^6$ is an aryl optionally having halogen or alkyl having 1 to 4 carbon atoms.

With regard to the formula (I), the most preferable compounds are those selected from the following group of compounds wherein the number in the parenthesis corresponds to example number.

(2) 3-(3-(4-(4-chlorophenyl)-1,2,3,6-tetrahydropyridin-1-yl)propyl)6,7,8,9-tetrahydro-5H-1,2,4-triazolo[4,3-a]azepine, (3) 3-(3-(4-(4-chlorophenyl)piperidin-1-yl)propyl)-6,7,8,9-tetrahydro-5H-1,2,4-triazolo[4,3-a]azepine,

(48) 3-(3-(4-(4-chlorophenyl)piperazin-1-yl)propyl)-5,6,7,8-tetrahydro-4H-cyclohepta[c]isoxazole,

(89) 3-(3-(4-(4-chlorophenyl)piperidin-1-yl)propyl)-5,6,7,8-tetrahydro-4H-cyclohepta[c]isoxazole,

(90) 3-(3-(4-(4-chlorophenyl)-1,2,3,6-tetrahydropyridin-1-yl)propyl)-5,6,7,8-tetrahydro-4H-cyclohepta[c]isoxazoe, (104) 3-(3-(4-(4-chlorophenyl)piperazin-1-yl)propyl)-4,5,6,7-tetrahydro-2H-indazole, (113) 3-(3-(4-(4-fluorophenyl)piperazin-1-yl)propyl)-5,6,7,8-tetrahydroimidazo[1,2-a]pyridine, (116) 3-(3-(4-(4-fluorophenyl)piperazin-1-yl)propyl)-4,5,6,7-tetrahydro-2H-indazole, (117) 3-(3-(4-(4-methylphenyl)piperin-1-yl)propyl)-4,5,6,7-tetrahydro-2H-indazole, (118) 3-(3-(4-phenylpiperazin-1-yl)propyl)4,5,6,7-tetrahydro-2H-indazole, (137) 3-(3-(4-(4-fluorophenyl)piperazin-1-yl)propyl)-2,4,6,7-tetrahydropyrano[4,3-c]pyrazole, (141) 3-(3-(4-(4-fluorophenyl)piperazin-1-yl)propyl)-4,5,6,7-tetrahydro-2H-pyrazolo[4,3-c]pyridine, (142) 5-acetyl-3-(3-(4-(4-fluorophenyl)piperazin-1-yl)propyl)-4,5,6,7-tetrahydro-2H-pyrazolo[4,3-c]pyridine, (153) 3-(3-(4-(4-chlorophenyl)piperazin-1-yl)propyl)-4,5,6,7-tetrahydro-1-methyl-1H-indazole, (154) 3-(3-(4-(4-fluorophenyl)piperazin-1-yl)propyl)-4,5,6,7-tetrahydro-1-methyl-1H-indazole, (155) 4,5,6,7-tetrahydro-1-methyl-3-(3-(4-(4-methylphenyl)piperazin-1-yl)propyl)-1H-indazole, (156) 4,5,6,7-tetrahydro-1-methyl-3-(3-(4-phenylpiperazin-1-yl)propyl)-1H-indazole, (162) 3-(3-(4-(4-fluorophenyl)piperazin-1-yl)propyl)-4,5,6,7-tetrahydroindole and (173) 3-(3-(4-(4-fluorophenyl)piperazin-1-yl)propyl)-4,5,6,7-tetrahydropyrazolo-[2,3-a]pyridine.

The pharmaceutically acceptable salt of the compound of the formula (I) is, for example, acid addition salt with inorganic acid (e.g., hydrochloric acid, hydrobromic acid, sulfuric acid, phosphoric acid and nitric acid) or organic acid (e.g., acetic acid, propionic add, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid and ascorbic acid).

The compound of the formula (I) and pharmaceutically acceptable salts thereof may exist in the form of a hydrate or a solvate, and such hydrate and solvate are also encompassed in the present invention. Examples thereof include 1/10 hydrate, 1/4 hydrate, 1/2 hydrate, monohydrate, dihydrochloride 1/2 hydrate, dihydrochloride dihydrate, dihydrochloride 3/2 hydrate and the like. When the compound of the formula (I) has an asymmetric carbon, at least two kinds of optical isomers exist. These optical isomers and racemates thereof are encompassed in the present invention.

The compound of the formula (I) and the inventive compounds included in the formula (I) can be synthesized by the following methods. Each symbol in the following reaction formulas is as defined above unless specifically indicated.

1. Compound wherein R is a group of the formula (1):

Method (1)

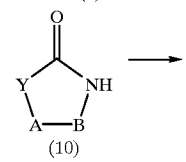

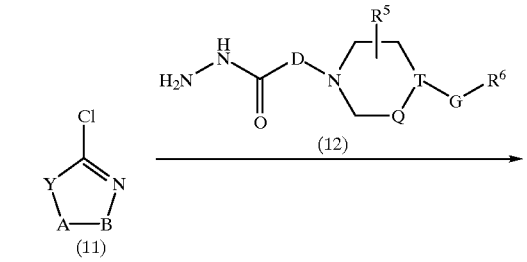

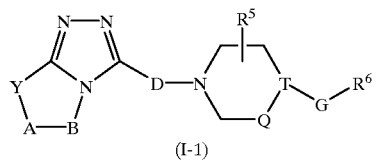

A compound of the formula (10) is reacted with chlorinating agent (e.g., phosphorus pentachloride, phosphorus trichloride and phosphorus oxychloride) in a suitable solvent (e.g., benzene, toluene, xylene and mixed solvents of optional members therefrom) at room temperature to the refluxing temperature of the solvent for 1–24 hours to give the compound of the formula (11). This compound is reacted in a suitable solvent (e.g., methanol, ethanol, butanol, ethylene glycol, N-methyl-2-pyrrolidone, 1,3-dimethyl-2-imidazolidinone and mixed solvents of optional members therefrom) in the presence of a compound of the formula (12) at room temperature to 200° C. for 1–24 hours to give the compound of the formula (I-1).

Method (2)

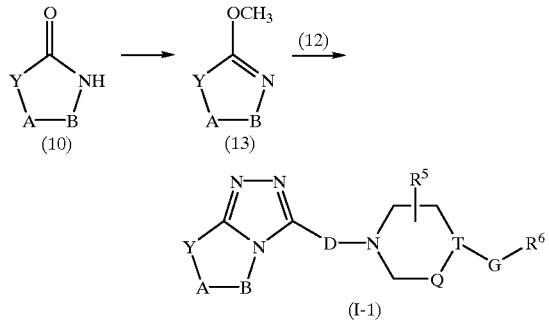

A compound of the formula (10) is reacted with dimethyl sulfate in a suitable solvent (e.g., benzene, toluene, xylene and mixed solvents of optional members therefrom) at the refluxing temperature of the solvent for 1–24 hours to give the compound of the formula (13). This compound is reacted in a suitable solvent (e.g., methanol, ethanol, butanol, ethylene glycol, N-methyl-2-pyrrolidone, 1,3dimethyl-2-imidazolidinone and mixed solvents of optional members therefrom) in the presence of a compound of the formula (12) at room temperature to 200° C. for 1–24 hours to give the compound of the formula (I-1).

Method (3)

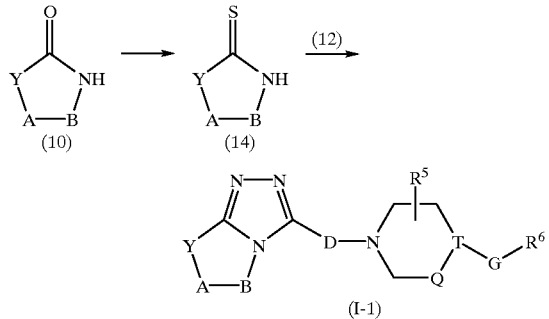

A compound of the formula (10) is reacted with thionating agent (e.g., phosphorus pentasulfate and Lawesson reagent [2,4-bis(4-methoxyphenyl)-1,3-dithia-2,4-diphosphetane-2, 4-disulfide]) in a suitable solvent (e.g., benzene, toluene, xylene and mixed solvents of optional members therefrom) at room temperature to the refluxing temperature of the solvent for 1–24 hours to give the compound of the formula (14). This compound is reacted in a suitable solvent (e.g., methanol, ethanol, butanol, ethylene glycol, N-methyl-2-pyrrolidone, 1,3-dimethyl-2-pyrrolidone, 1,3-dimethyl-2-imidazolidinone and mixed solvents of optional members therefrom) in the presence of a compound of the formula (12) at room temperature to 200° C. for 1–24 hours to give the compound of the formula (I-1).

Method (4)

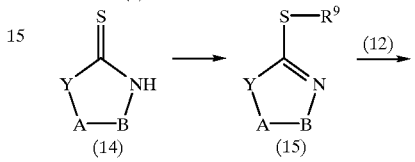

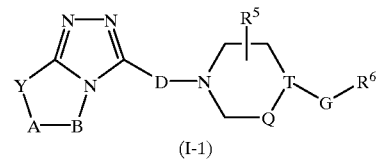

A compound of the formula (14) is reacted with benzyl chloride, p-nitrobenzyl chloride or methyl iodide in a suitable solvent that does not interfere with the reaction (e.g., tetrahydrofuran, diethyl ether, dioxane, water and mixed solvents of optional members therefrom) in the presence of a base such as potassium hydroxide and potassium tert-butoxide, at room temperature to the refluxing temperature of the solvent for 1–24 hours to give the compound of the formula (15) wherein $R^9$ is methyl, benzyl, p-nitrobenzyl and the like and other symbols are as defined above. This compound is reacted with a compound of the formula (12) in a suitable solvent (e.g., methanol, ethanol, butanol, ethylene glycol, N-methyl-2-pyrrolidone, 1,3-dimethyl-2-imidazolidinone and mixed solvents of optional members therefrom) at room temperature to 200° C. for 1–24 hours to give the compound of the formula (I-1).

Method (5)

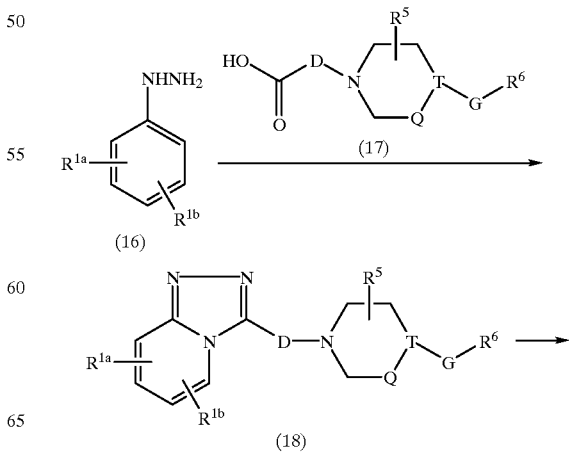

-continued

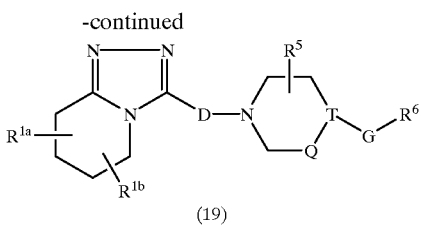

(19)

A compound of the formula (16) and a compound of the formula (17) are stirred while heating at 150° C.–200° C. for 1–24 hours to give a compound of the formula (18). This compound is subjected to catalytic hydrogenation using a platinum, palladium or nickel catalyst in a suitable solvent that does not interfere with the reaction (e.g., methylene chloride, chloroform, ethyl acetate, methanol, ethanol and mixed solvents of optional members therefrom) to give the compound of the formula (19).

Method (6)

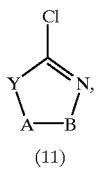

(11)

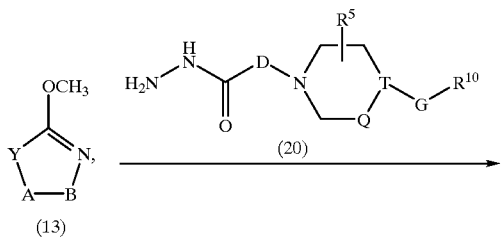

(13) (20)

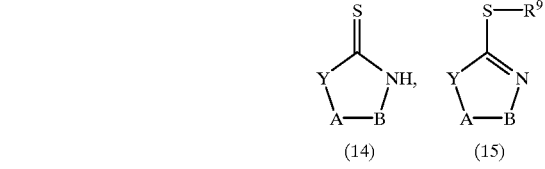

(14) (15)

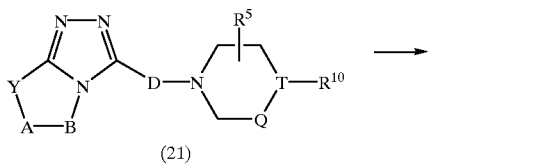

(21)

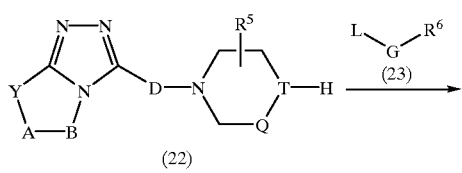

(22) (23)

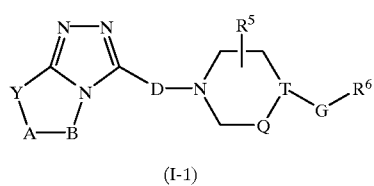

(I-1)

Any one of the compounds of the formulas (11), (13), (14) and (15) is reacted with a compound of the formula (20) wherein $R^{10}$ is a protecting group inert to the reaction, such as tert-butoxycarbonyl and benzyloxycarbonyl, and Q—T is $(CH_2)_2$—N, in a suitable solvent that does not interfere with the reaction (e.g., methanol, ethanol, butanol, ethylene glycol, N-methyl-2-pyrrolidone, 1,3-dimethyl-2-imidazolidinone and mixed solvents of optional members therefrom) at room temperature to 200° C. for 1–24 hours to give a compound of the formula (21) wherein Q—T is $(CH_2)_2$—N and $R^{10}$ is as defined above. This compound is subjected to deprotection by a conventional method using a suitable acid such as hydrochloric acid, hydrobromic acid and trifluoroacetic acid to give a compound of the formula (22) wherein Q—T is $(CH_2)_2$—N and $R^{10}$ is as defined above. This compound or an acid addition salt thereof, such as hydrochloride, hydrobromide, sulfate and oxalate, is reacted with a compound of the formula (23) wherein L is chlorine, bromine, iodine, methanesulfonyloxy, p-toluenesulfonyloxy, trifluoromethanesulfonyloxy and the like, in a suitable solvent that does not interfere with the reaction (e.g., tetrahydrofuran, dichloromethane, dimethylformamide and mixed solvents of optional members therefrom) in the presence of a base such as potassium carbonate, sodium hydroxide, triethylamine, pyridine and dimethylaminopyridine, from under ice-cooling to room temperature for 1–24 hours to give a compound of the formula (I-1) wherein Q—T is $(CH_2)_2$—N.

Method (7)

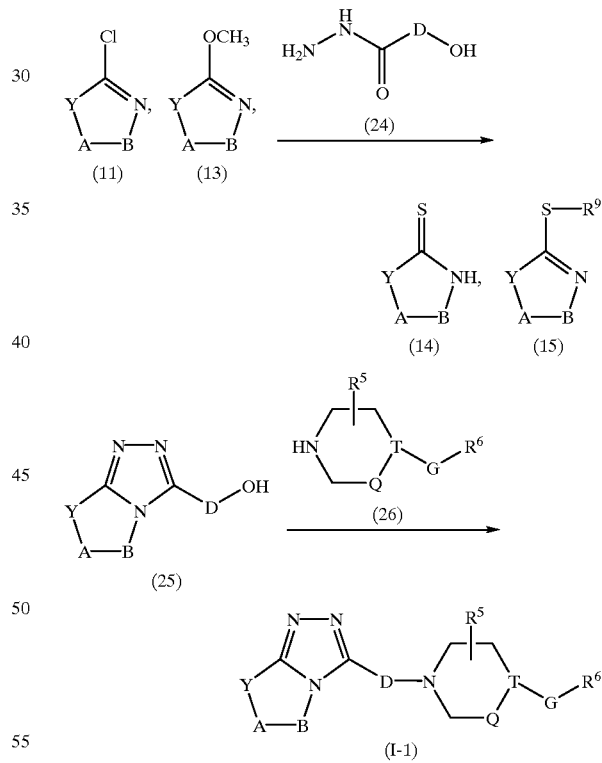

Any one of the compounds of the formulas (11), (13), (14) and (15) is reacted with a compound of the formula (24) in a suitable solvent that does not interfere with the reaction (e.g., methanol, ethanol, butanol, ethylene glycol, N-methyl-2-pyrrolidone, 1,3-dimethyl-2-imidazolidinone and mixed solvents of optional members therefrom) at room temperature to 200° C. for 1–24 hours to give a compound of the formula (25). This compound is reacted with p-toluenesulfonyl chloride or methanesulfonyl chloride in a suitable solvent that does not interfere with the reaction (e.g., methylene chloride, chloroform and dichloroethane) in the presence of a base such as triethylamine to introduce a leaving group. The resulting compound is reacted with a compound of the formula (26) or an acid addition salt thereof, such as hydrochloride, hydrobromide, sulfate and oxalate, in a suitable solvent that does not interfere with the reaction (e.g., methylene chloride, chloroform, dichloroethane, tetrahydrofuran, diethyl ether and mixed solvents of optional members therefrom) in the presence of a suitable base such as potassium carbonate, pyridine and triethylamine, at room temperature to the refluxing temperature of the solvent for 1–24 hours to give a compound of the formula (I-1).

2. Compound wherein R is a group of the formula (2):

Method (1)

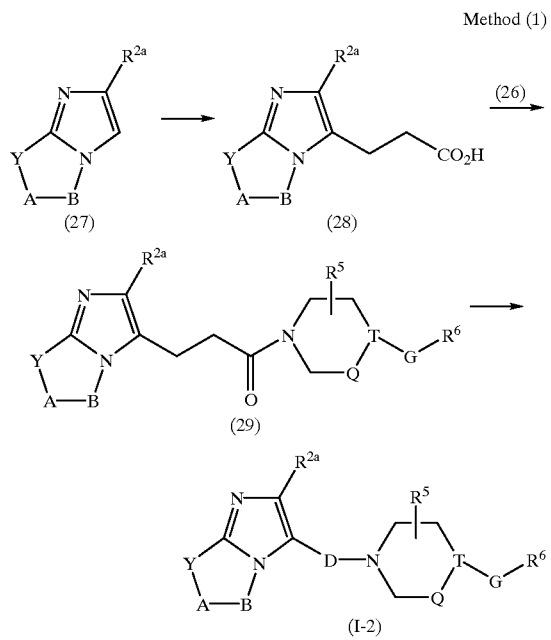

Method (2)

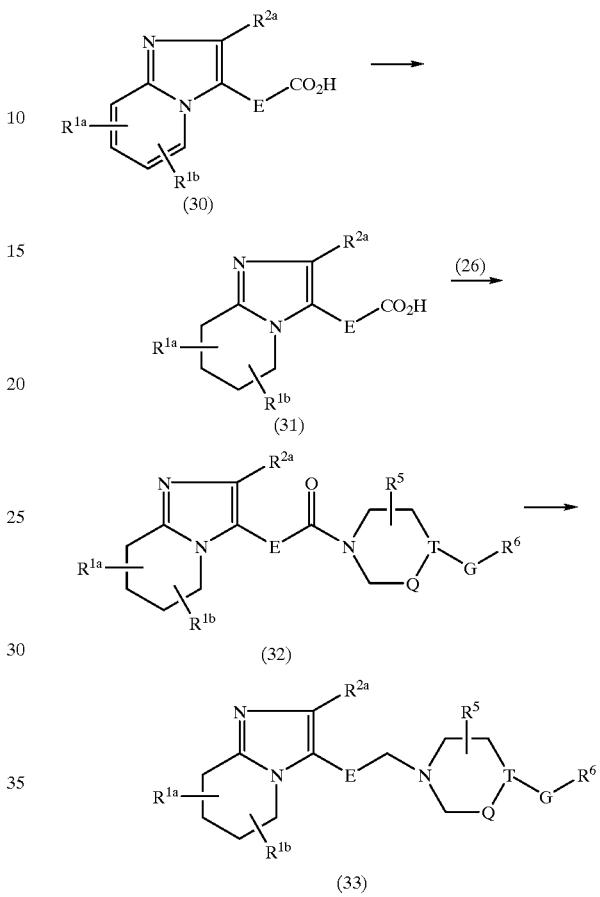

Using a compound of the formula (27) obtained by the method described in Eur. J. Med. Chem., vol. 10, p. 528 (1975) and in accordance with the method described in Japanese Patent Unexamined Publication No. 189179/1983, a compound of the formula (28) is obtained. This compound is reacted with a compound of the formula (26) using a fusing agent such as 1,3-dicyclohexylcarbodiimide, 1-ethyl-3-(3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (29). When a reactive derivative (acid chloride and acylimidazol) of the compound of the formula (28) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

The compound of the formula (29) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (I-2) wherein D is trimethylene.

A compound of the formula (30) wherein E is a liner or branched alkylene having 1 to 7 carbon atoms, which is obtained by the method described in J. Med. Chem., vol. 12, p. 122 (1969) is subjected to catalytic hydrogenation using a platinum, palladium or nickel catalyst in a suitable solvent that does not interfere with the reaction (e.g., methylene chloride, chloroform, ethyl acetate, methanol, ethanol and mixed solvents of optional members therefrom) to give the compound of the formula (31). This compound is reacted with a compound of the formula (26) using a fusing agent such as 1,3-dicyclohexylcarbodiimide, 1-ethyl-3-(3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (32). When a reactive derivative (acid chloride and acylimidazol) of the compound of the formula (31) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

The compound of the formula (32) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (33).

Method (3)

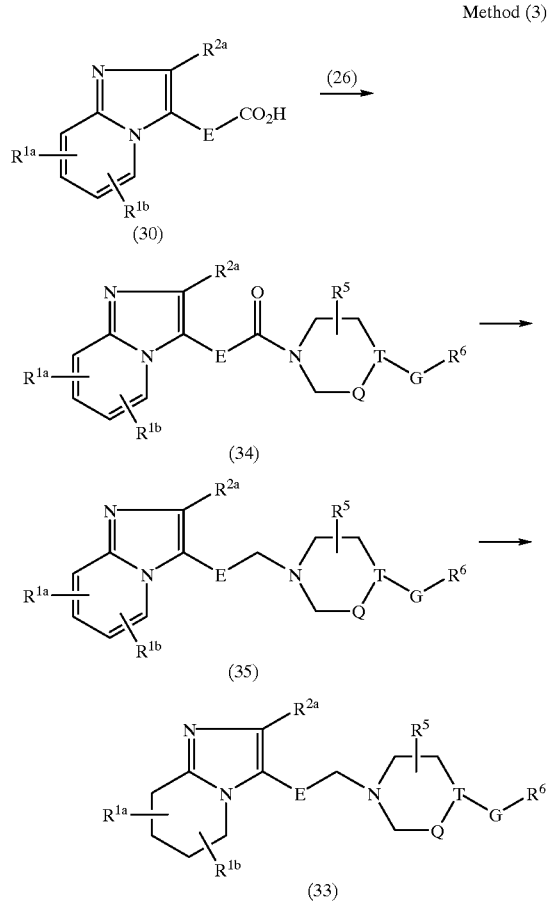

A compound of the formula (30) wherein E is a linear or branched alkylene having 1 to 7 carbon atoms) is reacted with a compound of the formula (26) using a fusing agent such as 1,3-dicyclohexylcarbodiimide, 1-ethyl-3-(3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (34). When a reactive derivative (acid chloride and acylimidazol) of the compound of the formula (30) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

The compound of the formula (34) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (35). This compound is subjected to catalytic hydrogenation using a platinum, palladium or nickel catalyst in a suitable solvent that does not interfere with the reaction (e.g., methylene chloride, chloroform, ethyl acetate, methanol, ethanol and mixed solvents of optional members therefrom) to give the compound of the formula (33).

3. Compound wherein R is a group of the formula (3) or (4):

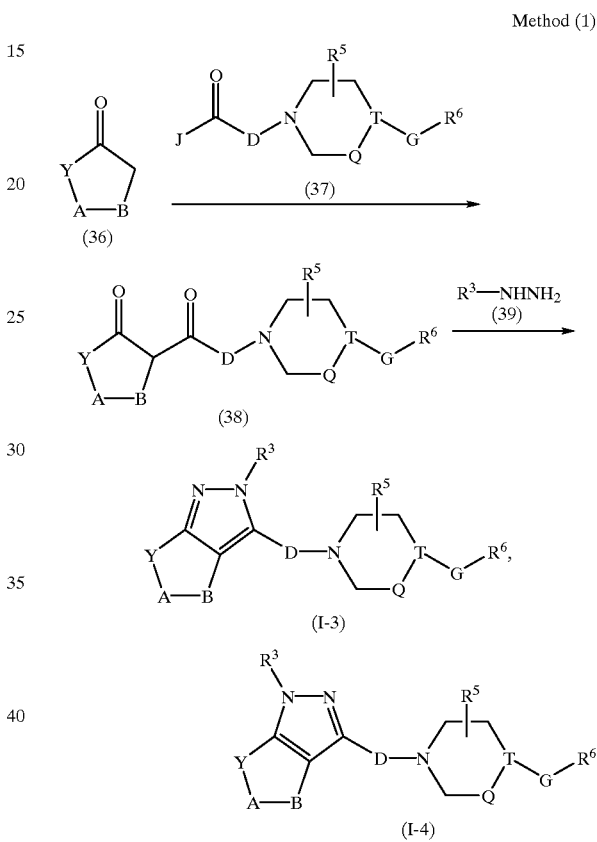

A compound of the formula (36) is reacted with a compound of the formula (37) wherein J is chlorine, imidazole, cyano and the like in a suitable solvent that does not interfere with the reaction (e.g., tetrahydrofuran, diethyl ether, methylene chloride, chloroform, dimethylformamide and mixed solvents of optional members therefrom) in the presence of a suitable dehydrogenating agent (e.g., lithium diisopropylamide, lithium bistrimethylsilylamide, potassium t-butoxide and triethylamine) from −78° C. to under ice-cooling for 1–24 hours to give a compound of the formula (38). This compound is reacted in a suitable solvent (e.g., methanol, ethanol, butanol, ethylene glycol, methylene chloride, chloroform and mixed solvents of optional members therefrom) in the presence of a compound of the formula (39) at room temperature to the refluxing temperature of the solvent for 1–24 hours to give a compound of the formula (I-3) or the formula (I-4).

Method (2)

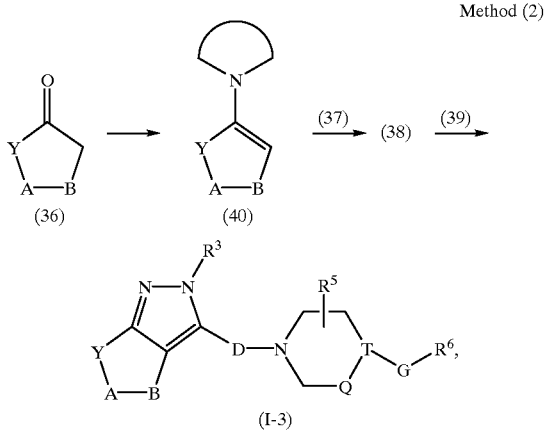

formula (40) can be obtained from a compound of the formula (36) and secondary amine (e.g., morphoine, pyrrolidine and piperidine). According to the method described in Synthesis, p. 510 (1970), a compound of the formula (38) can be obtained from this compound and a compound of the formula (37). This compound is reacted in a suitable solvent (e.g., methanol, ethanol, butanol, ethylene glycol, methylene chloride, chloroform and mixed solvents of optional members therefrom) in the presence of a compound of the formula (39) at room temperature to the refluxing temperature of the solvent for 1–24 hours to give a compound of the formula (I-3) or the formula (I-4).

Method (3)

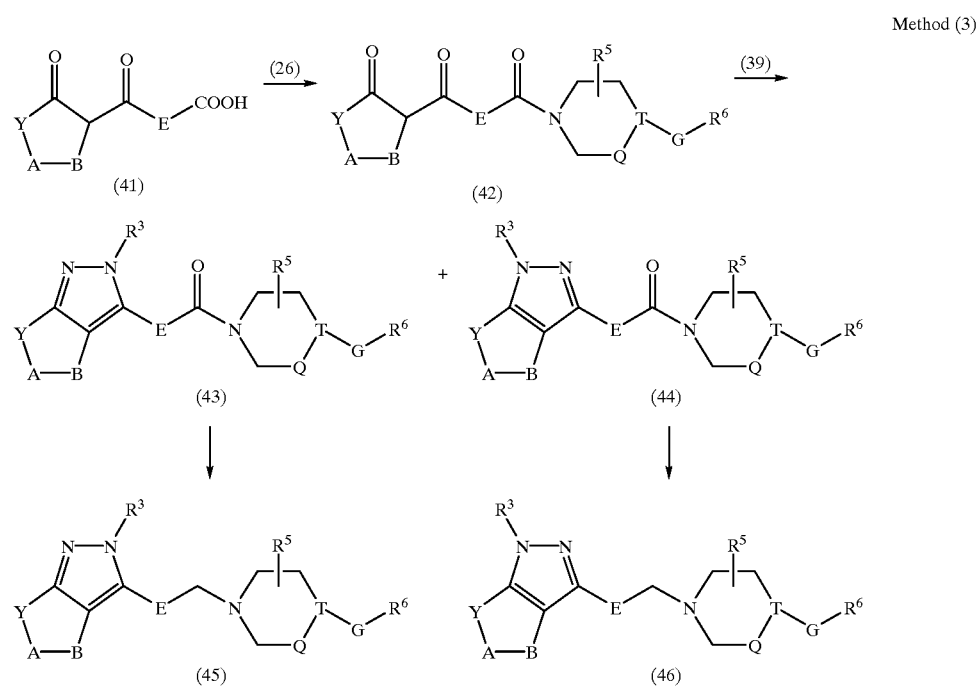

According to the method described in Org. Syntheses. Coll., Vol. 5, p. 808 (1973), an examine compound of the A compound of the formula (41) obtained by the method described in Chemische Berichte, vol. 92, p. 652 (1959) is reacted with a compound of the formula (26) using a fusing agent such as 1,3-dicyclohexylcarbodiimide, 1-ethyl-3-(3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (42). When a reactive derivative (acid chloride and acylimidazol) of the compound of the formula (41) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

-continued

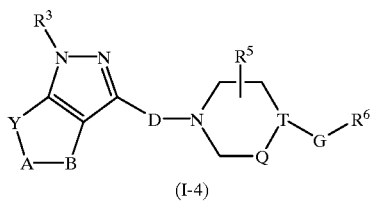

This compound is reacted in a suitable solvent (e.g., methanol, ethanol, butanol, ethylene glycol, methylene chloride, chloroform and mixed solvents of optional members therefrom) in the presence of a compound of the formula (39) at room temperature to the refluxing temperature of the solvent for 1–24 hours to give a compound of the formula (43) or (44) or a mixture thereof. In the case of a mixture, it can be separated by a purification method such as silica gel column chromatography and recrystallization. The compound of the formula (43) or (44) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (45) or (46).

mixture, it can be separated by a purification method such as silica gel column chromatography and recrystallization. When a reactive derivative (acid chloride and acylimidazol) of the compound of the formula (47) or (48) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

The compound of the formula (43) or (44) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (45) or (46).

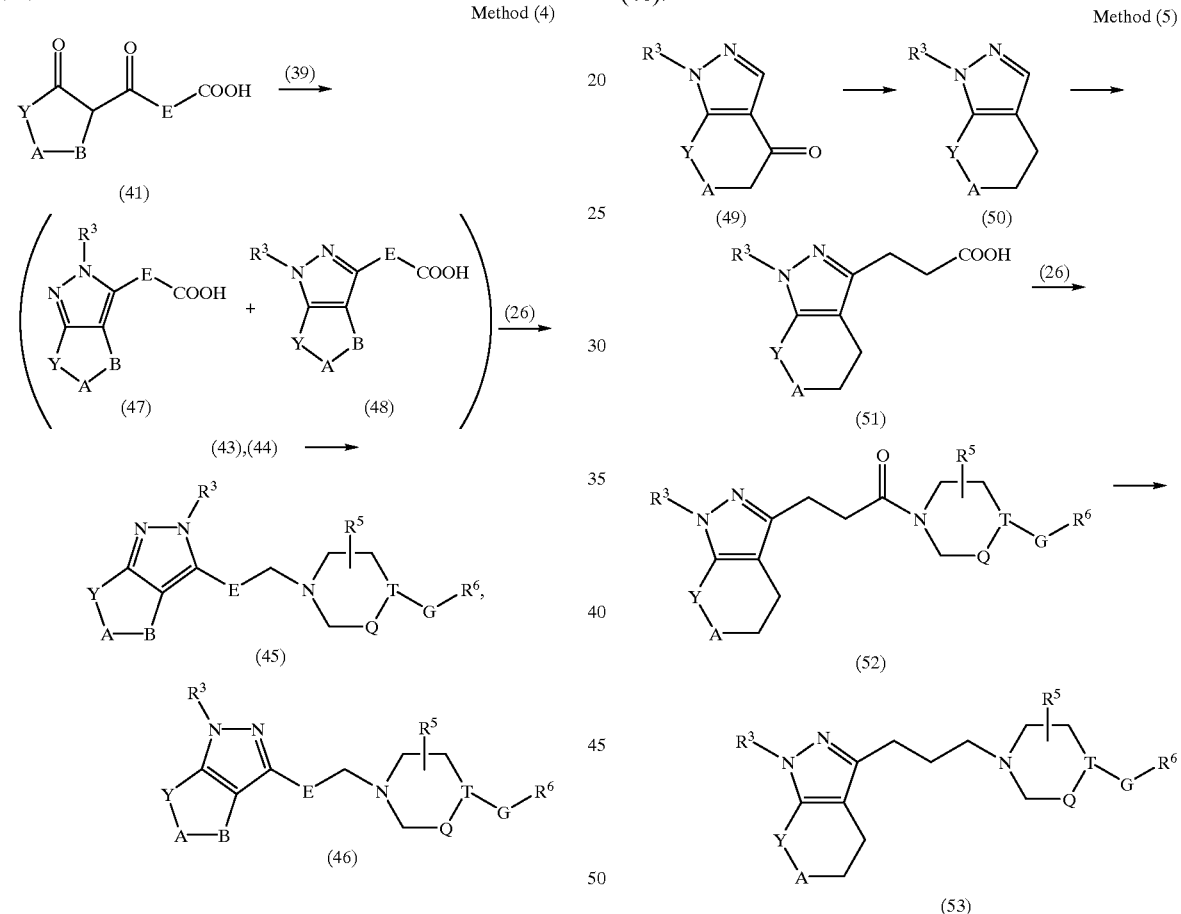

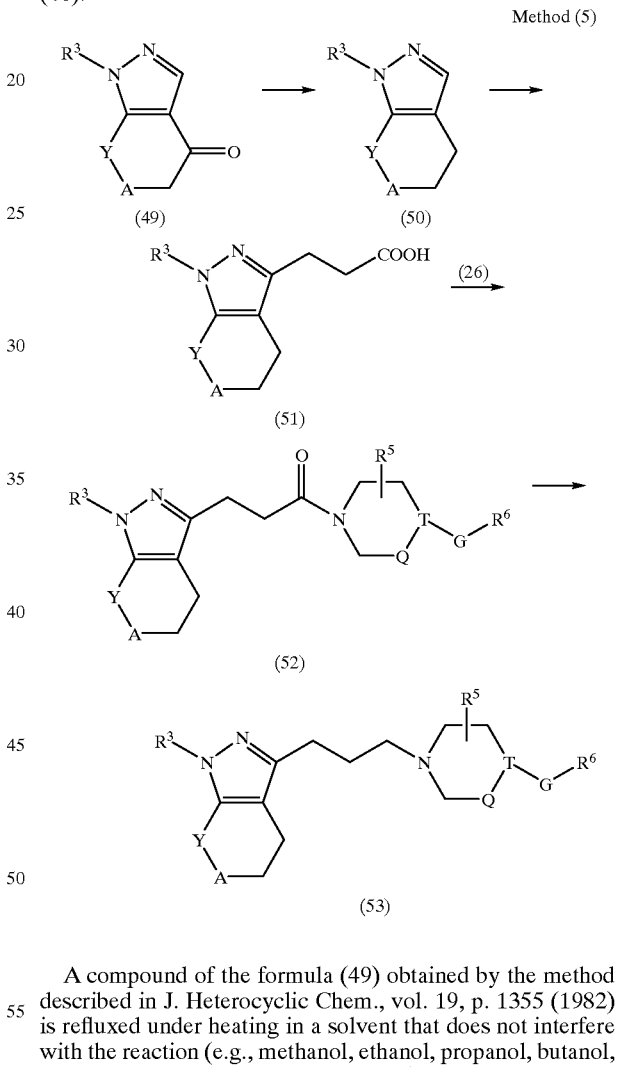

A compound of the formula (41) is reacted in a suitable solvent (e.g., methanol, ethanol, butanol, ethylene glycol, methylene chloride, chloroform and mixed solvents of optional members therefrom) in the presence of a compound of the formula (39) at room temperature to the refluxing temperature of the solvent for 1–24 hours to give a compound of the formula (47) or (48) or a mixture thereof. This compound is reacted with a compound of the formula (26) using a fusing agent such as 1,3-dicyclohexylcarbodiimide, 1-ethyl-3-( 3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (43) or(44) or a mixture thereof. In the case of a A compound of the formula (49) obtained by the method described in J. Heterocyclic Chem., vol. 19, p. 1355 (1982) is refluxed under heating in a solvent that does not interfere with the reaction (e.g., methanol, ethanol, propanol, butanol, ethylene glycol and dithylene glycol) in the presence of hydrazine and a base (e.g., sodium hydroxide and potassium hydroxide) for 1–24 hours to give a compound of the formula (50). This reaction can be also carried out by clemmensen reaction or thioketal method to give a compound of the formula (50). This compound is treated according to the method described in Japanese Patent Unexamined Publication No. 189179/1983 to give a compound of the formula (51). This compound is reacted with a compound of the formula (26) using a fusing agent such as 1,3dicyclohexylcarbodiimide, 1-ethyl-3-(3- dimethylaminopropyl)carbodiimide and cyanophosphonic acid diester in a suitable solvent that does not interfere with the reaction (e.g., tetrahydrofuran, dichloromethane, diethylformamide and mixed solvents of optional members therefrom) in the presence of a tertiary amine such as triethylamine from under ice-cooling to room temperature for 1–24 hours to give a compound of the formula (52). When a reactive derivative (acid chloride and acylimidazol) of the compound of the formula (51) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyrridine from under ice-cooling to room temperature for 1–24 hours.

The compound of the formula (52) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (53).

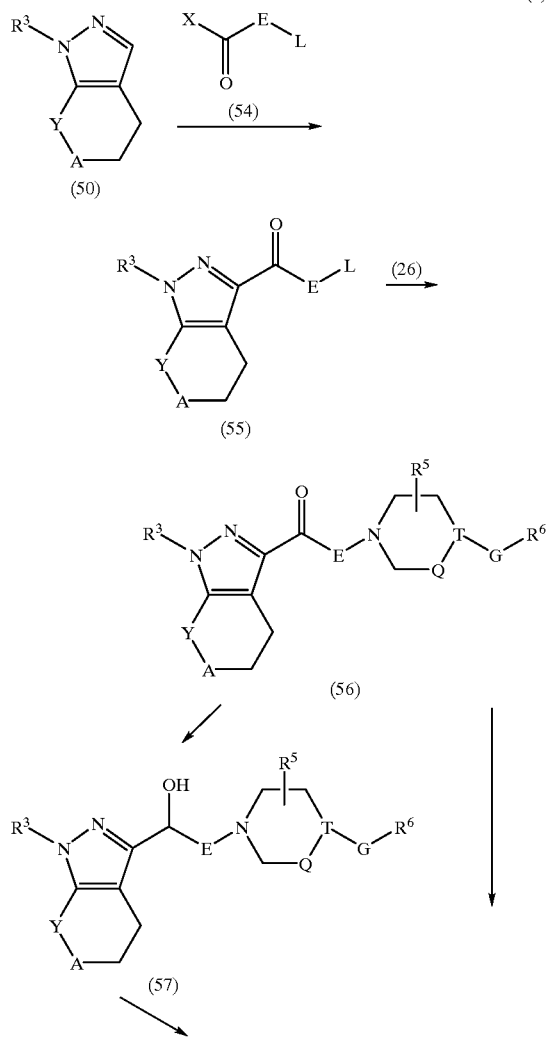

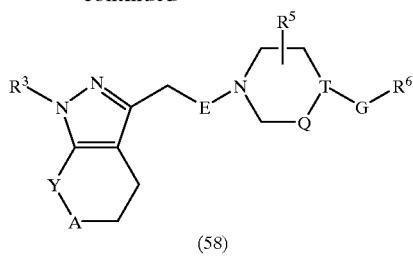

A compound of the formula (50) is reacted with a compound of the formula (54), wherein X is chlorine or bromine and other symbols are as defined above, in a solvent that does not interfere with the reaction (e.g., methylene chloride, chloroform, methylene dichloride and nitrobenzene) in the presence of a Lewis acid (e.g., aluminum chloride, iron(III) chloride, tin chloride and boron trifluoride) at −78° C. to the refluxing temperature of the solvent for 1–24 hours to give a compound of the formula (55). This compound is reacted with a compound of the formula (26) or an acid addition salt thereof (e.g., hydrochloride, hydrobromide, sulfate and oxalate) in a suitable solvent that does not interfere with the reaction (e.g., tetrahydrofuran, dichloromethane, dimethylformamide and mixed solvents of optional members therefrom) in the presence of a suitable base (e.g., potassium carbonate, pyridine and triethylamine) at room temperature to the reflowing temperature of the solvent for 1–24 hours to give a compound of the formula (56). This compound is reacted with a suitable reducing agent (e.g., sodium borohydride, borane and lithium aluminum hydride) in a solvent that does not interfere with the reaction (e.g., methanol, ethanol, propanol, methylene chloride, chloroform, methylene dichloride and mixed solvents of optional members therefrom) to give a compound of the formula (57).

This compound is treated according to the method described in Bull. Chem. Soc. Jpn., vol. 62, p. 3537 (1989) to give a compound of the formula (58). A compound of the formula (56) is refluxed under heating in a solvent that does not interfere with the reaction (e.g., methanol, ethanol, propanol, butanol, ethylene glycol and diethylene glycol) in the presence of hydrazine and a base (e.g., sodium hydroxide and potassium hydroxide) for 1–24 hours to give a compound of the formula (58). This reaction can be also carried out by clemmensen reaction or thioketal method to give a compound of the formula (58).

4. Compound wherein R is a group of the formula (5) or (6):

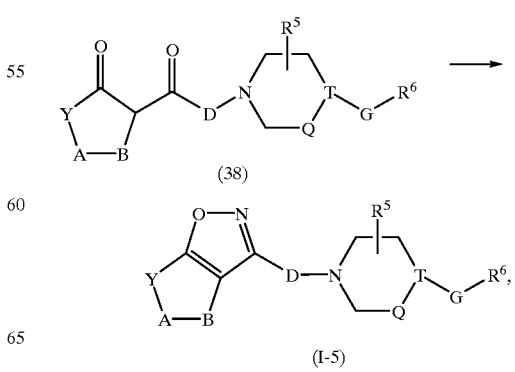

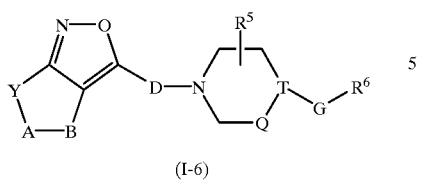

(I-6)

A compound of the formula (38) is reacted in a suitable solvent (e.g., methanol, ethanol, butanol, ethylene glycol, methylene chloride, chloroform and mixed solvents of optional members therefrom) in the presence of hydroxylamine hydrochloride at room temperature to the refluxing temperature of the solvent for 1–24 hours to give a compound of the formula (I-5) or the formula (I-6).

of the solvent for 1–24 hours to give a compound of the formula (61) or (62).

Method (3)

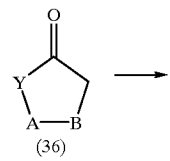

(36)

Method (2)

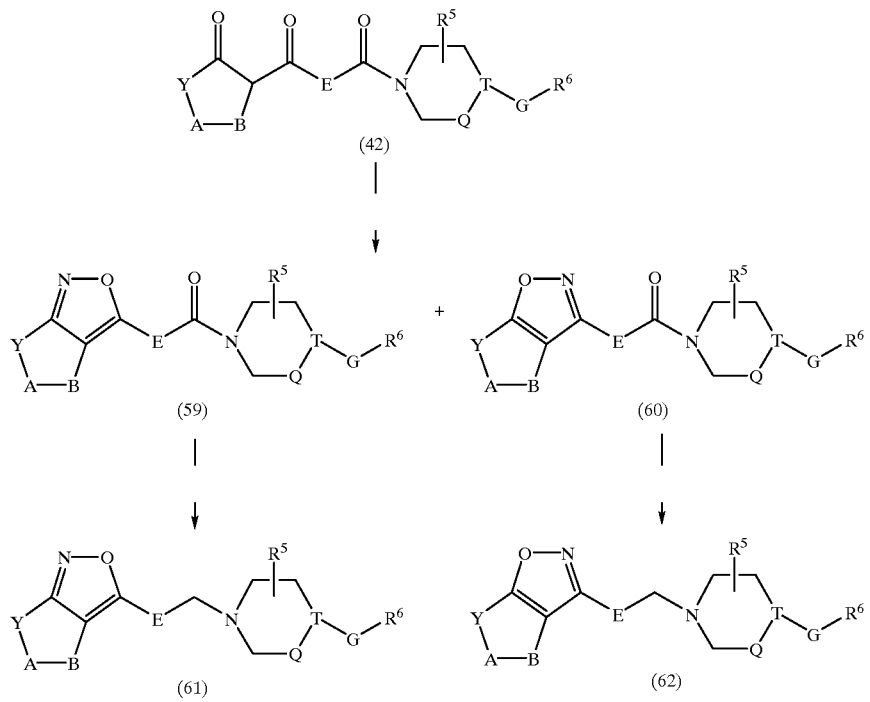

This compound of the formula (42) is reacted in a suitable solvent (e.g., methanol, ethanol, butanol, ethylene glycol, methylene chloride, chloroform and mixed solvents of optional members therefrom) in the presence of hydroxylamine hydrochloride at room temperature, to the refluxing temperature of the solvent for 1–24 hours to give a compound of the formula (59) or (60) or a mixture thereof. In the case of a mixture, it can be separated by a purification method such as silica gel column chromatography and recrystallization. The compound of the formula (59) or (60) thus obtained is reduced in a suitable solvent that does not interfere with the reaction (e.g., tetrahydrofuran, diethyl ether, toluene and mixed solvents of optional members therefrom) using a reducing agent such as aluminum lithium hydride and borane at −78° C. to the refluxing temperature -continued

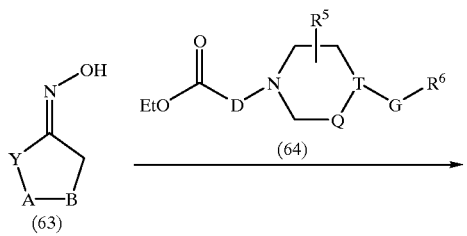

-continued

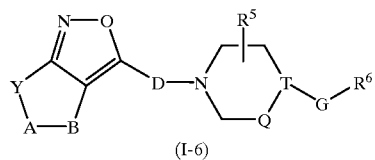
(I-6)

A compound of the formula (36) is reacted with hydroxylamine hydrochloride under acidic or neutral conditions in a suitable solvent that does not interfere with the reaction (e.g., methanol, ethanol, butanol, ethylene glycol and mixed solvents of optional members therefrom) to give a compound of the formula (63). This compound is reacted with a compound of the formula (64) in a suitable solvent that does not interfere with the reaction (e.g., tetrahydrofuran, diethyl ether and mixed solvents of optional members therefrom) in the presence of a suitable dehydrogenating agent (e.g., sodium hydride and n-butyl lithium) from under ice-cooing to room temperature for 1–24 hours to give a compound of the formula (I-6).

5. Compound wherein R is a group of the formula (7):

Method (1)

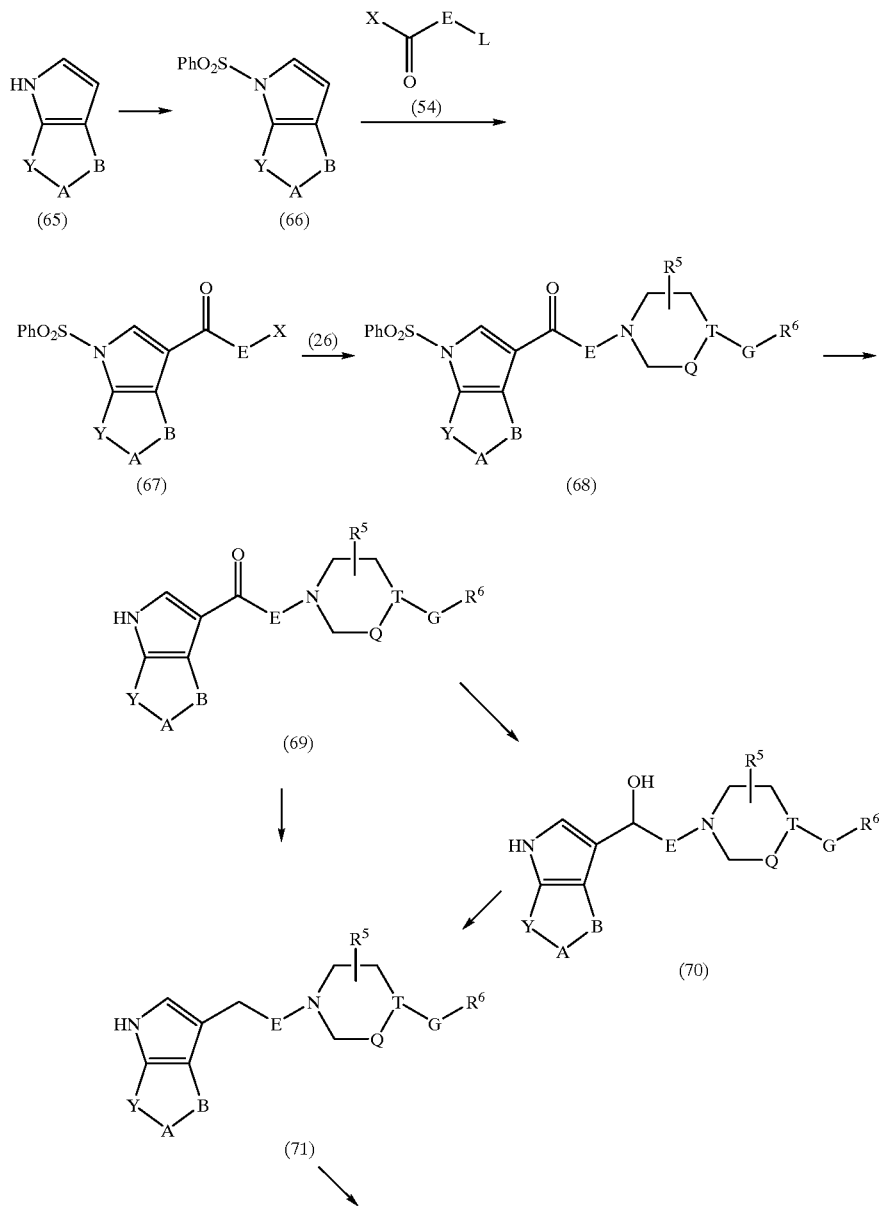

-continued

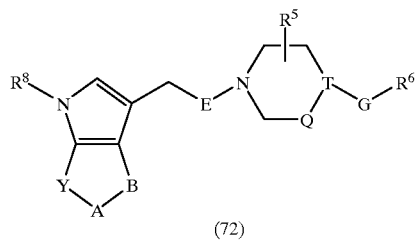

(72)

A compound of the formula (65) obtained by the method described in Chemistry of heterocyclic compounds, vol. 9, p. 920 (1982) is treated by the method described in Tetrahedron Lett. Vol. 14, p. 1721 (1968) to give a compound of the formula (66). This compound is reacted with a compound of the formula (54) wherein X is chlorine or bromine and other symbols are as defined above in a solvent that does not interfere with the reaction (e.g., methylene chloride, chloroform, methylene dichloride and nitrobenzene) in the presence of a Lewis acid (e.g., chloride aluminum, iron(III) chloride, tin chloride and boron trifluoride) at −78° C. to the refluxing temperature of the solvent for 1–24 hours to give a compound of the formula (67). This compound is reacted with a compound of the formula (26) or an acid addition salt thereof (e.g., hydrochloride, hydrobromide, sulfate and oxalate) in a suitable solvent that does not interfere with the reaction (e.g., tetrahydrofuran, dichloromethane, dimethylformamide and mixed solvents of optional members therefrom) in the presence of a suitable base (e.g., potassium carbonate, pyridine and triethylamine) at room temperature to the refluxing temperature of the solvent for 1–24 hours to give a compound of the formula (68). This compound is reacted in a two phase solvent of a suitable solvent that does not interfere with the reaction (e.g., methylene chloride, chloroform, toluene and 1,4-dioxane) and an aqueous solution of a suitable base (e.g., sodium hydroxide and potassium hydroxide) to give a compound of the formula (69).

This compound is reacted with a suitable reducing agent (e.g., sodium borohydride, borane and lithium aluminum hydride) in a solvent that does not interfere with the reaction (e.g., methanol, ethanol, propanol, methylene chloride, chloroform, methylene dichloride and mixed solvents of optional members therefrom) to give a compound of the formula (70). This compound is treated according to the method described in Bull. Chem. Soc. Jpn, vol. 62, p. 3532 (1989) to give a compound of the formula (71). A compound of the formula (69) is refluxed under heating in a solvent that does not interfere with the reaction (e.g., methanol, ethanol, propanol, butanol, ethylene glycol and dithylene glycol) in the presence of hydrazine and a base (e.g., sodium hydroxide and potassium hydroxide) for 1–24 hours to give a compound of the formula (71). This reaction can be also carried out by clemmensen reaction or thioketal method to give a compound of the formula (71).

The compound thus obtained is reacted with $R^8$-L wherein L is as defined above in a suitable solvent that does not interfere with the reaction (e.g., chloroform, tetrahydrofuran, toluene, dimethylformamide and mixed solvents of optional members therefrom) in the presence of a suitable base such as triethylamine, potassium carbonate, sodium hydroxide and potassium tertbutoxide to give the compound of the formula (72).

6. Compound wherein R is a group of the formula (8):

Method (1)

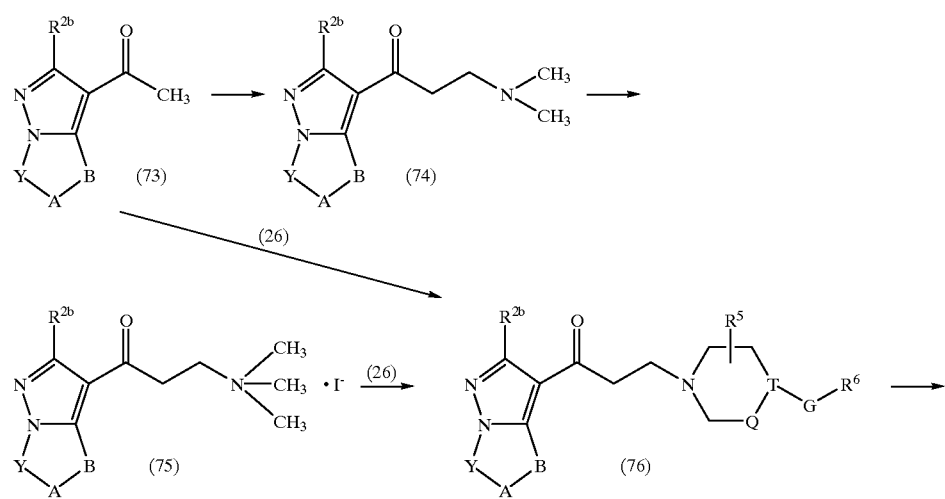

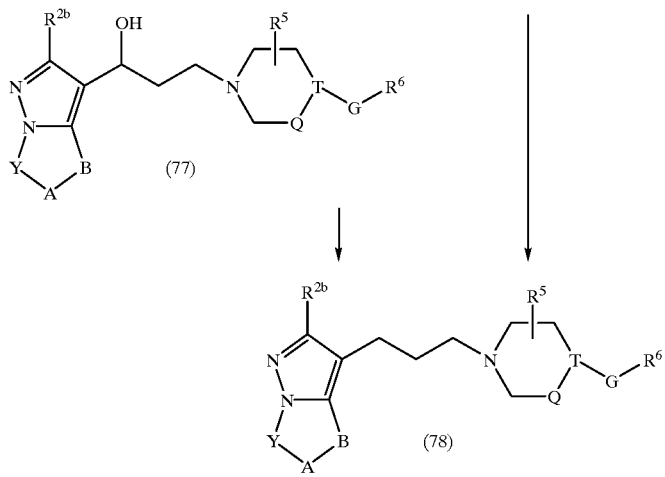

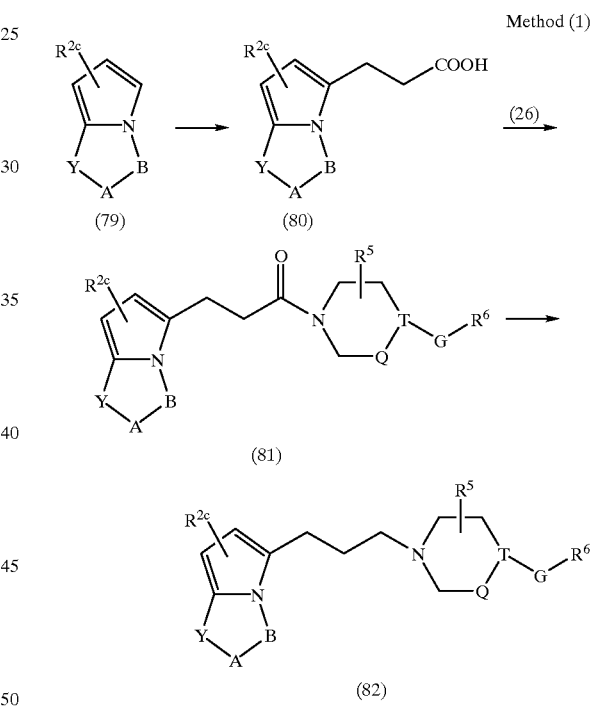

A compound of the formula (73) obtained by the method described in Tetrahedron Lett., vol. 30, p. 4625 (1989) is stirred with heating in acetic anhydride in the presence of dimethylamine hydrochloride and formaldehyde for 1–24 hours to give a compound of the formula (74). This compound is reacted with methyl iodide in a suitable solvent (e.g., methanol, ethanol and acetone) to give a compound of the formula (75). This compound is reacted in a suitable solvent (e.g., methanol, ethanol and propanol) in the presence of a compound of the formula (26) at room temperature to the refluxing temperature of the solvent for 1–24 hours to give a compound of the formula (76). A compound of the formula (73) is stirred with heating in acetic anhydride in the presence of hydrochloride of a compound of the formula (26) and formaldehyde for 1–24 hours to give a compound of the formula (76).

The compound of the formula (76) thus obtained is reacted with a suitable reducing agent such as sodium borohydride, borane and lithium aluminum hydride in a suitable solvent that does not interfere with the reaction (e.g., methanol, ethanol, propanol, methylene chloride, chloroform, methylene dichloride and mixed solvents of optional members therefrom) to give a compound of the formula (77). This compound is treated by the method described in Bull. Chem. Soc. Jpn., vol. 62, p. 3537 (1989) to give a compound of the formula (78). A compound of the formula (76) is refluxed under heating in a solvent that does not interfere with the reaction (e.g., methanol, ethanol, propanol, butanol, ethylene glycol and dithylene glycol) in the presence of hydrazine and a base (e.g., sodium hydroxide and potassium hydroxide) for 1–24 hours to give a compound of the formula (78). This reaction can be also carried out by clemmensen reaction or thioketal method to give a compound of the formula (78).

7. Compound wherein R is a group of the formula (9):

Using a compound of the formula (79) obtained by the method described in Heterocycles, vol. 31, p. 9 (1990) and in accordance with the method described in Japanese Patent Unexamined Publication No. 189179/1983, a compound of the formula (80) is obtained. This compound is reacted with a compound of the formula (26) using a fusing agent such as 1,3-dicyclohexylcarbodiimide, 1-ethyl-3-(3-dimethylaminopropyl)carbodiimide and cyanophosphonic acid diester in a suitable solvent that does not interfere with the reaction (e.g., tetrahydrofuran, dichloromethane, dimethylformamide and mixed solvents of optional members therefrom) in the presence of a tertiary amine such as triethylamine from under ice-cooling to room temperature for 1–24 hours to give a compound of the formula (81). When a reactive derivative (acid chloride and acylimidazol) of a compound of the formula (80) is used, the reaction proceeds in a suitable solvent that does not interfere with the reaction (e.g., tetrahydrofuran, dichloromethane, chloroform, benzene and mixed solvents of optional members therefrom) in the presence of a tertiary amine such as triethylamine or pyridine from under ice-cooling to room temperature for 1–24 hours.

The compound of the formula (81) thus obtained is reduced in a suitable solvent that does not interfere with the reaction (e.g., tetrahydrofuran, diethyl ether, toluene and mixed solvents of optional members therefrom) using a reducing agent such as lithium aluminum hydride and borane at −78° C. to the refluxing temperature of the solvent for 1–24 hours to give a compound of the formula (82).

reaction (e.g., tetrahydrofuran, dichloromethane, dimethylformamide and mixed solvents of optional members therefrom) in the presence of a suitable base (e.g., potassium carbonate, pyridine and triethylamine) at room temperature to the refluxing temperature of the solvent for 1–24 hours to give a compound of the formula (84). This compound is reacted with a suitable reducing agent (e.g., sodium borohydride, borane and lithium aluminum hydride) in a solvent that does not interfere with the reaction (e.g., methanol, ethanol, propanol, methylene chloride, chloroform, methylene dichloride and mixed solvents of optional members therefrom) to give a compound of the formula (85). This compound is treated according to the method described in Bull. Chem. Soc. Jpn., vol. 62, p. 3537 (1989) to give a compound of the formula (82). A compound of the formula (84) is refluxed under heating in a solvent that does not interfere with the reaction (e.g., methanol, ethanol, propanol, butanol, ethylene glycol and diethylene glycol) in the presence of hydrazine and a base (e.g., sodium hydroxide Method (2)

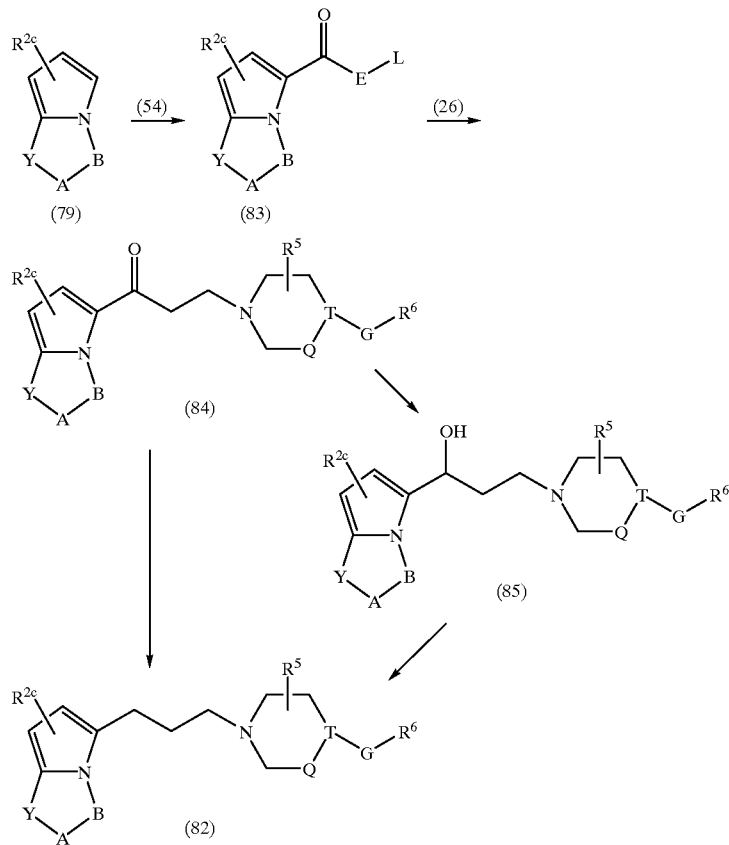

A compound of the formula (79) is reacted with a compound of the formula (54) wherein X is chlorine or bromine and other symbols are as defined above in a solvent that does not interfere with the reaction (e.g., methylene chloride, chloroform, methylene dichloride and nitrobenzene) in the presence of a Lewis acid (e.g., aluminum chloride, iron(III) chloride, tin chloride and boron trifluoride) at −78° C. to the refluxing temperature of the solvent for 1–24 hours to give a compound of the formula (83). This compound is reacted with a compound of the formula (26) or an acid addition salt thereof (e.g., hydrochloride, hydrobromide, sulfate and oxalate) in a suitable solvent that does not interfere with the and potassium hydroxide) for 1–24 hours to give a compound of the formula (82). This reaction can be also carried out by clemmensen reaction or thioketal method to give a compound of the formula (82).

The pharmaceutically acceptable salt of the compound of the formula (I) is exemplified by acid addition salt with inorganic acid or organic acid, which is obtained by treating the compound of the formula (I) with an inorganic acid (e.g., hydrochloric acid, hydrobromic acid, sulfuric acid, phosphoric acid and nitric acid), or organic acid (e.g., acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid and ascorbic acid) by a conventional method. For crystallization of the compound, oxalic acid may be added to give oxalate.

The inventive compound thus obtained can be separated and purified by a conventional method such as recrystallization and column chromatography. When the obtained product is a racemate, the desired optically active compounds can be obtained by preparative recrystallization from a salt with an optically active acid or by passing through a column packed with an optically active carrier. Each diastereomer can be separated by preparative recrystallization, chromatography and the like. These can be also obtained by the use of an optically active starting material. In addition, a stereoisomer can be separated by recrystallization, column chromatography and the like.

Inasmuch as the fused heterocyclic compound of the present invention, an optical isomer thereof and a pharmaceutically acceptable salt thereof show a strong blocking action on $D_4$ receptor and $5-HT_2$ receptor, as well as blockage of NMDA receptor hypofunction, they can be useful antipsychotic agents that are effective not only for positive symptoms centering on hallucination and delusion characteristic of the acute stage of schizophrenia, but also negative symptoms of apathy, abulia and autism. They are also expected to make antipsychotic agents associated with less side effects, such as extrapyramidal symptoms and endocrine disturbance, which are observed when a conventional antipsychotic agent having a $D_2$ receptor blocking action is administered. Therefore, the inventive compound can be used as a therapeutic agent for the diseases such as schizophrenia When the inventive compound is used as a pharmaceutical agent, the inventive compound is admixed with pharmaceutically acceptable carriers (e.g., excipients, binders, disintegrators, correctives, corrigents, emulsifying agents, diluents and solubilizers) to give a pharmaceutical composition which is then formulated by a conventional method to give tablets, pills, capsules, granules, powders, syrups, emulsions, elixirs, suspensions, solutions, injections, transfusions and suppositories which can be administered orally or parenterally.

In the present specification, by parenteral is meant subcutaneous injection, intravenous injection, intramuscular injection, intraperitoneal injection, transfusion and the like. A preparation for injection such as sterile aqueous and oily suspensions for injection can be prepared by a method known in this field using a suitable dispersing agent, wetting agent and suspending agent. The sterile preparation for injection may be a sterile injectable solution (e.g., aqueous solution) or suspension in a diluent or solvent that is nontoxic and parenterally administrable. Examples of usable vehicle and solvent include water, Ringer solution, isotonic brine and the like. In addition, sterile nonvolatile oil can be generally used as a solvent or a suspending solvent. Any nonvolatile oil or fatty acid can be used for this end, and examples thereof include natural, synthetic or semisynthetic lipid oil or fatty acid, and natural, synthetic or semisynthetic mono-, di- or triglycerides. A suppository for rectal administration can be prepared upon mixing a drug with a suitable nonirritant vehicle, such as cocoa butter and polyethylene glycols, which are solid at normal temperature and liquid at a temperature of the intestine and which melt in rectum to release the drug.

The solid dosage form for oral administration may be, for example, powder, granule, tablet, pill or capsule mentioned above. In these dosage forms, the active compound can be admixed with at least one additive, such as sucrose, lactose, cellulose sugar, mannitol, maltitol, dextran, starches, agar, arginates, chitins, chitosans, pectins, tragacanth gum, gum arabic, gelatins, collagens, casein, albumin, synthetic or semisynthetic polymers and glycerols. A product having such a dosage form may further contain different additives as usual, such as inert diluents, lubricants such as magnesium stearate, preservatives such as sodium p-hydroxybenzoate and sorbic acids, antioxidants such as ascorbic acid, α-tocopherol and cysteine, disintegrators, binders, thickeners, buffers, sweeteners, flavors, perfumes and the like. Tablets and pills may be enteric coated. The liquid preparation for oral administration is exemplified by pharmaceutically acceptable emulsion, syrup, elixir, suspension, solution and the lie, which may contain an inert diluent normally used in this field, such as water.

The dose is determined in consideration of age, body weight, general condition of health, sex, diet, administration time, administration route, excretion rate, combination of drugs, disease state being treated at that time of the patient and other factors. The inventive compound, an optical isomer thereof and a pharmaceutically acceptable salt thereof are low toxic and can be used safely. The daily dose, which is subject to change according to the condition and body weight of patient, the kind of compound, administration route and the like, is about 0.01–50 mg/patient/day, preferably 0.01–20 mg/patient/day, for subcutaneous, intravenous, intramuscular or intraperitoneal administration, and about 0.01–150 mg/patient/day, preferably 0.1–100 mg/patient/day, for oral administration.

The present invention is described in more detail by referring to the starting material synthesis examples, examples and formulation examples, to which the present invention is not limited.

Starting Material Synthesis Example 1

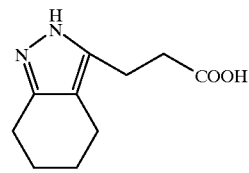

Hydrazine hydrate (1.1 g) was added to a solution (40 ml) of 4-oxo-4-(2-oxocyclohexyl)-n-butyric acid (4.1 g) in ethanol and the mixture was refluxed for 1 hour. After the completion of the reaction, the reaction mixture was cooled and the precitated crystals were collected by filtration to give 3.9 g of 3-(4,5,6,7-tetrahydro-2H-indazol-3-yl)propionic acid, m.p. 135–136° C.

Starting Material Synthesis Example 2

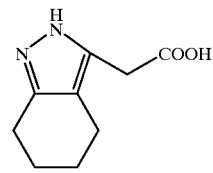

In the same manner as in Starting Material Synthesis Example 1 except that 4-oxo-4-(2-oxocyclohexyl)propionic acid was used as the starting material instead of 4-oxo-4-(2-oxocyclohexyl)-n-butyric acid, 2-(4,5,6,7-tetrahydro-2H-indazol-3-yl)acetic acid was obtained, m.p. 155–156° C.

Starting Material Synthesis Example 3

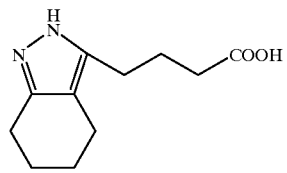

In the same manner as in Starting Material Synthesis Example 1 except that 4-oxo-4-(2-oxocyclohexyl)valeric acid was used as a starting material instead of 4-oxo-4-(2-oxocyclohexyl)-n-butyric acid, 4-(4,5,6,7-tetrahydro-2H-indazol-3-yl)-n-butyric acid was obtained, m.p. 94–96° C.

Starting Material Synthesis Example 4

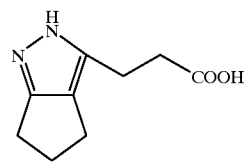

In the same manner as in Starting Material Synthesis Example 1 except that 4-oxo-4-(2-oxocyclopentyl)-n-butyric acid was used as a starting material instead of 4-oxo-4-(2-oxocyclohexyl)-n-butyric acid, 3-(2,4,5,6-tetrahydrocyclopentapyrazol-3-yl)propionic acid was obtained, m.p. 157–159° C.

Staring Material Synthesis Example 5

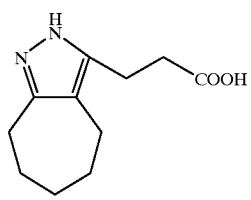

In the same manner as in Starting Material Synthesis Example 1 except that 4-oxo-4-(2-oxocycloheptyl)-n-butyric acid was used as a staring material instead of 4-oxo-4-(2-oxocyclohexyl)-n-butyric acid, 3-(2,4,5,6,7,8-hexahydrocycloheptapyrazol-3-yl)propionic acid was obtained, m.p. 102–105° C.

Starting Material Synthesis Example 6

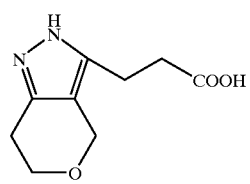

In the same manner as in Starting Material Synthesis Example 1 except that 4-oxo-4-(4-oxo-2,3,5,6-tetrahydro-4H-pyran-3-yl)-n-butyric acid is used as a starting material instead of 4-oxo-4-(2-oxocyclohexyl)-n-butyric acid, 3-(2,4,6,7-tetrahydropyrano[4,3-c]pyrazol-3-yl)propionic acid is obtained.

Starting Material Synthesis Example 7

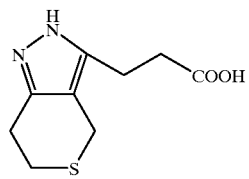

In the same manner as in Starting Material Synthesis Example 1 except that 4-oxo-4-(4-oxo-2,3,5,6-tetrahydro-4H-thiopyran-3-yl)-n-butiric acid is used as a starting material instead of 4-4-(2-oxocyclohexyl)-n-butyric acid, 3-(2,4,6,7-tetrahydrothiopyrano[4,3-c]pyrazol-3-yl)propionic acid is obtained.

Staring Material Synthesis Example 8

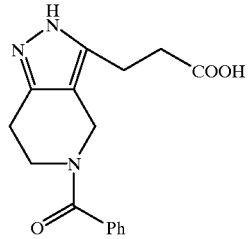

In the same manner as in Starting Material Synthesis Example 1 except that 4-oxo-4-(1-benzoyl-4-oxopiperidin-3-yl)-n-butyric acid was used as a starting material instead of 4-oxo-4-(2-oxocyclohexyl)-n-butyric acid, 3-(5-benzoyl-4,5,6,7-tetrahydro-2H-pyrazolo[4,3-]pyridin-3-yl)propionic acid was obtained, m.p. 143–145° C.

Starting Material Synthesis Example 9

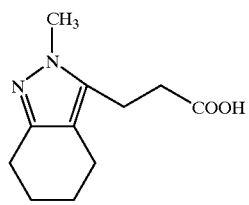

In the same manner as in Starting Material Synthesis Example 1 except that methylhydrazine is used as a starting material instead of hydrazine hydrate, 3-(4,5,6,7-tetrahydro-2-methyl-2H-indazol-3-yl)propionic acid is obtained.

Starting Material Synthesis Example 10

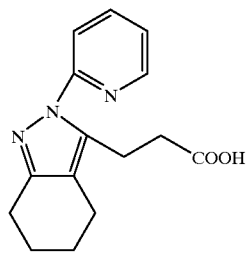

In the same manner as in Starting Material Synthesis Example 1 except that 2-pyridylhydrazine is used as a starting material instead of hydrazine hydrate, 3-(4,5,6,7-tetrahydro-2-(2-pyridyl)-2H-indazol-3-yl)propionic acid is obtained.

Starting Material Synthesis Example 11

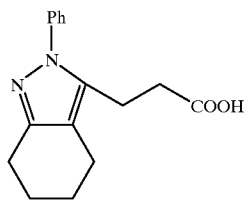

In the same manner as in Starting Material Synthesis Example 1 except that phenylhydrazine is used as a starting material instead of hydrazine hydrate, 3-(4,5,6,7-tetrahydro-2-phenyl-2H-indazol-3-yl)propionic acid is obtained.

Starting Material Synthesis Example 12

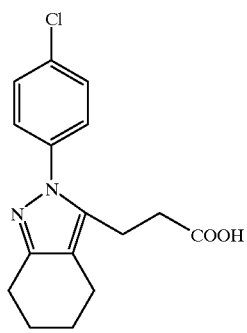

In the same manner as in Starting Material Synthesis Example 1 except that 4-chlorophenylhydrazine is used as a starting material instead of hydrazine hydrate, 3-(2-(4-chlorophenyl)4,5,6,7-tetrahydro-2H-indazol-3-yl)propionic acid is obtained.

Starting Material Synthesis Example 13

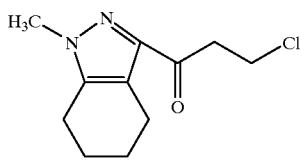

4,5,6,7-Tetrahydro-1-methyl-1H-indazole (10 g) and 3-chloropropionyl chloride (26 g) were dissolved in dichloroethane (100 ml) and aluminum chloride (28 g) was gradually added under an ice bath while stirring the mixture The reaction mixture was stirred for 17 hours at room temperature and poured into ice water. The reaction mixture was stirred for 2 hours at room temperature and extracted twice with chloroform. The chloroform layer was washed with saturated aqueous sodium hydrogencarbonate solution and saturated brine and dried over magnesium sulfate. The magnesium sulfate was filtered off and the solvent was evaporated under reduced pressure. The obtained residue was subjected to silica gel column chromatography (silica gel 100 g) and 3-(3-chloropropionyl)-4,5,6,7-tetrahydro-1-methyl-1H-indazole (10 g) was obtained from an eluate of hexane:ethyl acetate=20:1.

Starting Material Synthesis Example 14

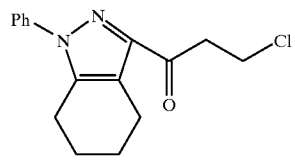

In the same manner as in Starting Material Synthesis Example 13 except that 4,5,6,7-tetrahydro-1-phenyl-1H-indazole is used as a starting material instead of 4,5,6,7-tetrahydro-1-methyl-1H-indazole, 3-(3-chloropropionyl)-4,5,6,7-tetrahydro-1-phenyl-2H-indazole is obtained.

Starting Material Synthesis Example 15

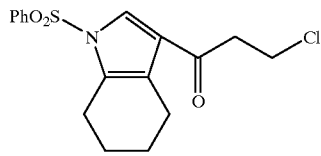

In the same manner as in Starting Material Synthesis Example 13 except that 1-benzenesulfonyl-4,5,6,7-tetrahydroindole is used as a starting material instead of 4,5,6,7-tetrahydro-1-methyl-1H-indazole, 1-benzenesulfonyl-3-(3-chloropropionyl)-4,5,6,7-tetrahydroindole is obtained.

Starting Material Synthesis Example 16

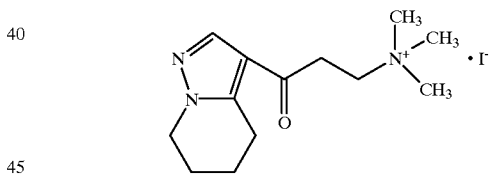

Acetic anhydride (4.3 g) was dropwise added while stirring dimethylamine hydrochloride (1.0 g) and 37% formaldehyde solution (1.0 g) at 50° C. After the dropwise addition, the reaction mixture was stirred at 80° C. for 1 hour, and 3-acetyl-4,5,6,7-tetrahydropyrazolo[2,3-a]pyridine (1.4 g) was added. The mixture was stirred for 2 hours with heating. The reaction mixture was poured into ice water and potassium carbonate was added, which was followed by extraction with chloroform. The extract was dried over magnesium sulfate and the solution was evaporated under reduced pressure to give 1.75 g of 3-(3-(N,N-dimethylamino)propionyl)-4,5,6,7-tetrahydropyrazolo[2,3-a]pyridine. This compound (1.75 g) was dissolved in acetone (10 ml) and methyl iodide (1.1 g) was added. The precipitated crystals were collected by filtration to give 1.2 g of a quaternary salt of (3-(4,5,6,7-tetrahydropyrazolo[2,3-a]pyridin-3-yl)-3-oxypropyl)trimethylammonium iodide, m.p. 210–213° C.

Starting Material Synthesis Example 17

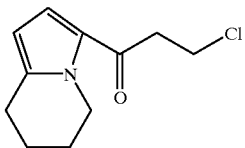

In the same manner as in Starting Material Synthesis Example 13 except that 5,6,7,8-tetrahydroindolizine is used as a staring material instead of 4,5,6,7-tetrahydro-1-methyl-1H-indazole, 3-(3-chloropropionyl)-5,6,7,8-tetrahydroindolizine is obtained.

EXAMPLE 1

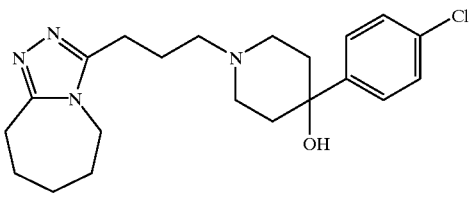

To a solution (30 ml) of 1-aza-2-methylthio-1-cycloheptene (1.43 g) in butanol was added 3-(4-(4-chlorophenyl)-4-hydroxypiperidin-1-yl)propylcarbohydrazide (3.12 g) with stirring, and the mixture was refluxed under heating for 3 hours. After the completion of the reaction, the solvent was evaporated under reduced pressure, and the obtained residue was recrystallized from isopropyl alcohol to give 0.1 g of 3-(3-(4-(4-chlorophenyl)-4-hydroxypiperidin-1-yl)propyl)-6,7,8,9-tetrahydro-5H-1,2,4-triazolo[4,3-a]azepine, m.p. 163° C.

EXAMPLE 2

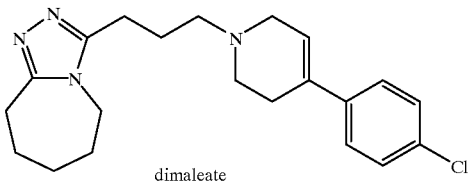

dimaleate

To a solution (30 ml) of 1-aza-2-methylthio-1-cycloheptene (1.43 g) in butanol was added 3-(4-(4-chlorophenyl)-1,2,3,6-tetrahydropyridin- 1-yl)propylcarbohydrazide (3.13 g) with stirring, and the mixture was refluxed under heating for 3 hours. After the completion of the reaction, the solvent was evaporated under reduced pressure, and the obtained residue was dissolved in isopropyl alcohol and maleic acid was added to form a salt. The salt was collected by filtration and recrystallized from ethanol to give 4.2 g of 3-(3-(4-(4-chlorophenyl)-1,2,3,6-tetrahydropyridin-1-yl)propyl-6,7,8,9-tetrahydro-5H-1,2,4-triazolo[4,3-a]azepine dimaleate, m.p. 186° C.

EXAMPLE 3

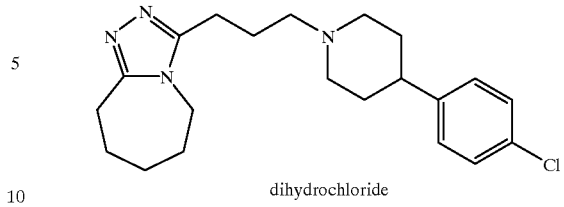

dihydrochloride 3-(3-(4-(4-Chlorophenyl)-4-hydroxypiperidin-1-yl)propyl)-6,7,8,9-tetrahydro-5H-1,2,4-triazolo[4,3-a]azepine (1 g) obtained in Example 1 was added to a solution (20 ml) of sodium iodide (2.76 g) and trimethylsilyl chloride (2 g) in acetonitrile with stirring, and the mix was refluxed under heating for 3 hours. After the completion of the reaction, the solvent was evaporated under reduced pressure, and the obtained residue was dissolved in isopropyl alcohol. A solution of hydrogen chloride in isopropyl alcohol was added to form a hydrochloride thereof, which was collected by filtration and recrystallized from ethanol to give 0.1 g of 3-(3-(4-(4-chlorophenyl)piperidin-1-yl)propyl-6,7,8,9-tetrahydro-5H-1,2,4-triazolo[4,3-a]azepine dihydrochloride, m.p. not less than 250° C.

EXAMPLE 4

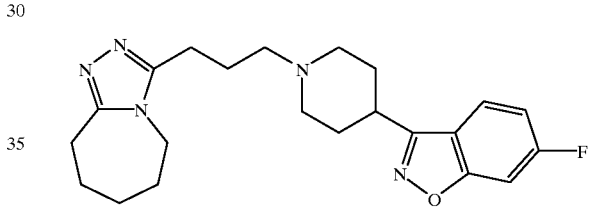

To a solution (150 ml) of 1-aza-2-methoxy-1-cycloheptene (23.6 g) in butanol was added 3-hydroxypropylcarbohydrazide (23 g) with stirring, and the mixture was refluxed under heating for 3 hours. After the completion of the reaction, the solvent was evaporated under reduced pressure, and the obtained residue was subjected to silica gel column chromatography to give 29 g of 3-(3-hydroxypropyl)-6,7,8,9-tetrahydro-5H-1,2,4-triazolo[4,3-a]azepine. To a solution of this compound (0.98 g) in dimethylformamide (20 ml) were added triethylamine (1.4 ml) and methanesulfonyl chloride (0.62 ml) with stirring. Then, 4-(6-fluoro-1,2-benzisoxazol-3-yl)piperidine (1.28 g), potassium carbonate (1.38 g) and potassium iodide (0.83 g) were added and the mixture was stirred for 4 hours at 60° C. After the completion of the reaction, the reaction mixture was poured into water, extracted with ethyl acetate, washed with water, and dried over magnesium sulfate. The solution was concentrated under reduced pressure to give 3-(3-(4-(6-fluoro-1,2-benzisoxazol-3-yl)piperidin-1-yl)propyl)-6,7,8,9-tetrahydro-5H-1,2,4-triazolo[4,3-a]azepine.

For crystallization, the obtained compound was dissolved in isopropyl alcohol and oxalic acid was added thereto to form a salt thereof, which was collected by filtration and recrystallized from ethanol to give 0.38 g of 3-(3-(4-(6-fluoro-1,2-benzisoxazol-3-yl)piperidin-1-yl)propyl)-6,7,8,9-tetrahydro-5H-1,2,4-triazolo[4,3-a]azepine dioxalate, m.p. 151–153° C.

EXAMPLE 5

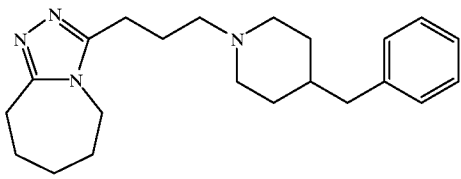

Triethylamine (1.4 ml) and methanesulfonyl chloride (0.62 ml) were added to a solution of 3-(3-hydroxypropyl)-6,7,8,9-tetrahydro-5H-1,2,4-triazolo[4,3-a]azepine (0.98 g) obtained in the same manner as in Example 4 in dimethylformamide (20 ml) with stirring. Then, $^4$-benzylpiperidine (0.88 g), potassium carbonate (1.38 g) and potassium iodide (0.83 g) were added and the mixture was stirred for 4 hours at 60° C. After the completion of the reaction, the reaction mixture was poured into water, extracted with ethyl acetate, washed with water, and dried over magnesium sulfate. The solution was concentrated under reduced pressure to give 3-(3-(4-benzylpiperidin-1-yl)propyl)-6,7,8,9-tetrahydro-5H-1,2,4-triazolo[4,3-a]azepine.

For crystallization, the obtained compound was dissolved in isopropyl alcohol and oxalic acid was added thereto to form a salt thereof, which was collected by filtration and recrystallized from ethanol to give 0.15 g of 3-(3-(4-benzylpiperidin-1-yl)propyl)-6,7,8,9-tetrahydro-5H-1,2,4-triazolo[4,3-a]azepine dioxalate, m.p. 156–158° C.

EXAMPLE 6

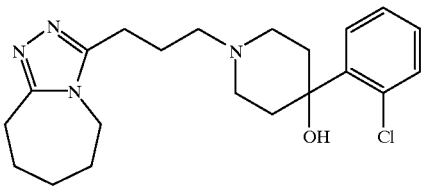

By the same reaction and treatment as in Example 1 using 1-aza-2-methoxy-1-cycloheptene and 3-(4-(2-chlorophenyl)-4-hydroxypiperidin-1-yl)propylcarbohydrazide, 3-(3-(4-(2-chlorophenyl)-4-hydroxypiperidin-1-yl)propyl)-6,7,8,9-tetrahydro-5H-1,2,4-triazolo[4,3-a]azepine is obtained.

EXAMPLE 7

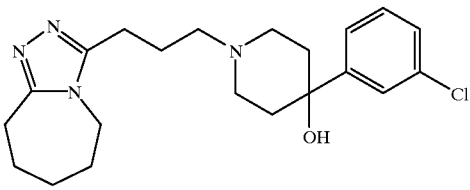

By the same reaction and treatment as in Example 1 using 1-aza-2-methoxy-1-cycloheptene and 3-(4-(3-chlorophenyl)-4-hydroxypiperidin-1-yl)propylcarbohydrazide, 3-(3-(4-(3-chlorophenyl)-4-hydroxypiperidin-1-yl)propyl)-6,7,8,9-tetrahydro-5H-1,2,4-triazolo[4,3-a]azepine was obtained, m.p. 146–148° C.

EXAMPLE 8

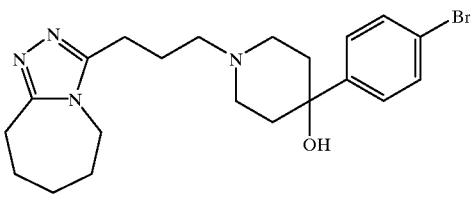

By the same reaction and treatment as in Example 1 using 1-aza-2-methoxy-1-cycloheptene and 3-(4-(4-bromophenyl)-4-hydroxypiperidin-1-yl)propylcarbohydrazide, 3-(3-(4-(4-bromophenyl)-4-hydroxypiperidin-1-yl)propyl)-6,7,8,9-tetrahydro-5H-1,2,4-triazolo[4,3-a]azepine is obtained.

EXAMPLE 9

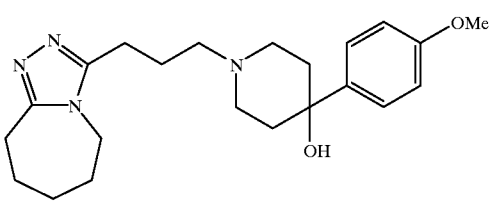

By the same reaction and treatment as in Example 1 using 1-aza-2-methoxy-1-cycloheptene and 3-(4-hydroxy-4-(4-methoxyphenyl)piperidin-1-yl)propylcarbohydrazide, 3-(3-(4-hydroxy-4-(4-methoxyphenyl)piperidin-1-yl)propyl)-6,7,8,9-tetrahydro-5H-1,2,4-triazolo[4,3-a]azepine is obtained.

EXAMPLE 10

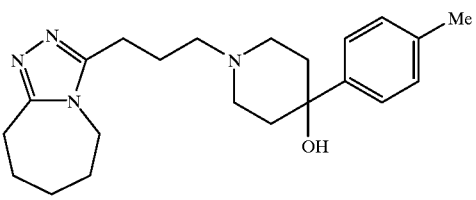

By the same reaction and treatment as in Example 1 using 1-aza-2-methoxy-1-cycloheptene and 3-(4-hydroxy-4-(4-methylphenyl)piperidin-1-yl)propylcarbohydrazide, 3-(3-(4-hydroxy-4-(4-methylphenyl)piperidin-1-yl)propyl)-6,7,8,9-tetrahydro-5H-1,2,4-triazolo[4,3-a]azepine was obtained, m.p. 160–161° C.

EXAMPLE 11

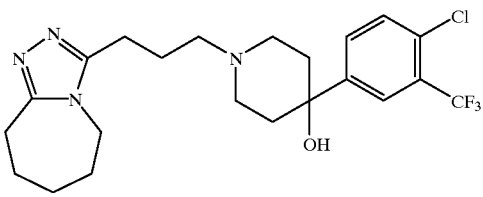

To a solution (30 ml) of 1-aza-2-methoxy-1-cycloheptene (2.31 g) in butanol was added 3-(4-(4-chloro-3-trifluoromethylphenyl)-1-hydroxypiperidin-1-yl)propylcarbohydrazide (3.5 g) with stirring, and the mixture was refluxed under heating for 3 hours. After the completion of the reaction, the solvent was evaporated under reduced pressure, and the obtained residue was recrystallized from a mixed solvent of ethyl alcohol and ethyl acetate to give 2.8 g of 3-(3-(4-(4-chloro-3-trifluoromethylphenyl)-4-hydroxypiperidin-1-yl)propyl)-6,7,8,9-tetrahydro-5H-1,2,4-triazolo[4,3-a]azepine, m.p. 151° C.

EXAMPLE 12

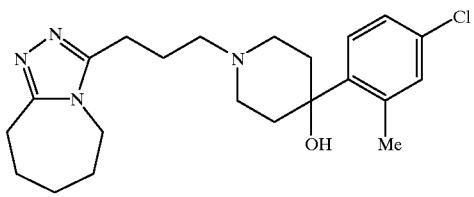

By the same reaction and treatment as in Example 1 using 1-aza-2-methoxy-1-cycloheptene and 3-(4-(4-chloro-2-methylphenyl)-4-hydroxypiperidin-1-yl)propylcarbohydrazide, 3-(3-(4-(4-chloro-2-methylphenyl)-4-hydroxypiperidin-1-yl)propyl)-6,7,8,9-tetrahydro-5H-1,2,4-triazolo[4,3-a]azepine is obtained.

EXAMPLE 13

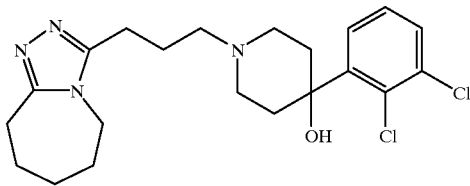

By the same reaction and treatment as in Example 1 using 1-aza-2-methoxy-1-cycloheptene and 3-(4-(2,3-dichlorophenyl)-4-hydroxypiperidin-1-yl)propylcarbohydrazide, 3-(3-(4-(2,3-dichlorophenyl)-4-hydroxypiperidin-1-yl)propyl)-6,7,8,9-tetrahydro-5H-1,2,4-triazolo[4,3-a]azepine is obtained.

EXAMPLE 14

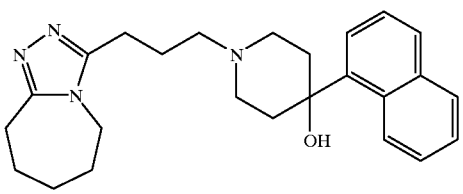

By the same reaction and treatment as in Example 1 using 1-aza-2-methoxy-1-cycloheptene and 3-(4-hydroxy-4-(1-naphthyl)piperidin-1-yl)propylcarbohydrazide, 3-(3-(4-hydroxy-4-(1-naphthyl)piperidin-1-yl)propyl)-6,7,8,9-tetrahydro-5H-1,2,4-triazolo[4,3-a]azepine is obtained.

EXAMPLE 15

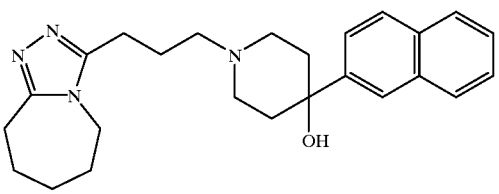

By the same reaction and treatment as in Example 1 using 1-aza-2-methoxy-1-cycloheptene and 3-(4-hydroxy-4-(2-naphthyl)piperidin-1-yl)propylcarbohydrazide, 3-(3-(4-hydroxy-4-(2-naphthyl)piperidin-1-yl)propyl)-6,7,8,9-tetrahydro-5H-1,2,4-triazolo[4,3-a]azepine is obtained.

EXAMPLE 16

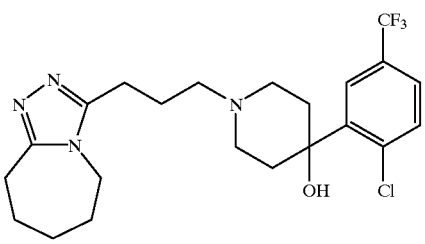

By the same reaction and treatment as in Example 1 using 1-aza-2-methoxy-1-cycloheptene and 3-(4-(2-chloro-5-trifluoromethylphenyl)4-hydroxypiperidin-1-yl)propylcarbohydrazide, 3-(3-(4-(2-chloro-5-trifluoromethylphenyl)-4-hydroxypiperidin-1-yl)propyl)-6,7,8,9-tetrahydro-5H-1,2,4-triazolo[4,3-a]azepine is obtained.

EXAMPLE 17

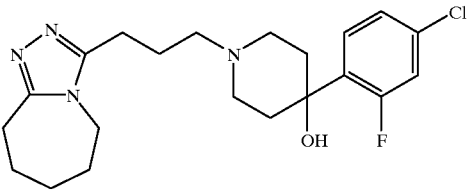

By the same reaction and treatment as in Example 1 using 1-aza-2-methoxy-1-cycloheptene and 3-(4-(4-chloro-2-fluorophenyl)-4-hydroxypiperidin-1-yl)propylcarbohydrazide, 3-(3-(4-(4-chloro-2-fluorophenyl)-4-hydroxypiperidin-1-yl)propyl)-6,7,8,9-tetrahydro-5H-1,2,4-triazolo[4,3-a]azepine is obtained.

EXAMPLE 18

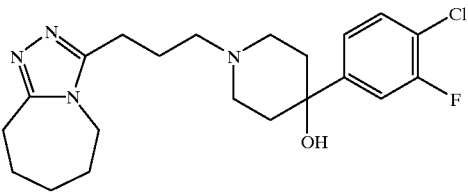

By the same reaction and treatment as in Example 1 using 1-aza-2-methoxy-1-cycloheptene and 3-(4-(4-chloro-3-fluorophenyl)-4-hydroxypiperidin-1-yl)propylcarbohydrazide, 3-(3-(4-(4-chloro-3-fluorophenyl)-4-hydroxypiperidin-1-yl)propyl)-6,7,8,9-tetrahydro-5H-1,2,4-triazolo[4,3-a]azepine is obtained.

EXAMPLE 19

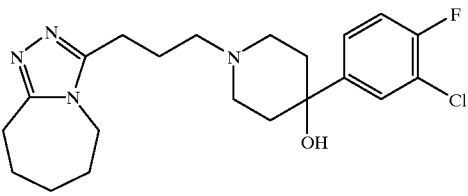

By the same reaction and treatment as in Example 1 using 1-aza-2-methoxy-1-cycloheptene and 3-(4-(3-chloro-4-fluorophenyl)-4-hydroxypiperidin-1-yl)propylcarbohydrazide, 3-(3-(4-(3-chloro-4-fluorophenyl)-4-hydroxypiperidin-1-yl)propyl)-6,7,8,9-tetrahydro-5H-1,2,4-triazolo[4,3-a]azepine is obtained.

EXAMPLE 20

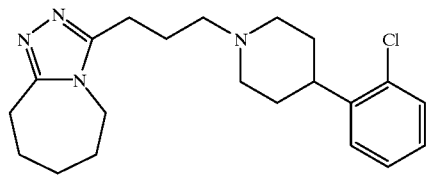

By the same reaction and treatment as in Example 1 using 1-aza-2-methoxy-1-cycloheptene and 3-(4-(2-chlorophenyl) piperidin-1-yl)propylcarbohydrazide, 3-(3-(4-(2-chlorophenyl)piperidin-1-yl)propyl)-6,7,8,9-tetrahydro-5H-1,2,4-triazolo[4,3-a]azepine is obtained.

EXAMPLE 21

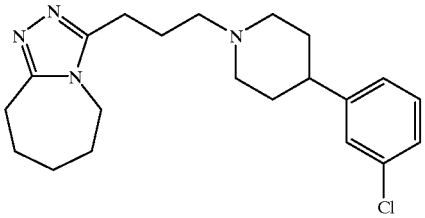

By the same reaction and treatment as in Example 1 using-1-aza-2-methoxy-1-cycloheptene and 3-(4-(3-chlorophenyl)piperidin-1-yl)propylcarbohydrazide, 3-(3-(4-(3-chlorophenyl)piperidin-1-yl)propyl)-6,7,8,9-tetrahydro-5H-1,2,4-triazolo[4,3-a]azepine is obtained.

EXAMPLE 22

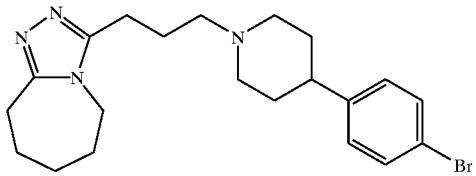

By the same reaction and treatment as in Example 1 using 1-aza-2-methoxy-1-cycloheptene and 3-(4-(4-bromophenyl) piperidin-1-yl)propylcarbohydrazide, 3-(3-(4-(4-bromophenyl)piperidin-1-yl)propyl)-6,7,8,9-tetrahydro-5H-1,2,4-triazolo[4,3-a]azepine is obtained.

EXAMPLE 23

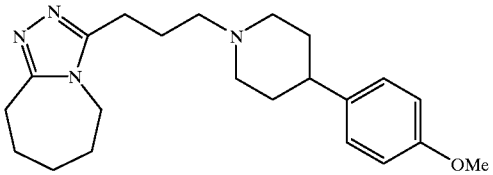

By the same reaction and treatment as in Example 1 using 1-aza-2-methoxy-1-cycloheptene and 3-(4-(4-methoxyphenyl)piperidin-1-yl)propylcarbohydrazide, 3-(3-(4-(4-methoxyphenyl)piperidin-1-yl)propyl)-6,7,8,9-tetrahydro-5H-1,2,4triazolo[4,3-a]azepine is obtained.

EXAMPLE 24

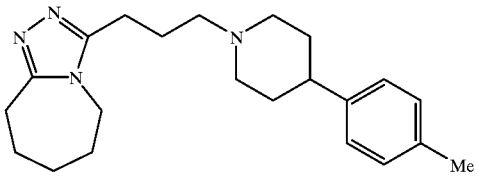

By the same reaction and treatment as in Example 1 using 1-aza-2-methoxy-1-cycloheptene and 3-(4-(4- methylphenyl)piperidin-1-yl)propylcarbohydrazide, 3-(3-(4-(4-methylphenyl)piperidin-1-yl)propyl)-6,7,8,9-tetrahydro-5H-1,2,4-triazolo[4,3-a]azepine is obtained.

EXAMPLE 25

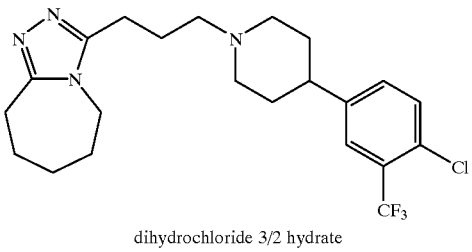

dihydrochloride 3/2 hydrate

To a solution of sodium iodide (0.43 g) and trimethylsilyl chloride (0.32 g) in acetonitrile (40 ml) was added 3-(3-(4-(4-chloro-3-trifluoromethylphenyl)-4-hydroxypiperidin-1-yl)propyl)-6,7,8,9-tetrahydro-5H-1,2,4-triazolo[4,3-a]azepine (0.22 g) obtained in Example 11 with stirring, and the mixture was refluxed under heating for 3 hours. After the completion of the reaction, the solvent was evaporated under reduced pressure, and the obtained residue was dissolved in isopropyl alcohol. Thereto was added a solution of hydrogen chloride in isopropyl alcohol to form a hydrochloride thereof, which was collected by filtration and recrystallized from ethanol to give 0.05 g of 3-(3-(4-(4-chloro-3-trifluoromethylphenyl)piperidin-1-yl)propyl)-6,7,8,9-tetrahydro-5H-1,2,4- triazolo[4,3-a]azepine dihydrochloride 3/2 hydrate, m.p. 255° C. (decomposition).

EXAMPLE 26

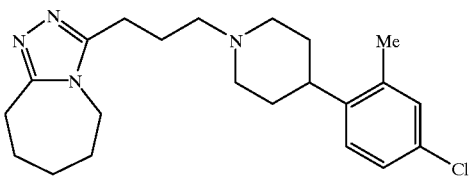

By the same reaction and treatment as in Example 1 using 1-aza-2-methoxy-1-cycloheptene and 3-(4-(4-chloro-2-methylphenyl)piperidin-1-yl)propylcarbohydrazide, 3-(3-(4-(4-chloro-2-methylphenyl)piperidin-1-yl)propyl)-6,7,8,9-tetrahydro-5H-1,2,4-triazolo[4,3-a]azepine is obtained.

EXAMPLE 27

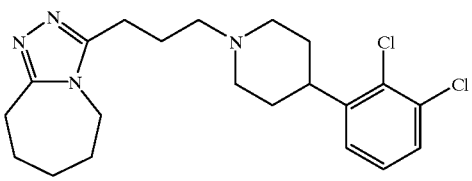

By the same reaction and treatment as in Example 1 using 1-aza-2-methoxy-1-cycloheptene and 3-(4-(2,3-dichlorophenyl)piperidin-1-yl)propylcarbohydrazide, 3-(3-(4-(2,3-dichlorophenyl)piperidin-1-yl)propyl)-6,7,8,9-tetrahydro-5H-1,2,4-triazolo[4,3-a]azepine is obtained.

EXAMPLE 28

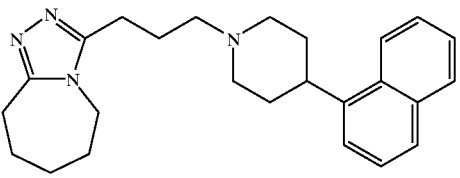

By the same reaction and treatment as in Example 1 using 1-aza-2-methoxy-1-cycloheptene and 3-(4-(1-naphthyl)piperidin-1-yl)propylcarbohydrazide, 3-(3-(4-(1-naphthyl)piperidin-1-yl)propyl)-6,7,8,9-tetrahydro-5H-1,2,4-triazolo[4,3-a]azepine is obtained.

EXAMPLE 29

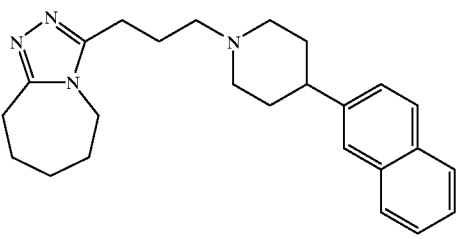

By the same reaction and treatment as in Example 1 using 1-aza-2-methoxy-1-cycloheptene and 3-(4-(2-naphthyl)piperidin-1-yl)propylcarbohydrazide, 3-(3-(4-(2-naphthyl)piperidin-1-yl)propyl)-6,7,8,9-tetrahydro-5H-1,2,4-triazolo[4,3-a]azepine is obtained.

EXAMPLE 30

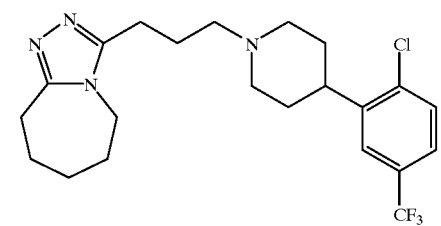

By the same reaction and treatment as in Example 1 using 1-aza-2-methoxy-1-cycloheptene and 3-(4-(2-chloro-5-trifluoromethylphenyl)piperidin-1-yl)propylcarbohydrazide, 3-(3-(4-(2-chloro-5-trifluoromethylphenyl)piperidin-1-yl)propyl)-6,7,8,9-tetrahydro-5H-1,2,4-triazolo[4,3-a]azepine is obtained.

EXAMPLE 31

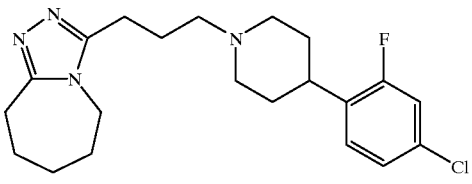

By the same reaction and treatment as in Example 1 using 1-aza-2-methoxy-1-cycloheptene and 3-(4-(4-chloro-2- fluorophenyl)piperidin-1-yl)propylcarbohydrazide, 3-(3-(4-(4-chloro-2-fluorophenyl)piperidin-1-yl)propyl)-6,7,8,9-tetrahydro-5H-1,2,4-triazolo[4,3-a]azepine is obtained.

EXAMPLE 32

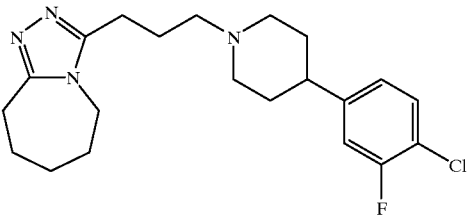

By the same reaction and treatment as in Example 1 using 1-aza-2-methoxy-1-cycloheptene and 3-(4-(4-chloro-3-fluorophenyl)piperidin-1-yl)propylcarbohydrazide, 3-(3-(4-(4-chloro-3-fluorophenyl)piperidin-1-yl)propyl)-6,7,8,9-tetrahydro-5H-1,2,4-triazolo[4,3-a]azepine is obtained.

EXAMPLE 33

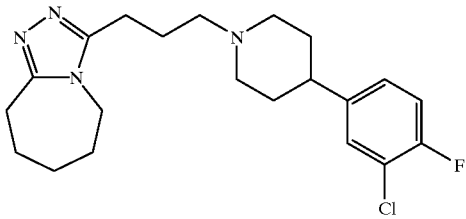

By the same reaction and treatment as in Example 1 using 1-aza-2-methoxy-1-cycloheptene and 3-(4-(3-chloro-4-fluorophenyl)piperidin-1-yl)propylcarbohydrazide, 3-(3-(4-(3-chloro-4-fluorophenyl)piperidin-1-yl)propyl)-6,7,8,9-tetrahydro-5H-1,2,4-triazolo[4,3-a]azepine is obtained.

EXAMPLE 34

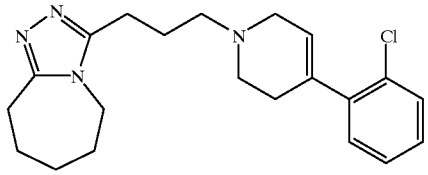

By the same reaction and treatment as in Example 1 using 1-aza-2-methoxy-1-cycloheptene and 3-(4-(2-chlorophenyl)-1,2,3,6-tetrahydropyridin-1-yl)propylcarbohydrazide, 3-(3-(4-(2-chlorophenyl)-1,2,3,6-tetrahydropyridin-1-yl)propyl)-6,7,8,9-tetrahydro-5H-1,2,4-triazolo[4,3-a]azepine is obtained.

EXAMPLE 35

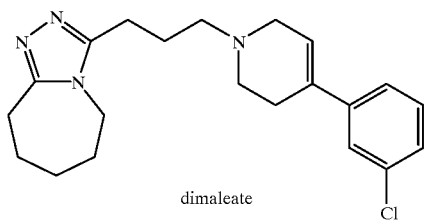

dimaleate

By the same reaction and treatment as in Example 1 using 1-aza-2-methoxy-1-cycloheptene and 3-(4-(3-chlorophenyl)-1,2,3,6-tetrahydropyridin-1-yl)propylcarbohydrazide and then by a conventional treatment using maleic acid, 3-(3-(4-(3-chlorophenyl)-1,2,3,6-tetrahydropyridin-1-yl)propyl)-6,7,8,9-tetrahydro-5H-1,2,4-triazolo[4,3-a]azepine dimaleate was obtained, m.p. 173–174° C.

EXAMPLE 36

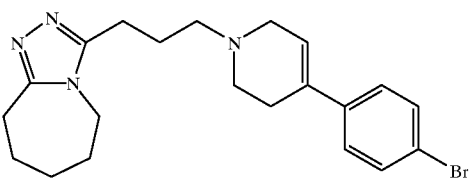

By the same reaction and treatment as in Example 1 using 1-aza-2-methoxy-1-cycloheptene and 3-(4-(4-bromophenyl)-1,2,3,6-tetrahydropyridin- 1-yl)propylcarbohydrazide, 3-(3-(4-(4-bromophenyl)-1,2,3,6-tetrahydropyridin-1-yl)propyl)-6,7,8,9-tetrahydro-5H-1,2,4-triazolo[4,3-a]azepine was obtained.

$^1$H-NMR(CDCl$_3$)δ: 1.62–1.80(4H,m), 1.81–1.92(2H,m), 2.01(2H,tt,J=7.7 Hz), 2.43–2.62(4H,m), 2.70(2H,t,J=6 Hz), 2.81(2H,t,J=7 Hz), 2.96(2H,t,J=6 Hz), 3.10–3.19(2H,m), 3.89(2H,t,J=5 Hz), 6.02–6.13(1H,m), 7.24(2H,d,J=9 Hz), 7.42(2H,d,J=9 Hz)

EXAMPLE 37

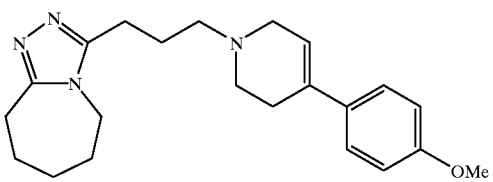

By the same reaction and treatment as in Example 1 using 1-aza-2-methoxy-1-cycloheptene and 3-(4-(4-methoxyphenyl)-1,2,3,6-tetrahydropyridin-1-yl)propylcarbohydrazide, 3-(3-(4-(4-methoxyphenyl)-1,2,3,6-tetrahydropyridin-1-yl)propyl)-6,7,8,9-tetrahydro-5H-1,2,4-triazolo[4,3-a]azepine was obtained.

$^1$H-NMR(CDCl$_3$)δ: 1.66–1.81(4H,m), 1.82–1.95(2H,m), 2.01(2H,tt,J=8.7 Hz), 2.41–2.53(2H,m), 2.56(2H,t,J=7 Hz), 2.69(2H,t,J=6 Hz), 2.79(2H,t,J=8 Hz), 2.96(2H,t,J=6 Hz), 3.08–3.18(2H,m), 3.81(3H,s), 3.90(2H,t,J=5 Hz), 5.92–6.01(1H,m), 6.85(2H,d,J=9 Hz), 7.32(2H,d,J=9 Hz)

EXAMPLE 38

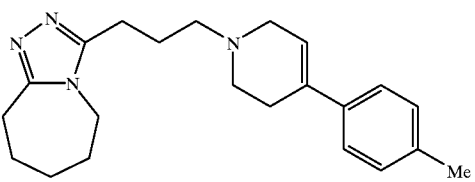

By the same reaction and treatment as in Example 1 using 1-aza-2-methoxy-1-cycloheptene and 3-(4-(4-methylphenyl)-1,2,3,6-tetrahydropyridin-1-yl)propylcarbohydrazide, 3-(3-(4-(4-methylphenyl)-1,2,3,6-tetrahydropyridin-1-yl)propyl)-6,7,8,9-tetrahydro-5H-1,2,4-triazolo[4,3-a]azepine was obtained, m.p. 93–96° C.

EXAMPLE 39

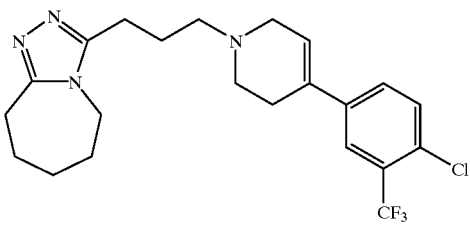

dihydrochloride ½ hydrate

To 3-(3-(4-(4-chloro-3-trifluoromethylphenyl)-4-hydroxypiperidin-1-yl)propyl)-6,7,8,9-tetrahydro-5H-1,2,4-triazolo[4,3-a]azepine (0.22 g) obtained in Example 11 were added water (2 ml) and conc. sulfuric acid (11 ml) and the mixture was stirred at 90° C. for 30 minutes with heating. After the completion of the reaction, the reaction mixture was made alkaline, extracted with chloroform, washed with water, and dried over magnesium sulfate. The solvent was evaporated under reduced pressure, and the obtained residue was dissolved in isopropyl alcohol. Thereto was added a solution of hydrogen chloride in isopropyl alcohol to form a hydrochloride thereof, which was collected by filtration and recrystallized from ethanol to give 0.15 g of 3-(3-(4-(4-chloro-3-trifluoromethylphenyl)-1,2,3,6-tetrahydropyridin-1-yl)propyl)-6,7,8,9-tetrahydro-5H-1,2,4-triazolo[4,3-a]azepine dihydrochloride 1/2 hydrate, m.p. 278° C. (decomposition).

EXAMPLE 40

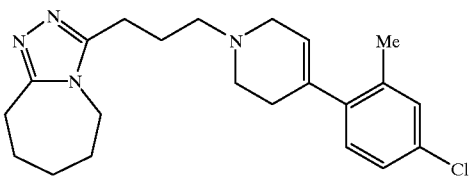

By the same reaction and treatment as in Example 1 using 1-aza-2-methoxy-1-cycloheptene and 3-(4-(4-chloro-2-methylphenyl)-1,2,3,6-tetrahydropyridin-1-yl)propylcarbohydrazide, 3-(3-(4-(4-chloro-2-methylphenyl)-1,2,3,6-tetrahydropyridin-1-yl)propyl)-6,7,8,9-tetrahydro-5H-1,2,4-triazolo[4,3-a]azepine was obtained.

$^1$H-NMR(CDCl$_3$)δ: 1.65–1.83(4H,m), 1.85–1.93(2H,m), 2.02(2H,tt,J=7.6 Hz), 2.26(3H,s), 2.30–2.41(2H,m), 2.59 (2H,t,J=7 Hz), 2.70(2H,t,J=5 Hz), 2.79(2H,t,J=7 Hz), 2.97 (2H,t,J=6 Hz), 3.09–3.21(2H,m), 3.91(2H,t,J=5 Hz), 5.49–5.55(1H,m), 7.01(1H,d,J=8 Hz), 7.09(1H,d,J=2 Hz), 7.15(1H,dd,J=8.2 Hz)

EXAMPLE 41

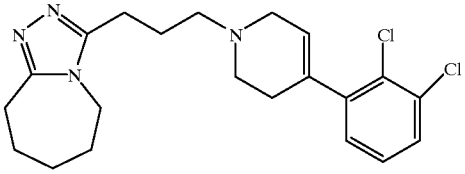

By the same reaction and treatment as in Example 1 using 1-aza-2-methoxy-1-cycloheptene and 3-(4-(2,3-dichlorophenyl)-1,2,3,6-tetrahydropyridin-1-yl)propylcarbohydrazide, 3-(3-(4-(2,3-dichlorophenyl)-1,2,3,6-tetrahydropyridin-1-yl)propyl)-6,7,8,9-tetrahydro-5H-1,2,4-triazolo[4,3-a]azepine was obtained.

$^1$H-NMR(CDCl$_3$)δ: 1.60–1.82(4H,m), 1.83–1.92(2H,m), 2.02(2H,tt,J=8.7 Hz), 2.40–2.50(2H,m), 2.58(2H,t,J=7 Hz), 2.70(2H,t,J=5 Hz), 2.80(2H,t,J=8 Hz), 2.97(2H,t,J=6 Hz), 3.11–3.18(2H,m), 3.93(2H,t,J=5 Hz), 5.61–5.68(1H,m), 7.10(1H,d,J=2 Hz), 7.15(1H,d,J=8 Hz), 7.36(1H,dd,J=8.2 Hz)

EXAMPLE 42

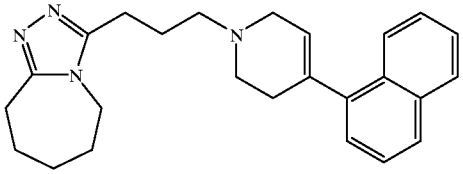

By the same reaction and treatment as in Example 1 using 1-aza-2-methoxy-1-cycloheptene and 3-(4-(1-naphthyl)-1,2,3,6-tetrahydropyridin-1-yl)propylcarbohydrazide, 3-(3-(4-(1-naphthyl)-1,2,3,6-tetrahydropyridin-1-yl)propyl)-6,7,8,9-tetrahydro-5H-1,2,4-triazolo[4,3-a]azepine is obtained.

EXAMPLE 43

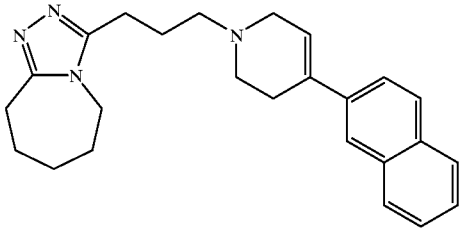

By the same reaction and treatment as in Example 1 using 1-aza-2-methoxy-1-cycloheptene and 3-(4-(2-naphthyl)-1,2,3,6-tetrahydropyridin-1-yl)propylcarbohydrazide, 3-(3-(4-(2-naphthyl)-1,2,3,6-tetrahydropyridin-1-yl)propyl)-6,7,8,9-tetrahydro-5H-1,2,4-triazolo[4,3-a]azepine was obtained.

$^1$H-NMR(CDCl$_3$)δ: 1.62–1.83(4H,m), 1.84–1.94(2H,m), 2.05(2H,tt,J=8.7 Hz), 2.61(2H,t,J=7 Hz), 2.67–2.86(6H,m), 2.96(2H,t,J=6 Hz), 3.17–3.26(2H,m), 3.91(2H,t,J=5 Hz), 6.20–6.29(1H,m), 7.39–7.50(3H,m), 7.57–7.63(1H,m), 7.72–7.85(4H,m)

EXAMPLE 44

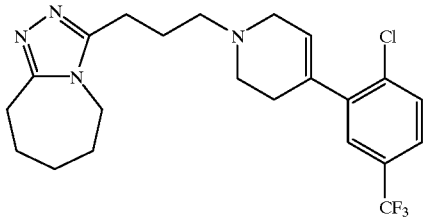

By the same reaction and treatment as in Example 1 using 1-aza-2-methoxy-1-cycloheptene and 3-(4-(2-chloro-5-trifluoromethylphenyl)-1,2,3,6-tetrahydropyridin-1-yl) propylcarbohydrazide, 3-(3-(4-(2-chloro-5-trifluoromethylphenyl)-1,2,3,6-tetrahydropyridin-1-yl) propyl)-6,7,8,9-tetrahydro-5H-1,2,4-triazolo[4,3-a]azepine is obtained.

EXAMPLE 45

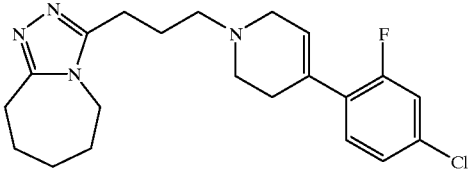

By the same reaction and treatment as in Example 1 using 1-aza-2-methoxy-1-cycloheptene and 3-(4-(4 chloro-2-fluorophenyl)-1,2,3,6-tetrahydropyridin-1-yl) propylcarbohydrazide, 3-(3-(4-(4-chloro-2-fluorophenyl)-1,2,3,6-tetrahydropyridin-1-yl)propyl)-6,7,8,9-tetrahydro-5H-1,2,4-triazolo[4,3-a]azepine is obtained.

EXAMPLE 46

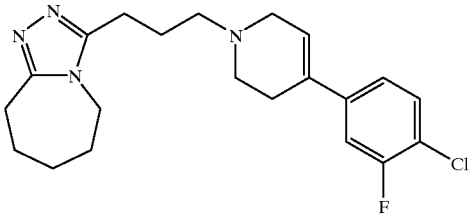

By the same reaction and treatment as in Example 1 using 1-aza-2-methoxy-1-cycloheptene and 3-(4(4-chloro-3-fluorophenyl)-1,2,3,6-tetrahydropyridin-1-yl) propylcarbohydrazide, 3-(3-(4-(4-chloro-3-fluorophenyl)-1, 2,3,6-tetrahydropyridin-1-yl)propyl)-6,7,8,9-tetrahydro-5H-1,2,4-triazolo[4,3-a]azepine is obtained.

EXAMPLE 47

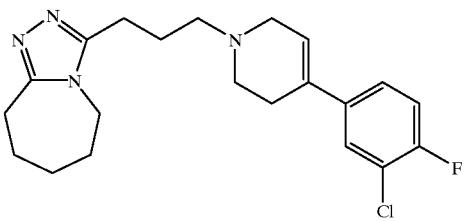

By the same reaction and treatment as in Example 1 using 1-aza-2-methoxy-1-cycloheptene and 3-(4-(3-chloro-4-fluorophenyl)-1,2,3,6-tetrahydropyridin-1-yl) propylcarbohydrazide, 3-(3-(4-(3-chloro-4-fluorophenyl)-1, 2,3,6-tetrahydropyridin-1-yl)propyl)-6,7,8,9-tetrahydro-5H-1,2,4-triazolo[4,3-a]azepine is obtained.

EXAMPLE 48

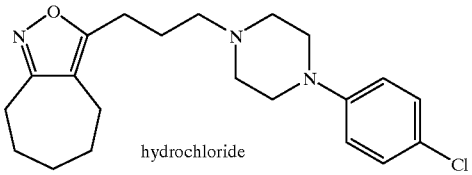

To a solution (8 ml) of cycloheptanone oxime (1.2 g) in tetrahydrofuran was added n-butyllithium (6 ml) under ice-cooling, and ethyl 4-(4-(4-chlorophenyl)piperazin-1-yl)-n-butyrate (1 g) was added, which was followed by stirring at room temperature for 1–24 hours. After the completion of the reaction, the solvent was evaporated under reduced pressure, and the obtained residue was dissolved in isopropyl alcohol. Then, a solution of hydrogen chloride in isopropyl alcohol to form a hydrochloride thereof, which was collected by filtration and recrystallized from ethanol to give 0.2 g of 3-(3-(4-(4-chlorophenyl)piperazin-1-yl)propyl)-5,6,7,8-tetrahydro-4H-cyclohepta[c]isoxazole hydrochloride, m.p. 220° C. (decomposition).

EXAMPLE 49

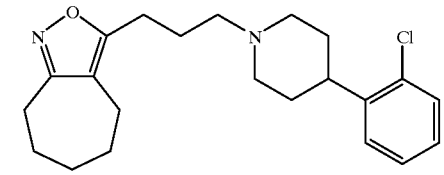

By the same reaction and treatment as in Example 48 using cycloheptanone oxime and ethyl 4-(4-(2-chlorophenyl)piperidin-1-yl)-n-butyrate, 3-(3-(4-(2-chlorophenyl)piperidin-1-yl)propyl)-5,6,7,8-tetrahydro-4H-cyclohepta[c]isoxazole is obtained.

EXAMPLE 50

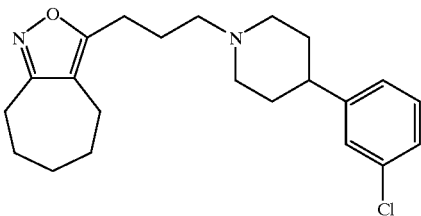

By the same reaction and treatment as in Example 48 using cycloheptanone oxime and ethyl 4-(4-(3-chlorophenyl)piperidin-1-yl)-n-butyrate, 3-(3-(4-(3-chlorophenyl)piperidin-1-yl)propyl)-5,6,7,8-tetrahydro-4H-cyclohepta[c]isoxazole is obtained.

EXAMPLE 51

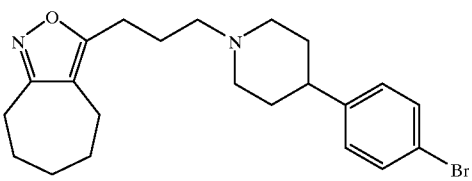

By the same reaction and treatment as in Example 48 using cycloheptanone oxime and ethyl 4-(4-(4-bromophenyl)piperidin-1-yl)-n-butyrate, 3-(3-(4-(4-bromophenyl)piperidin-1-yl)propyl)-5,6,7,8-tetrahydro-4H-cyclohepta[c]isoxazole is obtained.

EXAMPLE 52

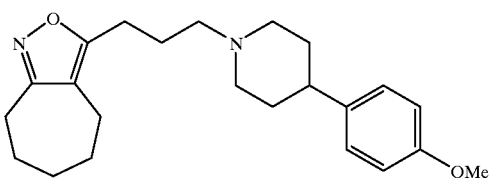

By the same reaction and treatment as in Example 48 using cycloheptanone oxime and ethyl 4-(4-(4-methoxyphenyl)piperidin-1-yl)-n-butyrate, 3-(3-(4-(4-methoxyphenyl)piperidin-1-yl)propyl)-5,6,7,8-tetrahydro-4H-cyclohepta[c]isoxazole is obtained.

EXAMPLE 53

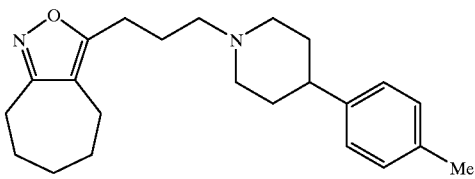

By the same reaction and treatment as in Example 48 using cycloheptanone oxime and ethyl 4-(4-(4-methylphenyl)piperidin-1-yl)-n-butyrate, 3-(3-(4-(4-methylphenyl)piperidin-1-yl)propyl)-5,6,7,8-tetrahydro-4H-cyclohepta[c]isoxazole is obtained.

EXAMPLE 54

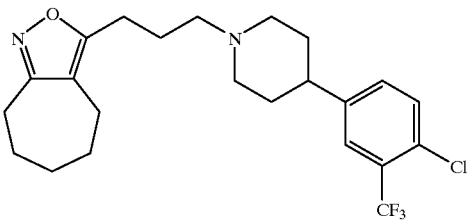

By the same reaction and treatment as in Example 48 using cycloheptanone oxime and ethyl 4-(4-(4-chloro-3-trifluoromethylphenyl)piperidin-1-yl)-n-butyrate, 3-(3-(4-(4-chloro-3-trifluoromethylphenyl)piperidin-1-yl)propyl)-5,6,7,8-tetrahydro-4H-cyclohepta[c]isoxazole is obtained.

EXAMPLE 55

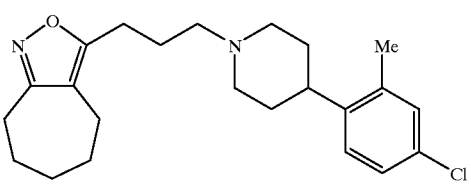

By the same reaction and treatment as in Example 48 using cycloheptanone oxime and ethyl 4-(4-(4-chloro-2-methylphenyl)piperidin-1-yl)-n-butyrate, 3-(3-(4-(4-chloro-2-methylphenyl)piperidin-1-yl)propyl)-5,6,7,8-tetrahydro-4H-cyclohepta[c]isoxazole is obtained.

EXAMPLE 56

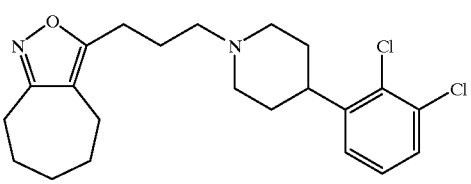

By the same reaction and treatment as in Example 48 using cycloheptanone oxime and ethyl 4-(4-(2,3-dichlorophenyl)piperidin-1-yl)-n-butyrate, 3-(3-(4-(2,3-dichlorophenyl)piperidin-1-yl)propyl)-5,6,7,8-tetrahydro-4H-cyclohepta[c]isoxazole is obtained.

EXAMPLE 57

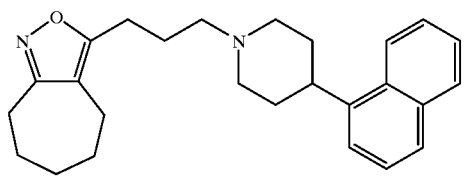

By the same reaction and treatment as in Example 48 using cycloheptanone oxime and ethyl 4-(4-(1-naphthyl)piperidin-1-yl)-n-butyrate, 3-(3-(4-(1-naphthyl)piperidin-1-yl)propyl-5,6,7,8-tetrahydro-4H-cyclohepta[c]isoxazole is obtained.

EXAMPLE 58

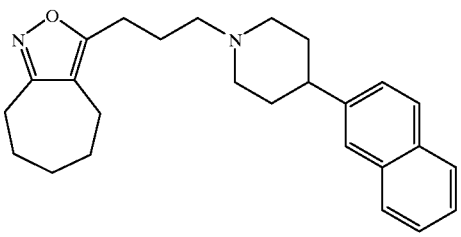

By the same reaction and treatment as in Example 48 using cycloheptanone oxime and ethyl 4-(4-(2-naphthyl)piperidin-1-yl)-n-butyrate, 3-(3-(4-(2-naphthyl)piperidin-1-yl)propyl)-5,6,7,8-tetrahydro-4H-cyclohepta[c]isoxazole is obtained.

EXAMPLE 59

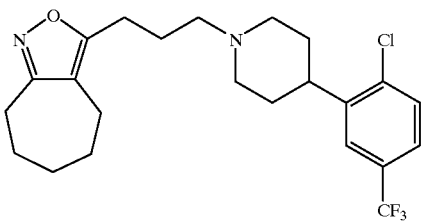

By the same reaction and treatment as in Example 48 using cycloheptanone oxide and ethyl 4-(4-(2-chloro-5-trifluoromethylphenyl)piperidin-1-yl)-n-butyrate, 3-(3-(4-(2-chloro-5-trifluoromethylphenyl)piperidin-1-yl)propyl)-5,6,7,8-tetrahydro-4H-cyclohepta[c]isoxazole is obtained.

EXAMPLE 60

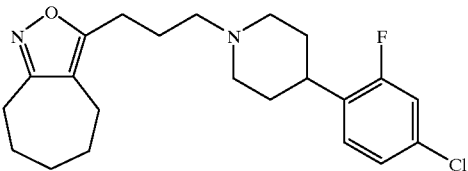

By the same reaction and treatment as in Example 48 using cycloheptanone oxime and ethyl 4-(4-(4-chloro-2-fluorophenyl)piperidin-1-yl)-n-butyrate, 3-(3-(4-(4-chloro-2-fluorophenyl)piperidin-1-yl)propyl)-5,6,7,8-tetrahydro-4H-cyclohepta[c]isoxazole is obtained.

EXAMPLE 61

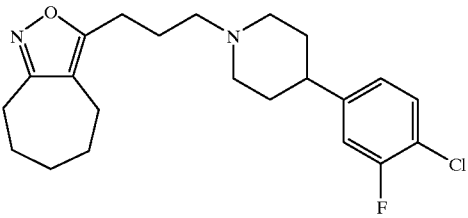

By the same reaction and treatment as in Example 48 using cycloheptanone oxime and ethyl 4-(4-(4-chloro-3-fluorophenyl)piperidin-1-yl)-n-butyrate, 3-(3-(4-(4-chloro-3-fluorophenyl)piperidin-1-yl)propyl)-5,6,7,8-tetrahydro-4H-cyclohepta[c]isoxazole is obtained.

EXAMPLE 62

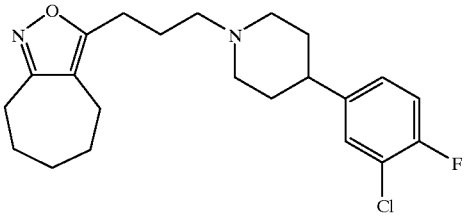

By the same reaction and treatment as in Example 48 using cycloheptanone oxime and ethyl 4-(4-(3-chloro-4-fluorophenyl)piperidin-1-yl)-n-butyrate, 3-(3-(4-(3-chloro-4-fluorophenyl)piperidin-1-yl)propyl)-5,6,7,8-tetrahydro-4H-cyclohepta[c]isoxazole is obtained.

EXAMPLE 63

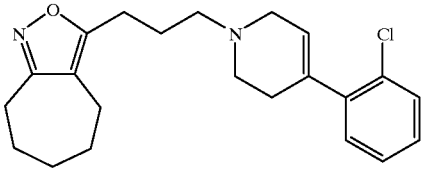

By the same reaction and treatment as in Example 48 using cycloheptanone oxime and ethyl 4-(4-(2-chlorophenyl)-1,2,3,6-tetrahydropyridin-1-yl)-n-butyrate, 3-(3-(4-(2-chlorophenyl)-1,2,3,6-tetrahydropyridin-1-yl)propyl)-5,6,7,8-tetrahydro-4H-cyclohepta[c]isoxazole is obtained.

EXAMPLE 64

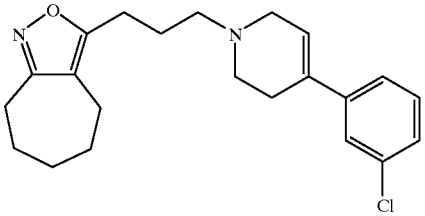

By the same reaction and treatment as in Example 48 using cycloheptanone oxime and ethyl 4-(4-(3-chlorophenyl)-1,2,3,6-tetrahydropyridin-1-yl-n-butyrate, 3-(3-(4-(3-chlorophenyl)-1,2,3,6-tetrahydropyridin-1-yl)propyl)-5,6,7,8-tetrahydro-4H-cyclohepta[c]isoxazole is obtained.

EXAMPLE 65

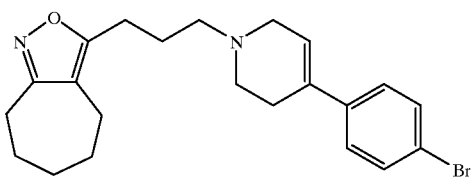

By the same reaction and treatment as in Example 48 using cycloheptanone oxime and ethyl 4-(4-(4-bromophenyl)-1,2,3,6-tetrahydropyridin-1-yl)-n-butyrate, 3-(3-(4-(4-bromophenyl)-1,2,3,6-tetrahydropyridin-1-yl)propyl)- 5,6,7,8-tetrahydro-4H-cyclohepta[c]isoxazole is obtained.

EXAMPLE 66

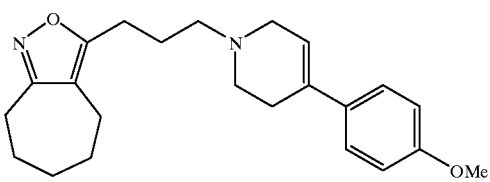

By the same reaction and treatment as in Example 48 using cycloheptanone oxime and ethyl 4-(4-(4-methoxyphenyl)-1,2,3,6-tetrahydropyridin-1-yl)-n-butyrate, 3-(3-(4-(4-methoxyphenyl)-1,2,3,6-tetrahydropyridin-1-yl)propyl)-5,6,7,8-tetrahydro-4H-cyclohepta[c]isoxazole is obtained.

EXAMPLE 67

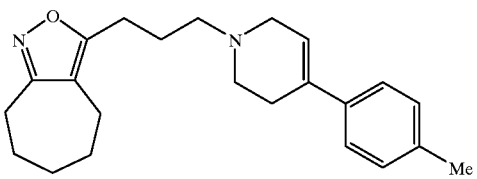

By the same reaction and treatment as in Example 48 using cycloheptanone oxime and ethyl 4-(4-(4-methylphenyl)-1,2,3,6-tetrahydropyridin-1-yl)-n-butyrate, 3-(3-(4-(4-methylphenyl)-1,2,3,6-tetrahydropyridin-1-yl)propyl)-5,6,7,8-tetrahydro-4H-cyclohepta[c]isoxazole is obtained.

EXAMPLE 68

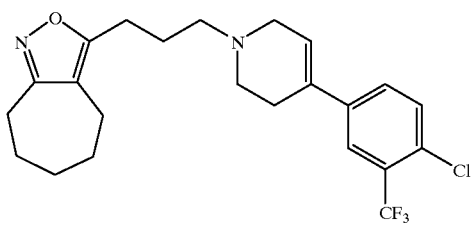

By the same reaction and treatment as in Example 48 using cycloheptanone oxime and ethyl 4-(4-(4-chloro-3-trifluoromethylphenyl)-1,2,3,6-tetrahydropyridin-1-yl)-n-butylate, 3-(3-(4-(4-chloro-3-trifluoromethylphenyl)- 1,2,3,6-tetrahydropyridin-1-yl)propyl)-5,6,7,8-tetrahydro-4H-cyclohepta[c]isoxazole is obtained.

EXAMPLE 69

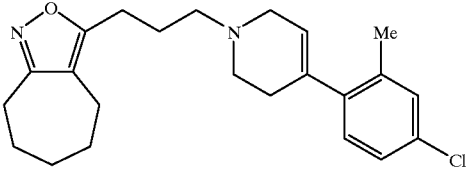

By the same reaction and treatment as in Example 48 using cycloheptanone oxime and ethyl 4-(4-(4-chloro-2-methylphenyl)-1,2,3,6-tetrahydropyridin-1-yl)-n-butyrate, 3-(3-(4-(4-chloro-2-methylphenyl)-1,2,3,6-tetrahydropyridin-1-yl)propyl)-5,6,7,8-tetrahydropyridin-4H-cyclohepta[c]isoxazole is obtained.

EXAMPLE 70

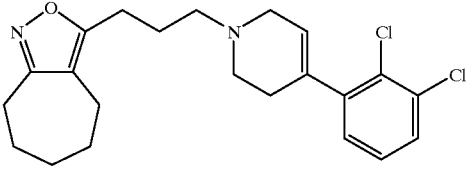

By the same reaction and treatment as in Example 48 using cycloheptanone oxime and ethyl 4-(4-(2,3-dichlorophenyl)-1,2,3,6-tetrahydropyridin-1-yl)-n-butyrate, 3-(3-(4-(2,3-dichlorophenyl)-1,2,3,6-tetrahydropyridin-1-yl)propyl)-5,6,7,8-tetrahydro-4H-cyclohepta[c]isoxazole is obtained.

EXAMPLE 71

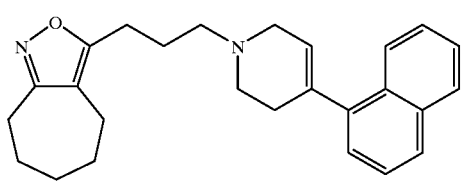

By the same reaction and treatment as in Example 48 using cycloheptanone oxime and ethyl 4-(4-(1-naphthyl)-1,2,3,6-tetrahydropyridin-1-yl)-n-butylate, 3-(3-(4-(1-naphthyl)-1,2,3,6-tetrahydropyridin-1-yl)propyl)-5,6,7,8-tetrahydro-4H-cyclohepta[c]isoxazole is obtained.

EXAMPLE 72

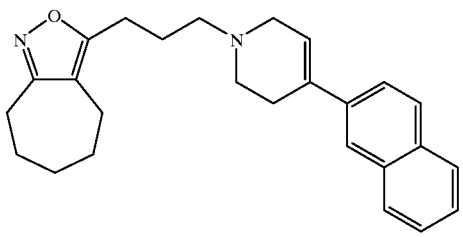

By the same reaction and treatment as in Example 48 using cycloheptanone oxime and ethyl 4-(4-(2-naphthyl)-1,2,3,6-tetrahydropyridin-1-yl)-n-butyrate, 3-(3-(4-(2-naphthyl)-1,2,3,6-tetrahydropyridin-1-yl)propyl)-5,6,7,8-tetrahydro-4H-cyclohepta[c]isoxazole is obtained.

EXAMPLE 73

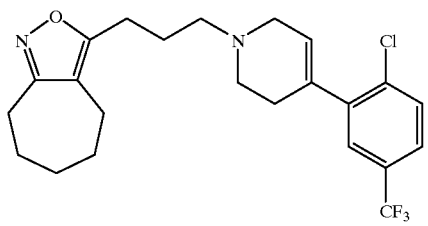

By the same reaction and treatment as in Example 48 using cycloheptanone oxime and ethyl 4-(4-(2-chloro-5-trifluoromethylphenyl)-1,2,3,6-tetrahydropyridin-1-yl)-n-butylate, 3-(3-(4-(2-chloro-5-trifluoromethylphenyl)-1,2,3,6-tetrahydropyridin-1-yl)propyl)-5,6,7,8-tetrahydro-4H-cyclohepta[c]isoxazole is obtained.

EXAMPLE 74

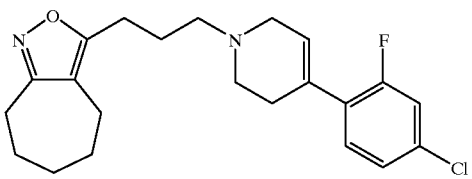

By the same reaction and treatment as in Example 48 using cycloheptanone oxime and ethyl 4-(4-(4-chloro-2-fluorophenyl)-1,2,3,6-tetrahydropyridin-1-yl)-n-butyrate, 3-(3-(4-(4-chloro-2-fluorophenyl)-1,2,3,6-tetrahydropyridin-1-yl)propyl)-5,6,7,8-tetrahydro-4H-cyclohepta[c]isoxazole is obtained.

EXAMPLE 75

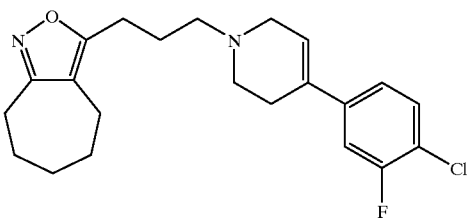

By the same reaction and treatment as in Example 48 using cycloheptanone oxime and ethyl 4-(4-(4-chloro-3-fluorophenyl)-1,2,3,6-tetrahydropyridin-1-yl)-n-butyrate, 3-(3-(4-(4-chloro-3-fluorophenyl)-1,2,3,6-tetrahydropyridin-1-yl)propyl)-5,6,7,8-tetrahydro-4H-cyclohepta[c]isoxazole is obtained.

EXAMPLE 76

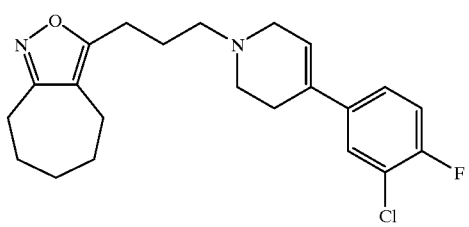

By the same reaction and treatment as in Example 48 using cycloheptanone oxime and ethyl 4-(4-(3-chloro-4-fluorophenyl)-1,2,3,6-tetrahydropyridin-1-yl)-n-butyrate, 3-(3-(4-(3-chloro-4-fluorophenyl)-1,2,3,6-tetrahydropyridin-1-yl)propyl)-5,6,7,8-tetrahydro-4H-cyclohepta[c]isoxazole is obtained.

EXAMPLE 77

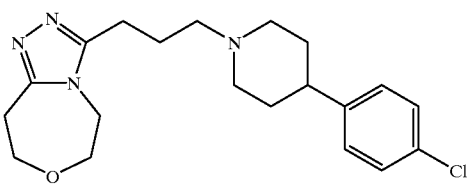

By the same reaction and treatment as in Example 1 using 5-methoxy-2,3,6,7-tetrahydro[1,4]oxazepine and 3-(4-(4-chlorophenyl)piperidin-1-yl)propylcarbohydrazide, 3-(3-(4-(4-chlorophenyl)piperidin-1-yl)propyl)-5,6,8,9-tetrahydro-1,2,4-triazolo[4,3-d][1,4]oxazepine is obtained.

EXAMPLE 78

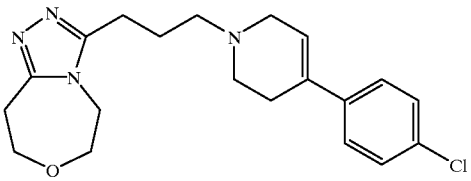

By the same reaction and treatment as in Example 1 using 5-methoxy-2,3,6,7-tetrahydro[1,4]oxazepine and 3-(4-(4- chlorophenyl)-1,2,3,6-tetrahydropyridin-1-yl)propylcarbohydrazide, 3-(3-(4-(4-chlorophenyl)-1,2,3,6-tetrahydropyridin-1-yl)propyl)-5,6,8,9-tetrahydro-1,2,4-triazolo[4,3-d][1,4]oxazepine is obtained.

EXAMPLE 79

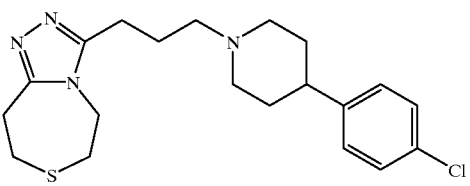

By the same reaction and treatment as in Example 1 using 5-methoxy-2,3,6,7-tetrahydro[1,4]thiazine and 3-(4-(4-chlorophenyl)piperidin-1-yl)propylcarbohydrazide, 3-(3-(4-(4-chlorophenyl)piperidin-1-yl)propyl)-5,6,8,9-tetrahydro-1,2,4-triazolo[4,3-d][1,4]thiazine is obtained.

EXAMPLE 80

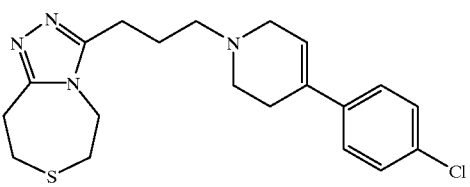

By the same reaction and treatment as in Example 1 using 5-methoxy-2,3,6,7-tetrahydro[1,4]thiazine and 3-(4-(4-chlorophenyl)-1,2,3,6-tetrahydropyridin-1-yl)propylcarbohydrazide, 3-(3-(4-(4-chlorophenyl)-1,2,3,6-tetrahydropyridin-1-yl)propyl)-5,6,8,9-tetrahydro-1,2,4-triazolo[4,3-d][1,4]thiazine is obtained.

EXAMPLE 81

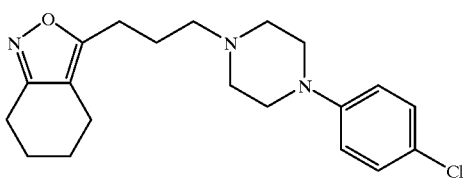

By the same reaction and treatment as in Example 48 using cyclohexanone oxime and ethyl 4-(4-(4-chlorophenyl)piperazin-1-yl)-n-butylate, 3-(3-(4-(4-chlorophenyl)piperazin-1-yl)propyl)-4,5,6,7-tetrahydrobenzo[c]isoxaole is obtained.

EXAMPLE 82

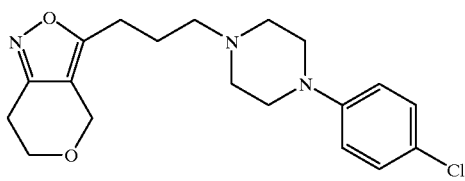

By the same reaction and treatment as in Example 48 using tetrahydro-4H-pyran-4-one oxime and ethyl 4-(4-(4-chlorophenyl)piperazin-1-yl)-n-butylate, 3-(3-(4-(4-chlorophenyl)piperazin-1-yl)propyl)-6,7-dihydro-4H-pyrano[4,3-c]isoxazole is obtained.

EXAMPLE 83

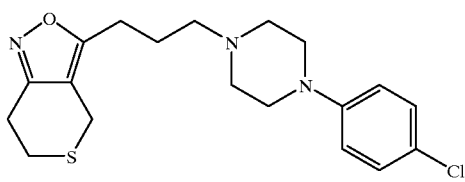

By the same reaction and treatment as in Example 48 using tetrahydro-4H-thiopyran-4-one oxime and ethyl 4-(4-(4-chlorophenyl)piperazin-1-yl)-n-butyrate, 3-(3-(4-(4chlorophenyl)piperazin-1-yl)propyl)-6,7-dihydro-4H-thiopyrano[4,3-c]isoxazole is obtained.

EXAMPLE 84

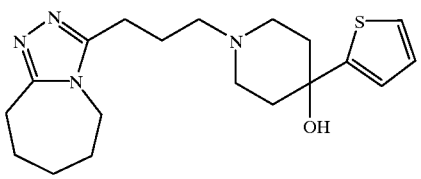

To a solution (30 ml) of 1-aza-2-methylthio-1-cycloheptene (5.74 g) in butanol was added 3-(4-(2-thienyl)-4-hydroxypiperidin-1-yl)propylcarbohydrazide (8.5 g) with stirring, and the mixture was refluxed under heating for 3 hours. After the completion of the reaction, the solvent was evaporated under reduced pressure, and the obtained residue was recrystallized from ethyl acetate to give 10 g of 3-(3-(4-(2-thienyl)-4-hydroxypiperidin-1-yl)propyl)-6,7,8,9-tetrahydro-5H-1,2,4-triazolo[4,3-a]azepine, m.p. 162–163° C.

EXAMPLE 85

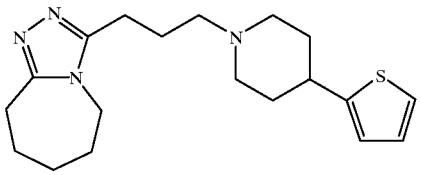

By the same reaction and treatment as in Example 1 using 1-aza-2-methoxy-1-cycloheptene and 3-(4-(2-thienyl)

piperidin-1-yl)propylcarbohydmazide, 3-(3-(4-(2-thienyl) piperidin-1-yl)propyl)-6,7,8,9-tetrahydro-5H-1,2,4-triazolo [4,3-a]azepine is obtained.

EXAMPLE 86

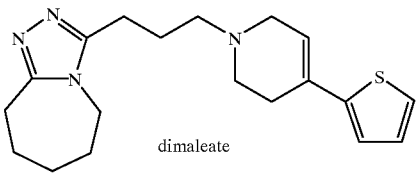

dimaleate

By the same reaction and treatment as in Example 1 using 1-aza-2-methoxy-1-cycloheptene and 3-(4-(2-thienyl)-1,2,3, 6-tetrahydropyridin-1-yl)propylcarbohydrazide and then by a conventional treatment using maleic acid, 3-(3-(4-(2-thienyl)-1,2,3,6-tetrahydropyridin-1-yl)propyl)-6,7,8,9-tetrahydro-5H-1,2,4-triazolo[4,3-a]azepine dimaleate was obtained, m.p. 166–167° C.

EXAMPLE 87

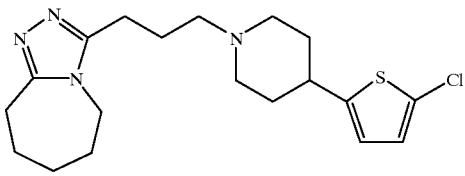

By the same reaction and treatment as in Example 1 using 1-aza-2-methoxy-1-cycloheptene and 3-(4-(5-chloro-2-thienyl)piperidin-1-yl)propylcarbohydrazide, 3-(3-(4-(5-chloro-2-thienyl)piperidin-1-yl)propyl)-6,7,8,9-tetrahydro-5H-1,2,4-triazolo[4,3-a]azepine is obtained.

EXAMPLE 88

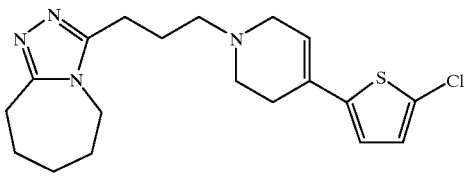

By the same reaction and treatment as in Example 1 using 1-aza-2-methoxy-1-cycloheptene and 3-(4-(5-chloro-2-thienyl)-1,2,3,6-tetrahydropyridin-1-yl) propylcarbohydrazide, 3-(3-(4-(5-chloro-2-thienyl)-1,2,3,6-tetrahydropyridin-1-yl)propyl)-6,7,8,9-tetrahydro-5H-1,2,4-triazolo[4,3-a]azepine is obtained.

EXAMPLE 89

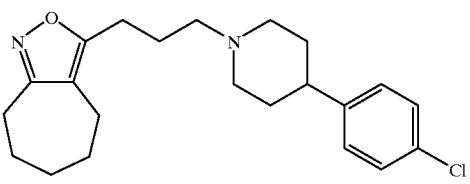

By the same reaction and treatment as in Example 48 using cycloheptanone oxime and ethyl 4-(4-(4-chlorophenyl)piperidin-1-yl)-n-butyrate, 3-(3-(4-(4-chlorophenyl)piperidin-1-yl)propyl)-5,6,7,8-tetrahydro-4H-cyclohepta[c]isoxazole is obtained.

EXAMPLE 90

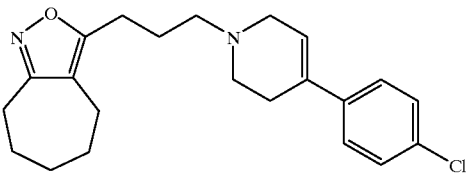

By the same reaction and treatment as in Example 48 using cycloheptanone oxime and ethyl 4-(4-(4-chlorophenyl)-1,2,3,6-tetrahydropyridin-1-yl)-n-butyrate, 3-(3-(4-(4-chlorophenyl)-1,2,3,6-tetrahydropyridin-1-yl) propyl)-5,6,7,8-tetrahydro-4H-cyclohepta[c]isoxazole is obtained.

EXAMPLE 91

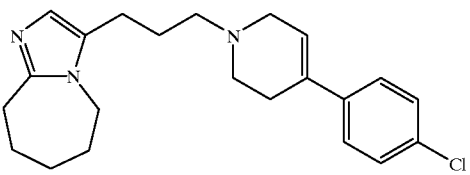

To a solution of 6,7,8,9-tetrahydro-5H-imidazo[1,2-a] azepine in acetonitrile are added aqueous formaldehyde solution and 2,2-dimethyl-1,3-dioxane-4,6-dione with stirring and the mixture is heated for 4 hours. After the completion of the reaction, the reaction mixture is poured into water and the mixture is extracted with chloroform, washed with water, and dried over magnesium sulfate. The solution is concentrated under reduced pressure and the resulting 2,2-dimethyl-5-(6,7,8,9-tetrahydro-5H-imidazo[1, 2-a]azepin-3-ylmethyl)-1,3-dioxane-4,6-dione is dissolved in pyridine with sting. Water and copper powder are added and the mixture is refluxed under heating for 3 hours. After the completion of the reaction, the reaction mixture is filtered while it is hot and the solvent is evaporated under reduced pressure to give 3-(6,7,8,9-tetrahydro-5H-imidazo [1,2-a]azepin-3-yl)propionic acid. To a solution of this compound in dimethylformamide are added 4-(4-chlorophenyl) piperidine, triethylamine and cyanophosphonic acid diester and the mixture is stirred at room temperature. After the completion of the reaction, the reaction mixture is poured into water and the mixture is extracted with chloroform, washed with water, and dried over magnesium sulfate. The solution is concentrated under reduced pressure and the resulting 1-(4-(4-chlorophenyl)piperidin-1-yl)-3-(6,7,8,9-tetrahydro-5H-imidazo[1,2-a]azepin-3-yl)propan-1-one is dissolved in tetrahydrofuran and lithium aluminum hydride is added under ice-cooling with stirring and the mixture is stirred at room temperature for 1 hour. After the completion of the reaction, the reaction mixture is poured into water and the mixture is extracted with chloroform, washed with water, and dried over magnesium sulfate. The solution is concentrated under reduced pressure and the obtained residue is subjected to silica gel column chromatography to give 3-(3-(4-(4-chlorophenyl)piperidin-1-yl)propyl)-6,7,8,9-tetrahydro-5H-imidazo[1,2-a]azepine.

EXAMPLE 92

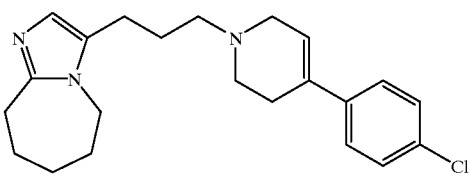

By the same reaction and treatment as in Example 91 using 6,7,8,9-tetrahydro-5H-imidazo[1,2-a]azepine, 2,2-dimethyl-1,3-dioxane-4,6-dione and 4-(4chlorophenyl)-1,2,3,6-tetrahydropyridine, 3-(3-(4-(4-chlorophenyl)-1,2,3,6-tetrahydropyridin-1-yl)propyl)-6,7,8,9-tetrahydro-5H-imidazo[1,2-a]azepine is obtained.

EXAMPLE 93

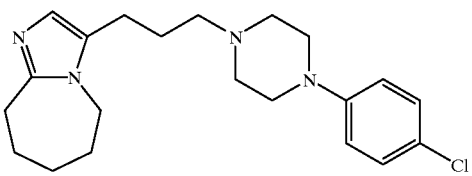

By the same reaction and treatment as in Example 91 using 6,7,8,9-tetrahydro-5H-imidazo[1,2-a]azepine, 2,2-dimethyl-1,3-dioxane-4,6-dione and 1-(4-chlorophenyl)piperazine, 3-(3-(4-(4-chlorophenyl)piperazin-1-yl)propyl)-6,7,8,9-tetrahydro-5H-imidazo[1,2-a]azepine is obtained.

EXAMPLE 94

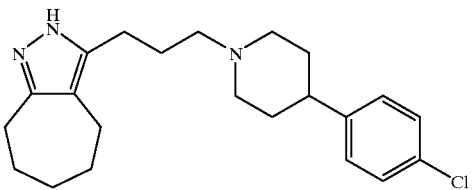

To a solution of 1-morpholino-1-cycloheptene in chloroform are added triethylamine and 4-(4-(4-chlorophenyl)piperidin-1-yl)butanoyl chloride with stirring and the mixture is stirred at room temperature. After the completion of the reaction, the reaction mixture is poured into water and extracted with chloroform, and the extract is washed with water and dried over magnesium sulfate. The solution is concentrated under reduced pressure. To a mixed solution of the obtained 2-(4-(4-(4-chlorophenyl)piperidin-1-yl)butanoyl)cycloheptanone in chloroform and methanol is added hydrazine monohydrate with stirring and the mixture is stirred at room temperature for 6 hours. After the completion of the reaction, the reaction mixed is poured into water and the mixture is extracted with chloroform, washed with water and dried over magnesium sulfate. The solution is concentrated under reduced pressure and the obtained residue is subjected to silica gel column chromatography to give 3-(3-(4-(4-chlorophenyl)piperidin-1-yl)propyl)-2,4,5,6,7,8-hexahydrocycloheptapymzole.

EXAMPLE 95

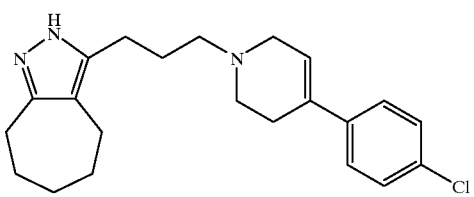

By the same reaction and treatment as in Example 94 using 1-morpholino-1-cycloheptene and 4-(4-(4-chlorophenyl)-1,2,3,6-tetrahydropyridin-1-yl)butanoyl chloride, 3-(3-(4-(4-chlorophenyl)-1,2,3,6-tetrahydropyridin-1-yl)propyl)-2,4,5,6,7,8-hexahydrocycloheptapymzole is obtained.

EXAMPLE 96

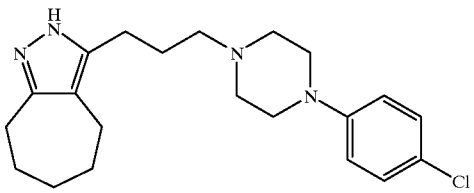

By the same reaction and treatment as in Example 94 using 1-morpholino-1-cycloheptene and 4-(4-(4-chlorophenyl)piperazin-1-yl)butanoyl chloride, 3-(3-(4-(4-chlorophenyl)piperazin-1-yl)propyl)-2,4,5,6,7,8-hexahydrocycloheptapymzole is obtained.

EXAMPLE 97

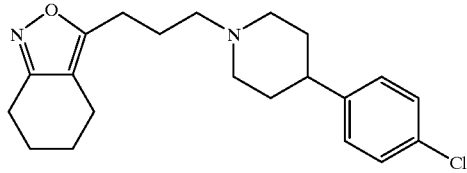

By the same reaction and treatment as in Example 48 using cyclohexanone oxime and ethyl 4-(4-(4-chlorophenyl)piperidin-1-yl)-n-butylate, 3-(3-(4-(4-chlorophenyl)piperidin-1-yl)propyl)-4,5,6,7-tetrahydrobenzo[c]isoxazole is obtained.

EXAMPLE 98

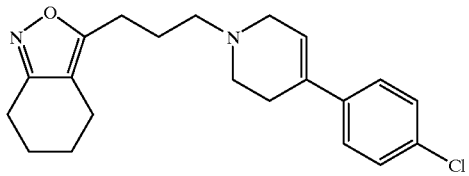

By the same reaction and treatment as in Example 48 using cyclohexanone oxime and ethyl 4-(4-(4-chlorophenyl)-1,2,3,6-tetrahydropyridin-1-yl)-n-butyrate, 3-(3-(4-(4-chlorophenyl)-1,2,3,6-tetrahydropyridin-1-yl)propyl)-4,5,6,7-tetrahydrobenzo[c]isoxazole is obtained.

EXAMPLE 99

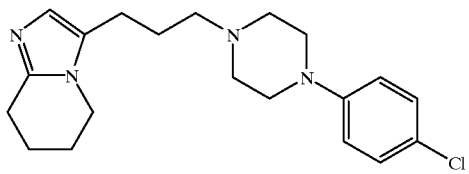

To a solution of 3-(imidazo[1,2-a]pyridin-3-yl)propionic acid (4 g) synthesized according to the method described in Japanese Patent Unexamined Publication No. 189179/1983, 1-(4-chlorophenyl)piperazine hydrochloride (4.9 g) and triethylamine (5.9 ml) in dimethylformamide was added dropwise diethyl cyanophosphate (3.8 ml) under ice-cooling with stirring, and the mixture was stirred for 3 hours. After the completion of the reaction, the reaction mixture was concentrated, extracted with chloroform, washed with water and dyed over magnesium sulfate. The solution was concentrated under reduced pressure, and lithium aluminum hydride was added to a solution of the obtained 4-(4-chlorophenyl)-1-(3-(imidazo[1,2-a]pyridin-3-yl)propionyl)piperazine in tetrahydrofuran under ice-cooling with stirring, and the mixture was stirred at room temperature for 1 hour. After the completion of the reaction, the reaction mixture was treated with a mixed solvent of water-tetrahydrofuran and filtered through celite. The filtrate was concentrated under reduced pressure the obtained residue was subjected to silica gel column chromatography to give 3-(3-(4-(4-chlorophenyl)piperazin-1-yl)propyl)imidazo[1,2-a]pyridine. This compound was dissolved in a mixture of ethanol (20 ml) and conc. hydrochloric acid (20 ml) and reduced in the presence of 10% palladium-carbon (1 g) in an autoclave at 70° C. and 50 atm. After the completion of the reaction, the reaction mixture was filtered through celite. The filtrate was concentrated under reduced pressure and the obtained residue was subjected to silica gel column chromatography to give 3-(3-(4-(4-chlorophenyl)piperazin-1-yl)propyl)-5,6,7,8-tetrahydroimidazo[1,2-a]pyridine, m.p. 95–97° C. (m.p. as oxalate).

EXAMPLE 100

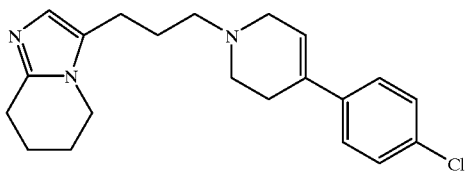

In the same manner as in Example 99 except that 4-(4-chlorophenyl)-1,2,3,6-tetrahydropyridine is used instead of 1-(4-chlorophenyl)piperazine, 3-(3-(4-(4chlorophenyl)-1,2,3,6-tetrahydropyridin-1-yl)propyl)-5,6,7,8-tetrahydroimidazo[1,2-a]pyridine is obtained.

EXAMPLE 101

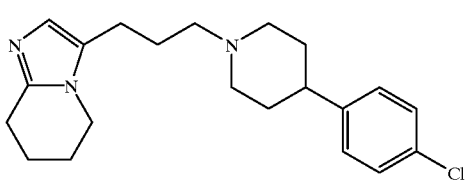

In the same manner as in Example 99 except that 4-(4-chlorophenyl)piperidine is used instead of 1-(4 chlorophenyl)piperazine, 3-(3-(4-(4-chlorophenyl)piperidin-1-yl)propyl)-5,6,7,8-tetrahydroimidazo[1,2-a]pyridine is obtained.

EXAMPLE 102

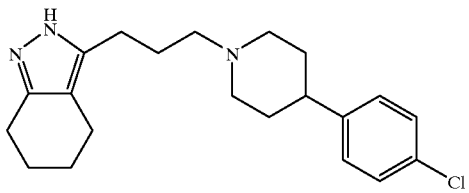

To a solution of 3-(4,5,6,7-tetrahydro-2H-indazol-3-yl)propionic acid (0.7 g) obtained in Starting Material Synthesis Example 1,4-(4-chlorophenyl)piperidine (0.7 g) and triethylamine (1.7 ml) in dimethylformamide (10 ml) was added dropwise diethyl cyanophosphate (0.7 ml) with stirring, and the mixture was stirred for 3 hours. After the completion of the reaction, the reaction mixture was concentrated, extracted with chloroform, washed with water, and dried over magnesium sulfate. The solution was concentrated under reduced pressure, and lithium aluminum hydride was added to a solution of the obtained 4-(4-chlorophenyl)-1-(3-(4,5,6,7-tetrahydro-2H-indazol-3-yl)propionyl)piperidine in tetrahydrofuran under ice-cooling with stirring, which was followed by stirring at room temperature for 1 hour. After the completion of the reaction, the reaction mixture is treated with a mixed solvent of water-tetrahydrofuran and filtered through celite. The filtrate is concentrated under reduced pressure, the obtained residue is subjected to silica gel column chromatography to give 3-(3-(4-(4-chlorophenyl)piperidin-1-yl)propyl)-4,5,6,7-tetrahydro-2H-indazole.

EXAMPLE 103

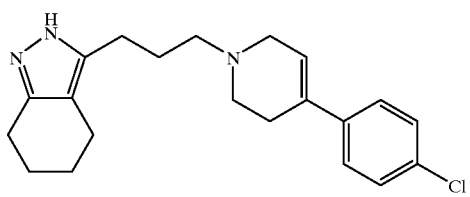

In the same manner as in Example 102 using 4-(4-chlorophenyl)-1,2,3,6-tetrahydropyridine instead of 4-(4-chlorophenyl)piperidine, 3-(3-(4-(4-chlorophenyl)-1,2,3,6-tetrahydropyridin-1-yl)propyl)-4,5,6,7-tetrahydro-2H-indazole was obtained.

$^1$H-NMR(CDCl$_3$)δ: 1.67–1.85(4H,m), 1.89(2H,tt,J=6.7 Hz), 2.35–2.47(2H,m), 2.52(2H,t,J=7 Hz), 2.53–2.71(6H, m), 2.71(2H,t,J=6 Hz), 3.12–3.22(2H,m), 7.21–7.36(4H,m)

EXAMPLE 104

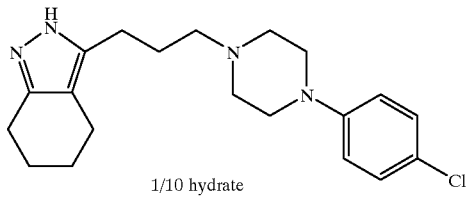

1/10 hydrate

In the same manner as in Example 102 using 1-(4-chlorophenyl)piperazine instead of 4-(4-chlorophenyl)piperidine, 3-(3-(4-(4-chlorophenyl)piperazin-1-yl)propyl)-4,5,6,7-tetrahydro-2H-indazole 1/10 hydrate was obtained, m.p. 109–111° C.

EXAMPLE 105

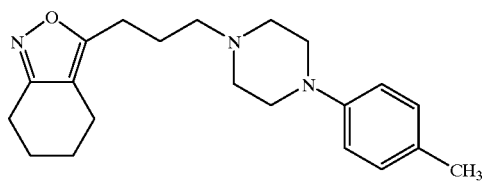

By the same reaction and treatment as in Example 48 using cyclohexanone oxime and ethyl 4-(4-(4-methylphenyl)piperazin-1-yl)-n-butyrate, 3-(3-(4-(4-methylphenyl)piperazin-1-yl)propyl)-4,5,6,7-tetrahydrobenzo[c]isoxazole is obtained.

EXAMPLE 106

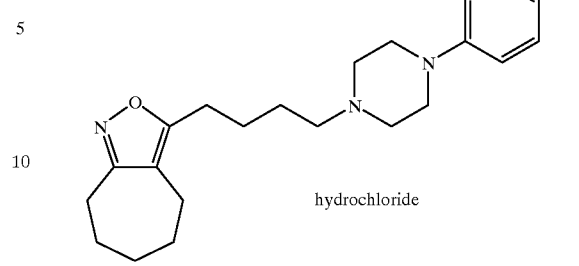

hydrochloride

By the same reaction and treatment as in Example 48 using cycloheptanone oxime and ethyl 5-(4-(4-fluorophenyl)piperazin-1-yl)-n-valerate and then by a conventional treatment using hydrochloric acid, 3-(4-(4-(4-fluorophenyl)piperazin-1-yl)butyl)-5,6,7,8-tetrahydro-4H-cyclohepta[c]isoxazole hydrochloride was obtained, m.p. 174–175° C.

EXAMPLE 107

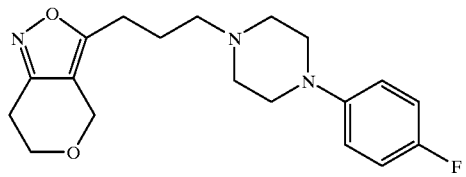

By the same reaction and treatment as in Example 48 using tetrahydro-4H-pyran-4-one oxime and ethyl 4-(4-(4-fluorophenyl)piperazin-1-yl)-n-butyrate, 3-(3-(4-(4-fluorophenyl)piperazin-1-yl)propyl)-6,7-dihydro-4H-pyrano[4,3-c]isoxazole is obtained.

EXAMPLE 108

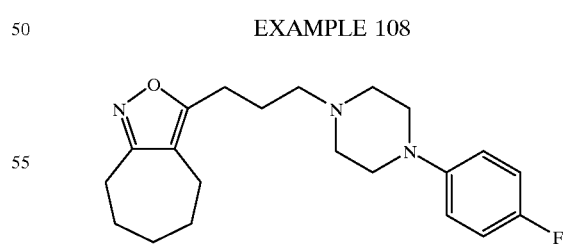

By the same reaction and treatment as in Example 48 using cycloheptanone oxime and ethyl 4-(4-(4-fluorophenyl)piperazin-1-yl)-n-butyrate, 3-(3-(4-(4-fluorophenyl)piperazin-1-yl)propyl)-5,6,7,8-tetrahydro-4H-cyclohepta[c]isoxazole is obtained.

EXAMPLE 109

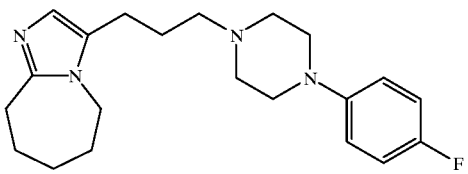

By the same reaction and treatment as in Example 91 using 6,7,8,9-tetrahydro-5H-imidazo[1,2-a]azepine, 2,2-dimethyl-1,3-dioxane-4,6-dione and 1-(4-fluorophenyl)piperazine, 3-(3-(4-(4-fluorophenyl)piperazin-1-yl)propyl)-6,7,8,9-tetrahydro-5H-imidazo[1,2-a]azepine is obtained.

EXAMPLE 110

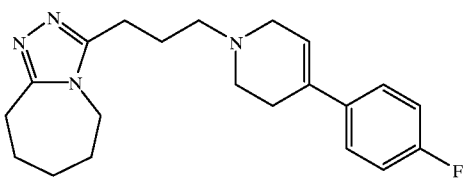

By the same reaction and treatment as in Example 1 using 1-aza-2-methoxy-1-cycloheptene and 3-(4-(4-fluorophenyl)-1,2,3,6-tetrahydropyridin-1-yl) propylcarbohydrazide, 3-(3-(4-(4-fluorophenyl)-1,2,3,6-tetrahydropyridin-1-yl)propyl)-6,7,8,9-tetrahydro-5H-1,2,4-triazolo[4,3-a]azepine is obtained.

EXAMPLE 111

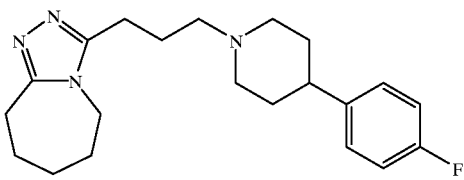

By the same reaction and treatment as in Example 1 using 1-aza-2-methoxy-1-cycloheptene and 3-(4-(4-fluorophenyl)piperidin-1-yl)propylcarbohydrazide, 3-(3-(4-(4-fluorophenyl)piperidin-1-yl)propyl)-6,7,8,9-tetrahydro-5H-1,2,4-triazolo[4,3-a]azepine is obtained.

EXAMPLE 112

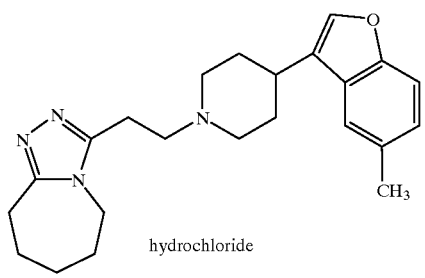

hydrochloride

By the same reaction and treatment as in Example 1 using 1-aza-2-methoxy-1-cycloheptene and 2-(4-(5-methylbenzo[b]furan-3-yl)piperidin-1-yl)ethylcarbohydrazide and then by a conventional treatment using hydrochloric acid, 3-(2-(4-(5-methylbenzo[b]furan-3-yl)piperidin-1-yl)ethyl)-6,7,8,9-tetrahydro-5H-1,2,4-triazolo[4,3-a]azepine hydrochloride was obtained, m.p. 226° C. (decomposition).

EXAMPLE 113

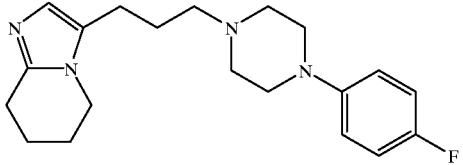

In the same manner as in Example 99 except that 1-(4-fluorophenyl)piperazine was used instead of 1-(4-chlorophenyl)piperazine, 3-(3-(4-(4-fluorophenyl)piperazine-1-yl)propyl)-5,6,7,8-tetrahydroimidazo[1,2-a]pyridine was obtained, m.p. 106–108° C.

EXAMPLE 114

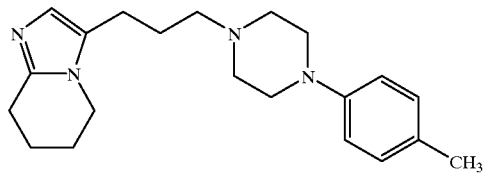

In the same manner as in Example 99 except that 1-(4-methylphenyl)piperazine is used instead of 1-(4-chlorophenyl)piperazine, 3-(3-(4-(4-methylphenyl)piperazin-1-yl)propyl)-5,6,7,8-tetrahydroimidazo[1,2-a]pyridine is obtained.

EXAMPLE 115

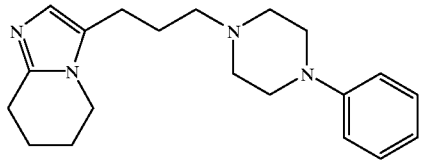

In the same manner as in Example 99 except that 1-phenylpiperazine is used instead of 1-(4-chlorophenyl)piperazine, 3-(3-(4-phenylpiperazin-1-yl)propyl)-5,6,7,8-tetrahydroimidazo[1,2-a]pyridine is obtained.

EXAMPLE 116

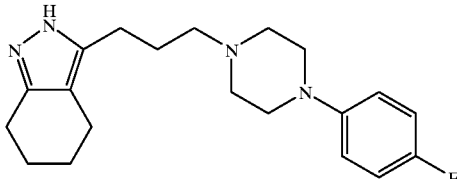

In the same manner as in Example 102 except that 1-(4-fluorophenyl)piperazine was used instead of 4-(4- chlorophenyl)piperidine, 3-(3-(4-(4-fluorophenyl)piperazin-1-yl)propyl)-4,5,6,7-tetrahydro-2H-indazole was obtained, m.p. 106–108° C. The compound was converted to an acid addition salt of maleic acid to give 3-(3-(4-(4-fluorophenyl)piperazin-1-yl)propyl)-4,5,6,7-tetrahydro-2H-indazole maleate, m.p. 141–142° C. The compound was converted to an acid addition salt of hydrochloric acid to give 3-(3-(4-(4-fluorophenyl)piperazin-1-yl)propyl)-4,5,6,7-tetrahydro-2H-indazole hydrochloride, m.p. 210–211 ° C.

EXAMPLE 117

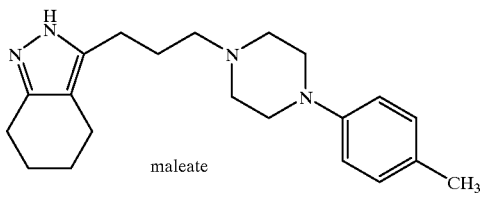

maleate

In the same manner as in Example 102 except that 1-(4-methylphenyl)piperazine was used instead of 4-(4-chlorophenyl)piperidine and then by a conventional treatment using maleic acid, 3-(3-(4-(4-methylphenyl)piperazin-1-yl)propyl)-4,5,6,7-tetrahydro-2H-indazole maleate was obtained, m.p. 144–146° C.

EXAMPLE 118

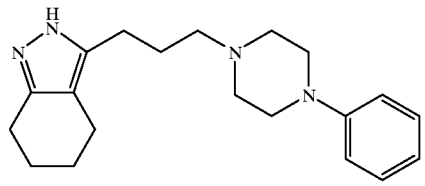

In the same manner as in Example 102 except that 1-phenylpiperazne was used instead of 4-(4-chlorophenyl)piperidine, 3-(3-(4-phenylpiperazin-1-yl)propyl)4,5,6,7-tetrahydro-2H-indazole was obtained, m.p. 92–94° C. The compound was converted to an acid addition salt of maleic acid to give 3-(3-(4-phenylpiperazin-1-yl)propyl)-4,5,6,7-tetrahydro-2H-indazole maleate, m.p. 123–125° C.

EXAMPLE 119

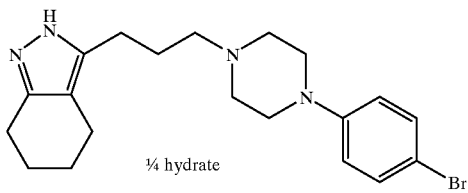

¼ hydrate

In the same manner as in Example 102 except that 1-(4-bromophenyl)piperazine was used instead of 4-(4-chlorophenyl)piperidine, 3-(3-(4-(4-bromophenyl)piperazin-1-yl)propyl)-4,5,6,7-tetrahydro-2H-indazole 1/4 hydrate was obtained, m.p. 145–147° C.

EXAMPLE 120

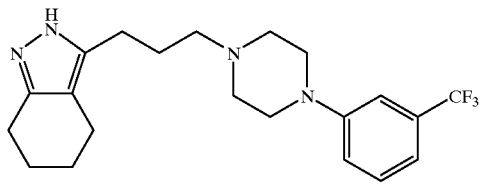

In the same manner as in Example 102 except that 1-(3-trifluoromethyl-phenyl)piperazine was used instead of 4-(4-chlorophenyl)piperidine, 3-(3-(4(3-trifluoromethylphenyl)piperazin-1-yl)propyl)-4,5,6,7-tetrahydro-2H-indazole was obtained.

$^1$H-NMR(CDCl$_3$)δ: 1.68–1.94(6H,m), 2.36–2.53(4H,m), 2.58–2.74(8H,m), 3.27(4H,t,J=5 Hz), 7.01–7.17(3H,m), 7.33(1H,t,J=8 Hz)

EXAMPLE 121

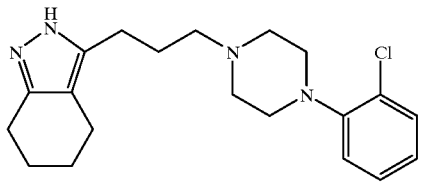

In the same manner as in Example 102 except that 1-(2-chlorophenyl)piperazine was used instead of 4-(4-chlorophenyl)piperidine, 3-(3-(4-(2-chlorophenyl)piperazin-1-yl)propyl)-4,5,6,7-tetrahydro-2H-indazole was obtained.

$^1$H-NMR(CDCl$_3$)δ: 1.66–1.92(6H,m), 2.32–2.45(4H,m), 2.55–2.65(8H,m), 3.12–3.20(4H,m), 6.98(1H,dt,J=1.8 Hz), 7.07(1H,dd,J=2.8 Hz), 7.21(1H,dt,J=1.8 Hz), 7.34(1H,dd,J=1.8 Hz)

EXAMPLE 122

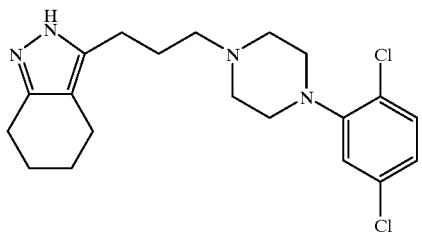

In the same manner as in Example 102 except that 1-(2,5-dichlorophenyl)piperazine was used instead of 4-(4-chlorophenyl)piperidine, 3-(3-(4-(2,5-dichlorophenyl)piperazin-1-yl)propyl)-4,5,6,7-tetrahydro-2H-indazole was obtained.

$^1$H-NMR(CDCl$_3$)δ: 1.65–1.90(6H,m), 2.32–2.44(4H,m), 2.52–2.73(8H,m), 3.08–3.22(4H,m), 6.95(1H,dd,J=2.9 Hz), 7.02(1H,d,J=3 Hz), 7.25(1H,d,J=9 Hz)

EXAMPLE 123

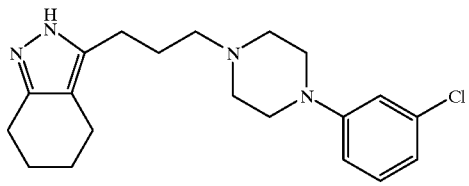

In the same manner as in Example 102 except that 1-(3-chlorophenyl)piperazine was used instead of 4-(4-chlorophenyl)piperidine, 3-(3-(4-(3-chlorophenyl)piperazin-1-yl)propyl)4,5,6,7-tetrahydro-2H-indazole was obtained.

$^1$H-NMR(CDCl$_3$)δ: 1.68–1.94(6H,m), 2.38–2.55(4H,m), 2.58–2.65(8H,m), 3.23–3.27(4H,m), 6.79(1H,dt,J=2.8 Hz), 6.87(1H,d,J=2 Hz), 7.15(1H,t,J=8 Hz)

EXAMPLE 124

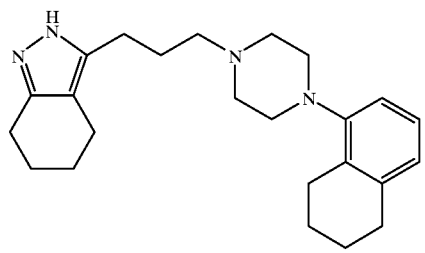

In the same manner as in Example 102 except that 1-(5,6,7,8-tetrahydronaphthalen-1-yl)piperazine was used instead of 4-(4-chlorophenyl)piperidine, 3-(3-(4-(5,6,7,8-tetrahydronaphthalen-1-yl)piperazin-1-yl)propyl)-4,5,6,7-tetrahydro-2H-indazole was obtained.

$^1$H-NMR(CDCl$_3$)δ: 1.75–1.92(10H,m), 2.41–2.52(4H,m), 2.62–2.78(12H,m), 2.94–2.97(4H,m), 6.83(1H,d,J=7 Hz), 6.89(1H,d,J=7 Hz), 7.08(1H,t,J=8 Hz)

EXAMPLE 125

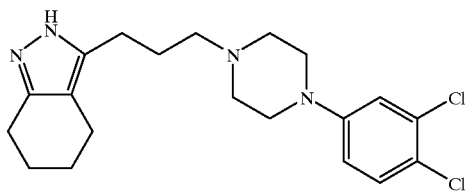

In the same manner as in Example 102 except that 1-(3,4-dichlorophenyl)piperazine was used instead of 4-(4-chlorophenyl)piperidine, 3-(3-(4-(3,4-dichlorophenyl)piperazine-1-yl)propyl)-4,5,6,7-tetrahydro-2H-indazole was obtained.

$^1$H-NMR(CDCl$_3$)δ: 1.68–1.94(6H,m), 2.33–2.51(4H,m), 2.53–2.70(8H,m), 3.19(4H,t,J=5 Hz), 6.72(1H,dd,J=3.9 Hz), 6.94(1H,d,J=3 Hz), 7.25(1H,d,J=9 Hz)

EXAMPLE 126

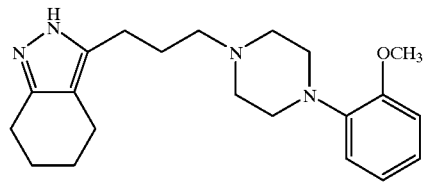

In the same manner as in Example 102 except that 1-(2-methoxyphenyl)piperazine was used instead of 4-(4-chlorophenyl)piperidine, 3-(3-(4-(2-methoxyphenyl)piperazin-1-yl)propyl)-4,5,6,7-tetrahydro-2H-indazole was obtained.

$^1$H-NMR(CDCl$_3$)δ: 1.68–1.90(6H,m), 2.38–2.50(4H,m), 2.55–2.68(8H,m), 3.19–3.25(4H,m), 3.86(3H,s), 6.84–7.04 (4H,m)

EXAMPLE 127

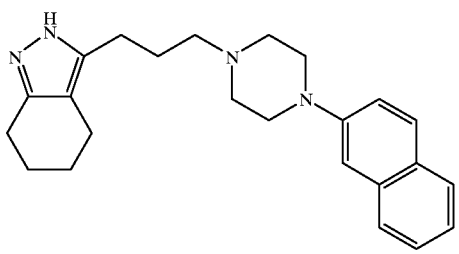

In the same manner as in Example 102 except that 1-(2-naphthyl)piperazine obtained in Starting Material Synthesis Example 2 was used instead of 4-(4-chlorophenyl)piperidine, 3-(3-(4-(2-naphthyl)piperazin-1-yl)propyl)-4,5,6,7-tetrahydro-2H-indazole was obtained.

$^1$H-NMR(CDCl$_3$)δ: 1.73–2.10(6H,m), 2.41–2.52(4H,m), 2.55–2.70(8H,m), 3.10–3.25(4H,m), 7.13(1H,d,J=2 Hz), 7.24–7.31(2H,m), 7.37–7.42(1H,m), 7.73(3H,t,J=8 Hz)

EXAMPLE 128

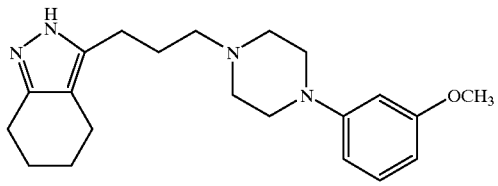

In the same manner as in Example 102 except that 1-(3-methoxyphenyl)piperazine was used instead of 4-(4-chlorophenyl)piperidine, 3-(3-(4-(3-methoxyphenyl)piperazin-1-yl)propyl)-4,5,6,7-tetrahydro-2H-indazole was obtained.

$^1$H-NMR(CDCl$_3$)δ: 1.70–1.91(6H,m), 2.40–2.48(4H,m), 2.59–2.66(8H,m),3.21–3.26( 4H,m), 3.78(3H,s), 6.41(1H, dd,J=2 Hz, 8 Hz), 6.46(1H,t,J=2 Hz), 6.53(1H,dd,J=2 Hz, 8 Hz), 7.16(1H,t,J=8 Hz)

EXAMPLE 129

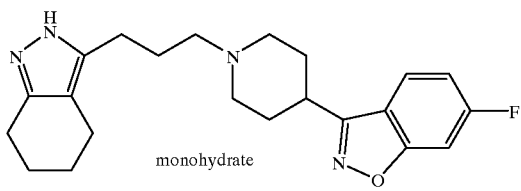

monohydrate

In the same manner as in Example 102 except that 4-(6-fluoro-1,2-benzoisoxazol-3-yl)piperidine was used instead of 4-(4-chlorophenyl)piperidine, 3-(3-(4-(6-fluoro-1,2-benzoisoxazol-3-yl)piperidin-1-yl)propyl)-4,5,6,7-tetrahydro-2H-indazole monohydrate was obtained, m.p. 124–126° C.

EXAMPLE 130

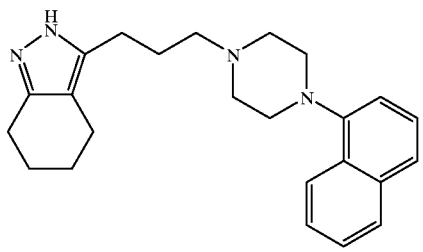

In the same manner as in Example 102 except that 1-(1-naphthyl)piperazine was used instead of 4-(4-chlorophenyl)piperidine, 3-(3-(4-(1-naphthyl)piperazin-1-yl)propyl)-4,5,6,7-tetrahydro-2H-indazole was obtained.

$^1$H-NMR(CDC$_3$)δ: 1.65–1.91(6H,m), 2.35–2.52(4H,m), 2.55–2.70(8H,m), 3.00–3.12(4H,m), 7.14(1H,d,J=7 Hz), 7.40(1H,t,J=8 Hz), 7.45–7.50(2H,m), 7.58(1H,d,J=8 Hz), 7.81–7.85(1H,m), 8.12–8.15(1H,m)

EXAMPLE 131

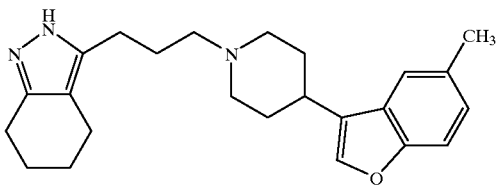

In the same manner as in Example 102 except that 1-(5-methylbenzo-[b]furan-3-yl)piperidine was used instead of 4-(4-chlorophenyl)piperidine, 3-(3-(4-(5-methylbenzo[b]furan-3-yl)piperidin-1-yl)propyl)-4,5,6,7-tetrahydro-2H-indazole was obtained.

$^1$H-NMR(CDCl$_3$)δ: 1.70–1.98(6H,m), 2.04–2.39(6H,m), 2.36–2.55(4H,m), 2.45(3H,s), 2.58–2.72(4H,m), 3.01–3.22 (3H,m), 7.12(1H,d,J=9 Hz), 7.42(1H,d,J=9 Hz), 7.54(1H,s), 7.78(1H,s)

EXAMPLE 132

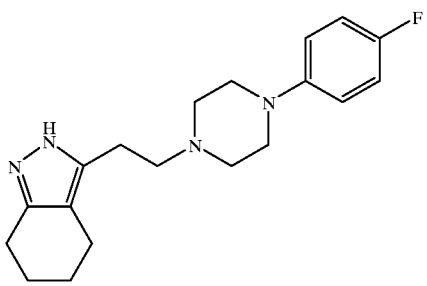

In the same manner as in Example 102 except that 2-(4,5,6,7-tetrahydro-2H-indazol-3-yl)acetic acid obtained in Starting Material Synthesis Example 2 and 1-(4-fluorophenyl)piperazine were used instead of 3-(4,5,6,7-tetrahydro-2H-indazol-3-yl)propionic acid obtained in Staring Material Synthesis Example 1 and 4-(4-chlorophenyl)piperidine, 3-(2-(4-(4-fluorophenyl)piperazin-1-yl)ethyl)-4,5,6,7-tetrahydro-2H-indazole is obtained.

EXAMPLE 133

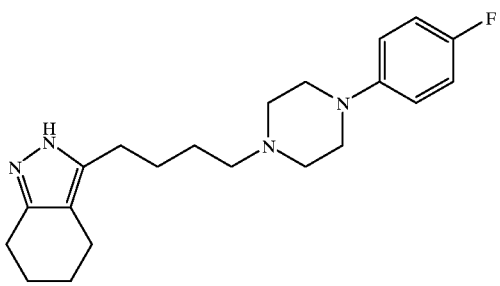

In the same manner as in Example 102 except that 4-(4,5,6,7-tetrahydro-2H-indazol-3-yl)-n-butyric acid obtained in Starting Material Synthesis Example 3 and 1-(4-fluorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(4-(4-(4-fluorophenyl)piperazin-1-yl)butyl)-4,5,6,7-tetrahydro-2H-indazole was obtained.

$^1$H-NMR(CDCl$_3$)δ: 1.52–1.83(8H,m), 2.35–2.44(4H,m), 2.57–2.65(8H,m), 3.11–3.15(4H,m), 6.83–6.99(4H,m)

EXAMPLE 134

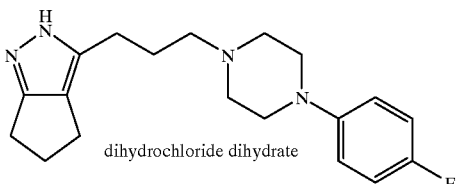

dihydrochloride dihydrate

In the same manner as in Example 102 except that 3-(2,4,5,6-tetrahydrocyclopentapyrazol-3-yl)propionic acid obtained in Starting Material Synthesis Example 4 and 1-(4-fluorophenyl)piperazine were used instead of 3-(4,5,6,7-tetrahydro-2H-indazol-3-yl)propionic acid obtained in Starting Material Synthesis Example 1 and 4-(4- chlorophenyl)piperidine and then by a conventional treatment using hydrochloric acid, 3-(3-(4-(4-fluorophenyl) piperazin-1-yl)propyl)-2,4,5,6-tetrahydrocyclopentapyrazole dihydrochloride dihydrate was obtained, m.p. 228–230° C.

EXAMPLE 135

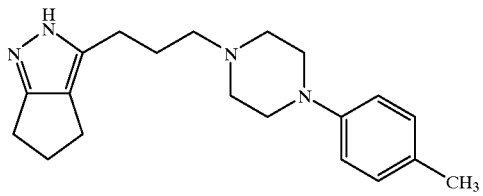

In the same manner as in Example 102 except that 3-(2,4,5,6-tetrahydrocyclopentapyrazol-3-yl)propionic acid obtained in Starting Material Synthesis Example 4 and 1-(4-methylphenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-methylphenyl) piperazin-1-yl)propyl)-2,4,5,6-tetrahydrocyclopentapyrazole was obtained, m.p. 101–102° C.

EXAMPLE 136

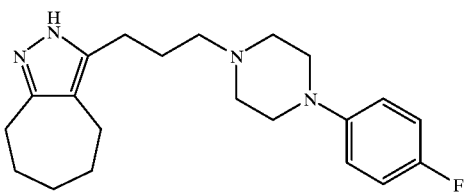

In the same manner as in Example 102 except that 3-(2,4,5,6,7,8-hexahydrocycloheptapyrazol-3-yl)propionic acid obtained in Starting Material Synthesis Example 5 and 1-(4-fluorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-fluorophenyl)piperazin-1-yl)propyl)-2,4,5,6,7,8-hexahydrocycloheptapyrazole was obtained.

$^1$H-NMR(CDCl$_3$)δ: 1.57–1.70(4H,m), 1.77–1.87(4H,m), 2.43–2.48(4H,m), 2.61–2.66(6H,m), 2.70–2.75(2H,m), 3.14–3.18(4H,m), 6.84–7.00(4H,m)

EXAMPLE 137

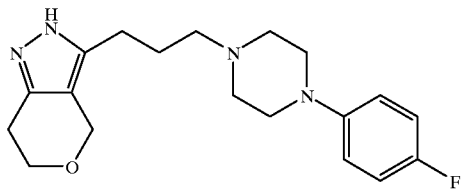

In the same manner as in Example 102 except that 3-(2,4,6,7-tetrahydropyrano[4,3-c]pyrazol-3-yl)propionic acid obtained in Starting Material Synthesis Example 6 and 1-(4-fluorophenyl)piperazine were used instead of 3-(4,5,6,7-tetrahydro-2H-indazol-3-yl)propionic acid obtained in Starting Material Synthesis Example 1 and 4-(4 halophenyl) piperidine, 3-(3-(4-(4-fluorophenyl)piperazin-1-yl)propyl)-2,4,6,7-tetrahydropyrano[4,3-c]pyrazole was obtained.

$^1$H-NMR(CDCl$_3$)δ: 1.85(2H,tt,J=6.6 Hz), 2.48(2H,t,J=7 Hz), 2.57–2.71(6H,m), 2.78(2H,t,J=6 Hz), 3.18(4H,t,J=5 Hz), 3.93(2H,t,J=6 Hz), 4.65(2H,s), 6.82–7.01(4H,m)

EXAMPLE 138

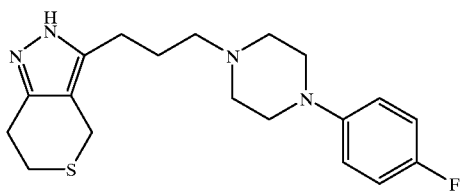

In the same manner as in Example 102 except that 3-(2,4,6,7-tetrahydrothiopyrano[4,3-c]pyrazol-3-yl) propionic acid obtained in Starting Material Synthesis Example 7 and 1-(4-fluorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-fluorophenyl) piperazin-1-yl)propyl)-2,4,6,7-tetrahydrothiopyrano[4,3-c] pyrazole was obtained, m.p. 110–111° C.

EXAMPLE 139

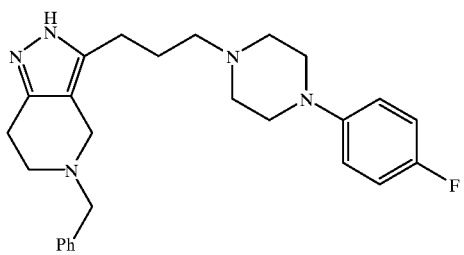

In the same manner as in Example 102 except that 3-(5-benzoyl-4,5,6,7-tetrahydro-2H-pyrazolo[4,3-c]pyridin-3-yl)propionic acid obtained in Starting Material Synthesis Example 8 and 1-(4-fluorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 5-benzyl-3-(3-(4-(4-fluorophenyl)piperazin-1-yl)propyl)-4,5,6,7-tetrahydro-2H-pyrazolo[4,3-c]pyridine was obtained.

$^1$H-NMR(CDCl$_3$)δ: 1.82(2H,tt,J=7.7 Hz), 2.46(2H,t,J=7 Hz), 2.55–2.67(6H,m), 2.77(4H,s), 3.12–3.20(4H,m), 3.44(2H,s), 3.72(2H,s), 6.82–6.98(4H,m), 7.21–7.40(5H,m)

EXAMPLE 140

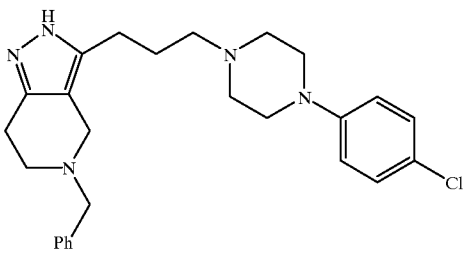

In the same manner as in Example 102 except that 3-(5-benzoyl-4,5,6,7-tetrahydro-2H-pyrazolo[4,3-c]pyridin-3-yl)propionic acid obtained in Starting Material Synthesis Example 8 and 1-(4-chlorophenyl)piperazine were used instead of 3-(4,5,6,7-tetrahydro-2H-indazol-3-yl)propionic acid obtained in Stating Material Synthesis Example 1 and 4-(4-chlorophenyl)piperidine, 5-benzyl-3-(3-(4-(4chlorophenyl)piperazin-1-yl)propyl)-4,5,6,7-tetrahydro-2H-pyrazolo[4,3-c]pyridine was obtained.

$^1$H-NMR(CDCl$_3$)δ: 1.82(2H,tt,J=7.7 Hz), 2.45(2H,t,J=7 Hz), 2.52–2.66(6H,m), 2.76(4H,s), 3.14–3.24(4H,m), 3.43 (2H,s), 3.72(2H,s), 6.84(2H,t,J=9 Hz), 7.19(2H,t,J=9 Hz), 7.21–7.40(5H,m)

EXAMPLE 141

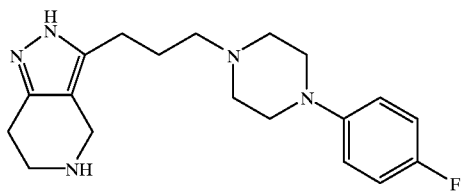

5-Benzyl-3-(3-(4-(4-fluorophenyl)piperazin-1-yl) propyl)-4,5,6,7-tetrahydro-2H-pyrazolo[4,3-c]pyridine (0.5 g) obtained in Example 139 was dissolved in ethanol (10 ml), and Raney nickel (0.2 g) was added to perform catalytic reduction. After the completion of the reaction, the reaction mixture was filtered through celite and the filtrate was concentrated under reduced pressure. The obtained residue was subjected to silica gel column chromatography to give 3-(3-(4-(4-fluorophenyl)piperazin-1-yl)propyl)-4,5,6,7-tetrahydro-2H-pyrazolo[4,3-c]pyridine, $^1$H-NMR(CDCl$_3$)δ: 1.86(2H,tt,J=7.6 Hz), 2.45(2H,t,J=7 Hz), 2.55–2.66(4H,m), 2.89(2H,t,J=6 Hz), 3.00–3.14(6H, m), 3.16–3.23(2H,m), 3.76(2H,s), 6.81–6.98(4H,m)

EXAMPLE 142

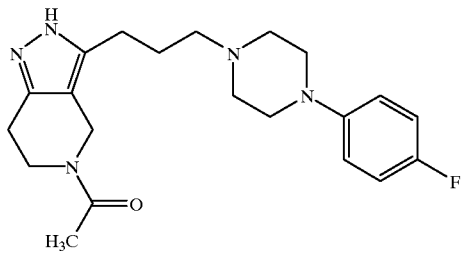

3-(3-(4-(4-Fluorophenyl)piperazin-1-yl)propyl)-4,5,6,7-tetrahydro-2H-pyrazolo[4,3-c]pyridine (0.3 g) obtained in Example 141 was dissolved in a mixed solution of chloroform (5 ml) and saturated aqueous sodium hydrogencarbonate solution (5 ml), and acetyl chloride (0.3 ml) was added dropwise under ice-cooling. After the dropwise addition, the chloroform layer was partitioned and dried over magnesium sulfate. The solvent was evaporated under reduced pressure and the obtained residue was subjected to silica gel column chromatography to give 5-acetyl-3-(3-(4-(4-fluorophenyl) piperazin-1-yl)propyl)-4,5,6,7-tetrahydro-2H-pyrazolo[4,3-c]pyridine.

EXAMPLE 143

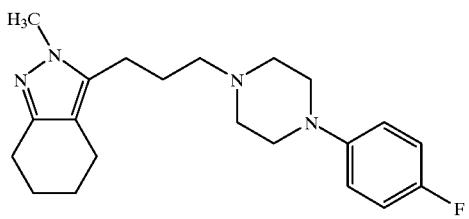

In the same manner as in Example 102 except that 3-(4,5,6,7-tetrahydro-2-methyl-2H-indazol-3-yl)propionic acid obtained in Starting Material Synthesis Example 9 and 1-(4-fluorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-fluorophenyl)piperazin-1-yl)propyl)-4,5,6,7-tetrahydro-2-methyl-2H-indazole was obtained.

$^1$H-NMR(CDCl$_3$)δ: 1.69–1.82(6H,m), 2.37–2.45(4H,m), 2.57–2.65(8H,m), 3.10–3.14( 4H,m), 3.75(3H,s), 6.83–6.99 (4H,m)

EXAMPLE 144

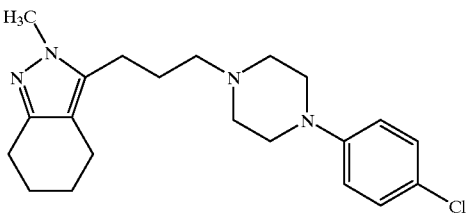

In the same manner as in Example 102 except that 3-(4,5,6,7-tetrahydro-2-methyl-2H-indazol-3-yl)propionic acid obtained in Staring Material Synthesis Example 9 and 1-(4-chlorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4chlorophenyl)piperazin-1-yl)propyl)-4,5,6,7-tetrahydro-2-methyl-2H-indazole was obtained.

$^1$H-NMR(CDCl$_3$)δ: 1.76(6H,m), 2.42(4H,m), 2.56–2.65 (8H,m), 3.18(4H,m), 3.76(3H,s), 6.83(2H,d, J=7 Hz), 7.18 (2H,d, J=7 Hz)

EXAMPLE 145

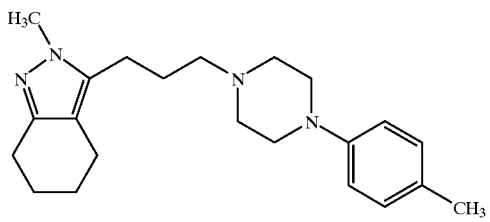

In the same manner as in Example 102 except that 3-(4,5,6,7-tetrahydro-2-methyl-2H-indazol-3-yl)propionic acid obtained in Starting Material Synthesis Example 9 and 1-(4-methylphenyl)piperazine are used instead of 3-(4,5,6,7-tetrahydro-2H-indazol-3-yl)propionic acid obtained in Starting Material Synthesis Example 1 and 4-(4-chlorophenyl)piperidine, 4,5,6,7-tetrahydro-2-methyl-3-(3-(4-(4-methylphenyl)piperazin-1-yl)propyl)-2H-indazole is obtained.

EXAMPLE 146

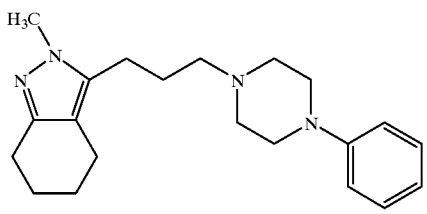

In the same manner as in Example 102 except that 3-(4,5,6,7-tetrahydro-2-methyl-2H-indazol-3-yl)propionic acid obtained in Stating Material Synthesis Example 9 and 1-phenylpiperazine a used instead of 3-(4,5,6,7-tetrahydro-2H-indazol-3-yl)propionic acid obtained in Starting Material Synthesis Example 1 and 4-(4-chlorophenyl)piperidine, 4,5,6,7-tetrahydro-2-methyl-3-(3-(4-phenylpiperazin-1yl)propyl)-2H-indazole is obtained.

EXAMPLE 147

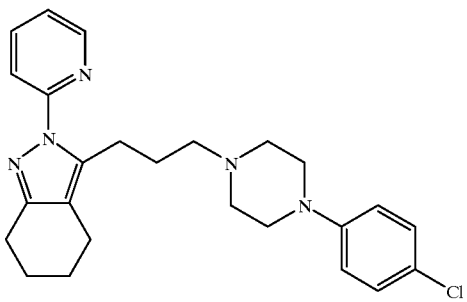

In the same manner as in Example 102 except that 3-(4,5,6,7-tetrahydro-2-(2-pyridyl)-2H-indazol-3-yl) propionic acid obtained in Staring Material Synthesis Example 10 and 1-(4-chlorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-chlorophenyl) piperazin-1-yl)propyl)-4,5,6,7-tetrahydro-2-(2-pyridyl)-2H-indazole was obtained, m.p. 101–103° C.

EXAMPLE 148

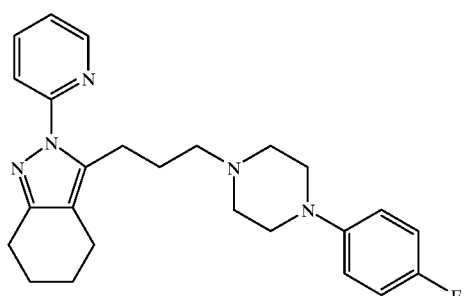

In the same manner as in Example 102 except that 3-(4,5,6,7-tetrahydro-2-(2-pyridyl)-2H-indazol-3-yl) propionic acid obtained in Starting Material Synthesis Example 10 and 1-(4-fluorophenyl)piperazine are used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-fluorophenyl) piperazin-1-yl)propyl)-4,5,6,7-tetrahydro-2-(2-pyridyl)-2H-indazole is obtained.

EXAMPLE 149

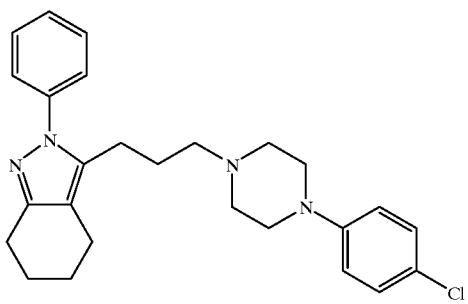

In the same manner as in Example 102 except that 3-(4,5,6,7-tetrahydro-2-phenyl-2H-indazol-3-yl)propionic acid obtained in Starting Material Synthesis Example 11 and 1-(4-chlorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-chlorophenyl) piperazin-1-yl)propyl)-4,5,6,7-tetrahydro-2-phenyl-2H-indazole was obtained, m.p. 127–129° C.

EXAMPLE 150

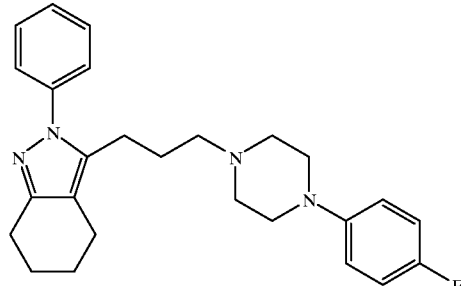

In the same manner as in Example 102 except that 3-(4,5,6,7-tetrahydro-2-phenyl-2H-indazol-3-yl)propionic acid obtained in Starting Material Synthesis Example 11 and 1-(4-fluorophenyl)piperazine are used instead of 3-(4,5,6,7-tetrahydro-2H-indazol-3-yl)propionic acid obtained in Staring Material Synthesis Example 1 and 4-(4-chlorophenyl)piperidine, 3-(3-(4-(4-fluorophenyl)piperazin-1-yl)propyl)-4,5,6,7-tetrahydro-2-phenyl-2H-indazole is obtained.

EXAMPLE 151

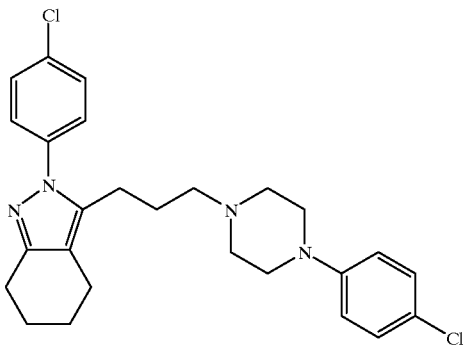

In the same manner as in Example 102 except that 3-(2-(4-chlorophenyl)-4,5,6,7-tetrahydro-2H-indazol-3-yl)propionic acid obtained in Starting Material Synthesis Example 12 and 1-(4-chlorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, 2-(4-chlorophenyl)-3-(3-(4-(4-chlorophenyl)piperazin-1-yl)propyl)-4,5,6,7-tetrahydro-2H-indazole was obtained, m.p. 129–131° C.

EXAMPLE 152

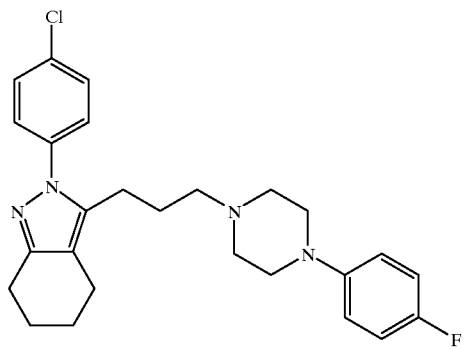

In the same manner as in Example 102 except that 3-(2-(4-chlorophenyl)-4,5,6,7-tetrahydro-2H-indazol-3-yl)propionic acid obtained in Starting Material Synthesis Example 12 and 1-(4-fluorophenyl)piperazine are used instead of 3-(4,5,6,7-tetrahydro-2H-indazol-3-yl)propionic acid obtained in Starting Material Synthesis Example 1 and 4-(4-chlorophenyl)piperidine, 2-(4-chlorophenyl)-3-(3-(4-(4-fluorophenyl)piperazin-1-yl)propyl)-4,5,6,7-tetrahydro-2H-indazole is obtained.

EXAMPLE 153

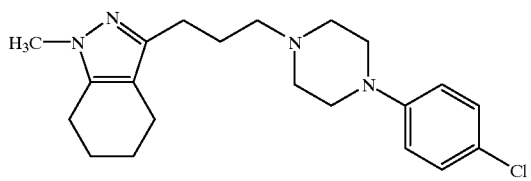

To a solution of 3-(3-chloropropionyl)-4,5,6,7-tetrahydro-1-methyl-1H-indazole (1.0 g) obtained in Starting Material Synthesis Example 13 and 1-(4-chlorophenyl)piperazine hydrochloride (0.9 g) in dimethylformamide (10 ml) was added potassium carbonate (1.1 g) and the mixture was stirred at 60° C. for 3 hours. The reaction mixture was concentrated and the residue was extracted with chloroform, washed with water, dried over magnesium sulfate and concentrated. The obtained 3-(4-(4-chlorophenyl)piperazin-1-yl)propionyl4,5,6,7-tetrahydro-1-methyl-1H-indazole (0.9 g) was dissolved in methanol (10 ml) and chloroform (10 ml), and sodium borohydride (0.7 g) was added under ice-cooling. After the completion of the reaction, the solvent was evaporated under reduced pressure and chloroform and aqueous potassium carbonate solution were added. The chloroform layer was partitioned and dried over magnesium sulfate. The solvent was evaporated under reduced pressure, and isopropyl ether was added to the obtained residue. The precipitated crystals were collected by filtration to give 0.9 g of crude crystals of 3-(1-hydroxy-3-(4-(4-chlorophenyl)piperazin-1-yl)propyl)-4,5,6,7-tetrahydro-1-methyl-1H-indazole.

Sodium iodide (1.5 g) was dissolved in acetonitrile (12 ml) and chlorotrimethylsilane (1.3 ml) was added at room temperature with stirring. The above-mentioned compound (0.6 g) was further added. The reaction mixture was refluxed under heating for 2 hours and cooled. An aqueous sodium sulfite solution and an aqueous potassium carbonate solution were added and the mixture was extracted with ethyl acetate. The solution was dried over magnesium sulfate and the solvent was evaporated under reduced pressure. The residue was subjected to silica gel column chromatography to give 3-(3-(4-(4-chlorophenyl)piperazin-1-yl)propyl)-4,5,6,7-tetrahydro-1-methyl-1H-indazole.

This compound could be also obtained by the following method. That is, 4-(4-chlorophenyl)-1-(4-oxo-4-(2-oxocyclohexyl)butyryl)piperazine obtained by using 4-oxo4-(2-oxocyclohexyl)-n-butyric acid and 1-(4-chlorophenyl)piperazine instead of 3-(4,5,6,7-tetrahydro-2H-indazol-3-yl)propionic acid and 4-(4-chlorophenyl)piperidine used in Example 102 was refluxed under heating in a methanol solvent with methyl hydrazine. After the completion of the reaction, the solvent was evaporated under reduced pressure to give an oily substance. This compound was dissolved in tetrahydrofuran and thereto was added lithium aluminum hydride in an ice bath. After the completion of the reaction, a mixture of tetrahydrofuran—water was added, and then ethyl acetate and magnesium sulfate were further added. The reaction mixture was filtered through celite, and the solvent was evaporated under reduced pressure. The obtained residue was subjected to silica gel column chromatography to give 3-(3-(4-(4chlorophenyl)piperazin-1-yl)propyl)-4,5,6,7-tetrahydro-1-methyl-1H-indazole.

$^1$H-NMR(CDCl$_3$)δ: 1.72(2H,m), 1.78–1.88(4H,m), 2.38–2.64(12H,m), 3.16(4H,m), 3.68(3H,s), 6.83(2H,d,J=7 Hz), 7.18(2H,d,J=7 Hz)

EXAMPLE 154

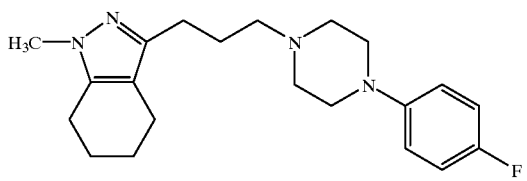

In the same manner as in Example 153 except that 1-(4-fluorophenyl)piperazine was used instead of 1-(4 halophenyl)piperazine, 3-(3-(4-(4-fluorophenyl)piperazin-1-yl)propyl)-4,5,6,7-tetrahydro-1-methyl-1H-indazole was obtained.

$^1$H-NMR(CDCl$_3$)δ: 1.68–1.90(6H,m), 2.33–2.70(12H, m), 3.10–3.14(4H,m), 3.66(3H,s), 6.83–6.98(4H,m)

EXAMPLE 155

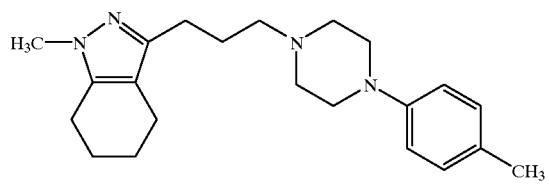

In the same manner as in Example 153 except that 1-(4-methylphenyl)piperazine is used instead of 1-(4-chlorophenyl)piperazine, 4,5,6,7-tetrahydro-1-methyl-3-(3-(4-(4-methylphenyl)piperazine-1-yl)propyl)-1H-indazole is obtained.

EXAMPLE 156

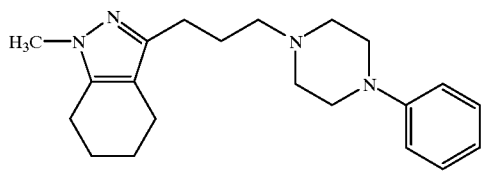

In the same manner as in Example 153 except that 1-phenylpiperazine is used instead of 1-(4-chlorophenyl) piperazine, 4,5,6,7-tetrahydro-1-methyl-3-(3-(4-phenylpiperazin-1-yl)propyl)-1H-indazole is obtained.

EXAMPLE 157

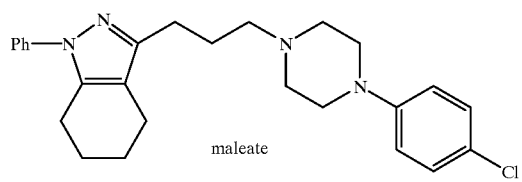

In the same manner as in Example 153 except that 3-(3-chloropropionyl)-4,5,6,7-tetrahydro-1-phenyl-2H-indazole obtained in Stating Material Synthesis Example 14 was used instead of 3-(3-chloropropionyl)-4,5,6,7-tetrahydro-1-methyl-1H-indazole obtained in Starting Material Synthesis Example 13, and then by a conventional treatment using maleic acid, 3-(3-(4-(4-chlorophenyl)piperazin-1-yl)propyl)-4,5,6,7-tetrahydro-1-phenyl-1H-indazole maleate was obtained. In the same manner as in Example 153 except that phenylhydrazine was used instead of methylhydrazine, and then by a conventional treatment using maleic acid, 3-(3-(4-(4-chlorophenyl)piperazin-1-yl) propyl)-4,5,6,7-tetrahydro-1-phenyl-1H-indazole maleate, m.p. 150–151° C.

EXAMPLE 158

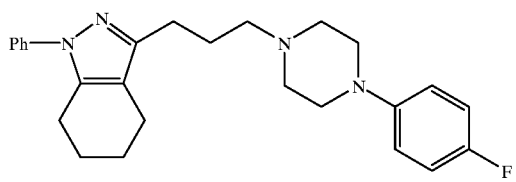

In the same manner as in Example 157 except that 1-(4-fluorophenyl)piperazine is used instead of 1-(4-chlorophenyl)piperazine, 3-(3-(4-(4-fluorophenyl) piperazin-1-yl)propyl)-4,5,6,7-tetrahydro-1-phenyl-1H-indazole is obtained.

EXAMPLE 159

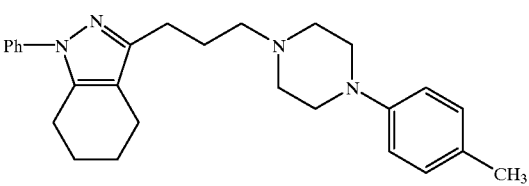

In the same manner as in Example 157 except that 1-(4-methylphenyl)piperazine is used instead of 1-(4-chlorophenyl)piperazine, 4,5,6,7-tetrahydro-1-phenyl-3-(3-(4-(4-methylphenyl)piperazin-1-yl)propyl)-1H-indazole is obtained.

EXAMPLE 160

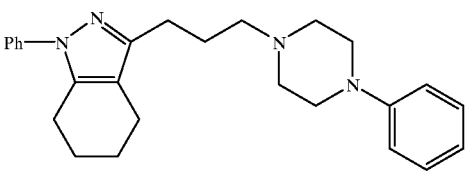

In the same manner as in Example 157 except that 1-phenylpiperazine is used instead of 1-(4-chlorophenyl) piperazine, 4,5,6,7-tetrahydro 1-phenyl-3-(3-(4-phenylpiperazin-1-yl)propyl)-1H-indazole is obtained.

EXAMPLE 161

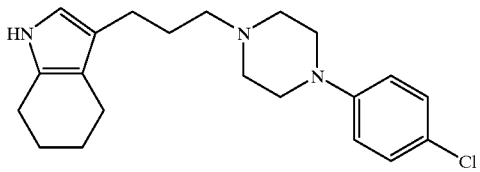

To a solution of 1-benzenesulfonyl-3-(3-chloropropionyl)-4,5,6,7-tetrahydroindole (2.0 g) obtained in Starting Material Synthesis Example 15 and 1-(4-chlorophenyl)piperazine hydrochloride (1.9 g) in dimethylformamide (20 ml) was added potassium carbonate (2.1 g) and the mixture was stirred for 3 hours at 60° C. The reaction of was concentrated, extracted with chloroform, washed with water, dried over magnesium sulfate and concentrated. The residue [(3-(4-(4-chlorophenyl)piperazine-1-yl)propionyl-4,5,6,7-tetrahydro-1-phenylsulfonyl-indole)-] was added to dioxane (20 ml) and 5M sodium hydroxide (20 ml), and the mixture was stirred for 20 hours at room temperature. The reaction mixture was extracted with ethyl acetate, dried over magnesium sulfate and concentrated under reduced pressure. The obtained 3-(4-(4-chlorophenyl)piperazin-1-yl)propionyl-4,5,6,7-tetrahydroindole (1.7 g) was dissolved in methanol (20 ml) and chloroform (20 ml), sodium borohydride (1.4 g) was added thereto in an ice bath. After the completion of the reaction, the solvent was evaporated under reduced pressure, and chloroform and an aqueous potassium carbonate solution were added and the chloroform layer was partitioned. After drying over magnesium sulfate, the solvent was evaporated under reduced pressure, and isopropyl ether was added to the obtained residue. The precipitated crystals were collected by filtration to give 1.3 g of crude crystals of 3-(1-hydroxy-3-(4-(4-chlorophenyl)piperazin-1-yl)propyl)-4,5,6,7-tetrahydroindole.

Sodium iodide (1.5 g) was dissolved in acetonitrile (12 ml) and chlorotrimethylsilane (1.3 ml) was added with stirring at room temperature and the above-mentioned compound (0.6 g) was further added. The reaction mix was refluxed under heating for 2 hours and cooled. An aqueous sodium sulfite solution and an aqueous potassium carbonate solution were added and extracted with ethyl acetate. The solution was dried over magnesium sulfate and the solvent was evaporated under reduced pressure. The residue was subjected to silica gel column chromatography to give 3-(3-(4-(4-chlorophenyl)piperazin-1-yl)propyl)-4,5,6,7-tetrahydroindole.

EXAMPLE 162

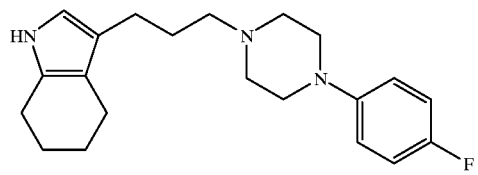

In the same manner as in Example 161 except that 1-(4-fluorophenyl)piperazine is used instead of 1-(4-chlorophenyl)piperazine, 3-(3-(4-(4-fluorophenyl)piperazin-1-yl)propyl)-4,5,6,7-tetrahydroindole is obtained.

EXAMPLE 163

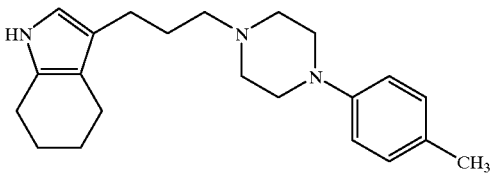

In the same manner as in Example 161 except that 1-(4-methylphenyl)piperazine is used instead of 1-(4-chlorophenyl)piperazine, 4,5,6,7-tetrahydro-3-( 3-(4-(4-methylphenyl)piperazin-1-yl)propyl)indole is obtained.

EXAMPLE 164

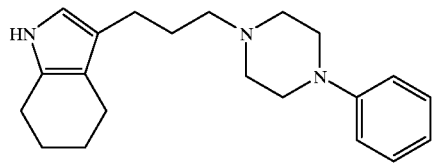

In the same manner as in Example 161 except that 1-phenylpiperazine is used instead of 1-(4-chlorophenyl)piperazine, 4,5,6,7-tetrahydro-3-(3-(4-phenylpiperazin-1-yl)propyl)indole is obtained.

EXAMPLE 165

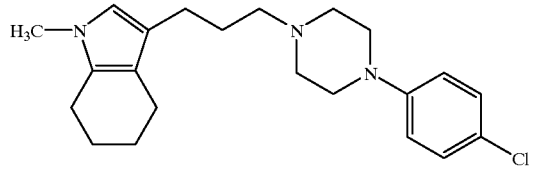

3-(3-(4-(4-Chlorophenyl)piperazin-1-yl)propyl)-4,5,6,7-tetrahydroindole (0.5 g) obtained in Example 161 and potassium carbonate (0.6 g) were dissolved in dimethylformamide (10 ml) and methyl iodide (0.3 g) was added under ice-cooling with stirring. The reaction mixture was stirred at room temperature for 2 hours and the solvent was evaporated under reduced pressure. Chloroform and an aqueous potassium carbonate solution were added and the chloroform layer was separated. The layer was dried over magnesium sulfate and the solvent was evaporated under reduced pressure. The residue was subjected to silica gel column chromatography to give 3-(3-(4-(4-chlorophenyl)piperazin-1-yl)propyl)-4,5,6,7-tetrahydro-1-methylindole.

EXAMPLE 166

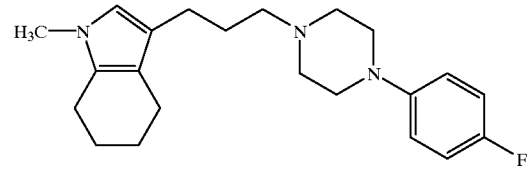

In the same manner as in Example 165 except that 3-(3-(4-(4-fluorophenyl)piperazin- 1-yl)propyl)-4,5,6,7- tetrahydroindole is used instead of 3-(3-(4-(4-chlorophenyl)piperazin-1-yl)propyl)-4,5,6,7-tetrahydroindole, 3-(3-(4-(4-fluorophenyl)piperazin-1-yl)propyl)-4,5,6,7-tetrahydro-1-methylindole is obtained.

EXAMPLE 167

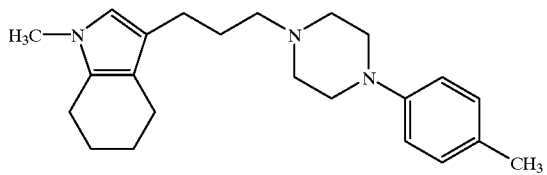

In the same manner as in Example 165 except that 4,5,6,7-tetrahydro-3-(3-(4-(4-methylphenyl)piperazin-1-yl)propyl)indole is used instead of 3-(3-(4-(4-chlorophenyl)piperazin-1-yl)propyl)-4,5,6,7-tetrahydroindole, 4,5,6,7-tetrahydro-1-methyl-3-(3-(4-(4-methylphenyl)piperazin-1-yl)propyl)indole is obtained.

EXAMPLE 168

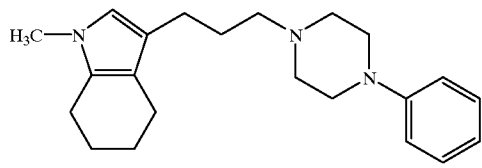

In the same manner as in Example 165 except that 4,5,6,7-tetrahydro-3-(3-(4-phenylpiperazin-1-yl)propyl)indole is used instead of 3-(3-(4-(4-chlorophenyl)piperazin-1-yl)propyl)-4,5,6,7-tetrahydroindole, 4,5,6,7-tetrahydro-1-methyl-3-(3-(4-phenylpiperazin-1-yl)propyl)indole is obtained.

EXAMPLE 169

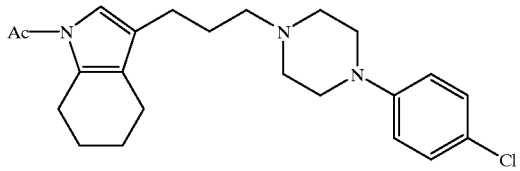

3-(3-(4-(4-Chlorophenyl)piperazin-1-yl)propyl)-4,5,6,7-tetrahydroindole (0.5 g) obtained in Example 161 and triethylamine (0.6 ml) were dissolved in dichloromethane (10 ml) and acetyl chloride (0.3 g) was added under ice-cooling with stirring. The reaction mixture was stirred for 2 hours at room temperature and an aqueous potassium carbonate solution is added, and the chloroform layer was separated. After drying over magnesium sulfate, the solvent was evaporated under reduced pressure, and the obtained residue was subjected to silica gel column chromatography to give 1-acetyl-3-(3-(4-(4chlorophenyl)piperazin-1-yl)propyl)-4,5,6,7-tetrahydroindole.

EXAMPLE 170

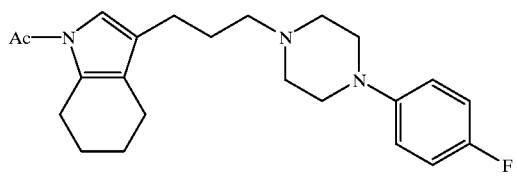

In the same manner as in Example 169 except that 3-(3-(4-(4-fluorophenyl)piperazin-1-yl)propyl)-4,5,6,7-tetrahydroindole is used instead of 3-(3-(4-(4chlorophenyl)piperazin-1-yl)propyl)-4,5,6,7-tetrahydroindole, 1-acetyl-3-(3-(4-(4-fluorophenyl)piperazine-1-yl)propyl)-4,5,6,7-tetrahydroindole is obtained.

EXAMPLE 171

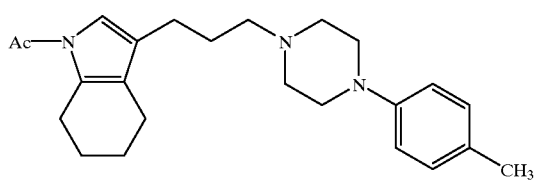

In the same manner as in Example 169 except that 4,5,6,7-tetrahydro-3-(3-(4-(4-methylphenyl)piperazin-1-yl)propyl)indole is used instead of 3-(3-(4(4-chlorophenyl)piperazin-1-yl)propyl)-4,5,6,7-tetrahydroindole, 1-acetyl-4,5,6,7-tetrahydro-3-(3-(4-(4-methylphenyl)piperazin-1-yl)propyl)indole is obtained.

EXAMPLE 172

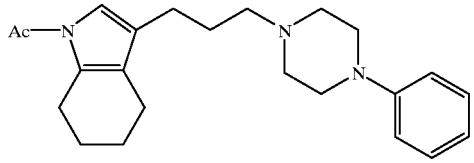

In the same manner as in Example 169 except that 4,5,6,7-tetrahydro-3-(3-(4-phenylpiperazin-1-yl)propyl)indole is used instead of 3-(3-(4-(4-chlorophenyl)piperazin-1-yl)propyl)-4,5,6,7-tetrahydroindole, 1-acetyl-4,5,6,7-tetrahydro-3-(3-(4-phenylpiperazin-1-yl)propyl)indole is obtained.

EXAMPLE 173

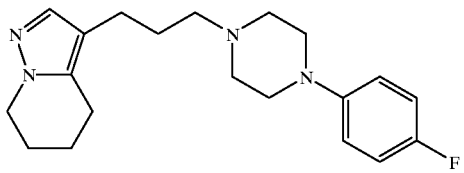

(3-(4,5,6,7-Tetrahydropyrazolo[2,3-a]pyridin-3-yl)-3-oxypropyl)trimethyl ammonium iodide (1.2 g) obtained in Starting Material Synthesis Example 16 and 1-(4-fluorophenyl)piperazine (0.7 g) were suspended in methanol (20 ml) and the mixture was refluxed under heating for 4 hours. The solvent was evaporated under reduced pressure and chloroform and an aqueous potassium carbonate solution were added. The chloroform layer was separated and dried over magnesium sulfate. The solvent was evaporated under reduced pressure, and the residue was subjected to silica gel column chromatography to give 1.0 g of 3-(3-(4-(4-fluorophenyl)piperazin-1-yl)propionyl)-4,5,6,7-tetrahydropyrazolo[2,3-a]pyridine, m.p. 141–142° C.

This compound (0.9 g) was dissolved in methanol (10 ml) and chloroform (10 ml) and thereto was added sodium borohydride (0.7 g) in an ice bath. After the completion of the reaction, the solvent was evaporated under reduced pressure and chloroform and an aqueous potassium carbonate solution were added. The chloroform layer was separated and dried over magnesium sulfate. The solvent was evaporated under reduced pressure and isopropyl ether was added to the obtained residue. The precipitated crystals were collected by filtration to give 1.0 g of 3-(1-hydroxy-3-(4-(4-fluorophenyl)piperazin-1-yl)propyl)-4,5,6,7-tetrahydropyrazolo[2,3-a]pyridine, m.p. 130–131° C.

Sodium iodide (1.5 g) was dissolved in acetonitrile (12 ml) and chlorotrimethylsilane (1.3 ml) was added at room temperature with stirring. The above-mentioned compound (0.6 g) was further added. The reaction mixture was refluxed under heating for 2 hours and cooled. An aqueous sodium sulfite solution and an aqueous potassium carbonate solution were added and the mixture was extracted with ethyl acetate. The solution was dried over magnesium sulfate and evaporated under reduced pressure. The residue was subjected to silica gel column chromatography to give 3-(3-(4-(4fluorophenyl)piperazin-1-yl)propyl)-4,5,6,7-tetrahydropyrazolo[2,3-a]pyridine.

$^1$H-NMR(CDCl$_3$)δ: 1.70–1.92(4H,m), 1.97–2.06(2H,m), 2.37–2.45(4H,m), 2.58–2.70(6H,m), 3.11–3.17(4H,m), 4.08–4.16(2H,m), 6.84–6.99(4H,m), 7.29(1H,s)

EXAMPLE 174

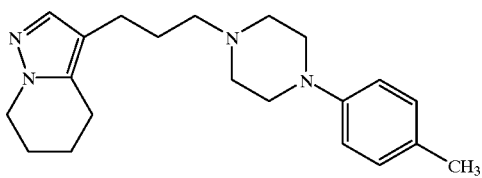

In the same manner as in Example 173 except that 1-(4-methylphenyl)piperazine is used instead of 1-(4-fluorophenyl)piperazine, 4,5,6,7-tetrahydro-3-(3-(4-(4-methylphenyl)piperazin-1-yl)propyl)pyrazolo[2,3-a]pyridine is obtained.

EXAMPLE 175

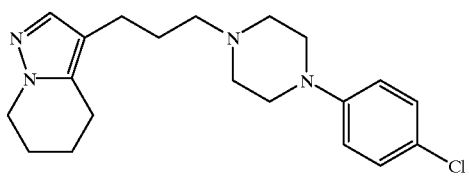

In the same manner as in Example 173 except that 1-(4-chlorophenyl)piperazine is used instead of 1-(4-fluorophenyl)piperazine, 3-(3-(4-(4-chlorophenyl)piperazin-1-yl)propyl)-4,5,6,7-tetrahydropyrazolo[2,3-a]pyridine is obtained.

EXAMPLE 176

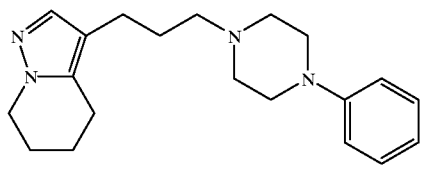

In the same manner as in Example 173 except that 1-phenylpiperazine is used instead of 1-(4-fluorophenyl)piperazine, 4,5,6,7-tetrahydro-3-(3-(4-phenylpiperazin-1-yl)propyl)pyrazolo[2,3-a]pyridine is obtained.

EXAMPLE 177

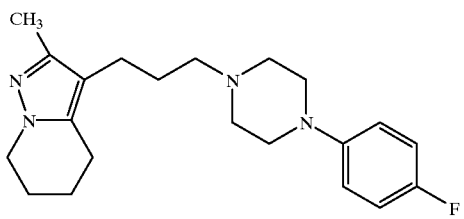

In the same manner as in Example 173 except that (3-(4,5,6,7-tetrahydro-2-methylpyrazolo[2,3-a]pyridin-3-yl)-3-oxypropyl)trimethyl ammonium iodide is used instead of (3-(4,5,6,7-tetrahydropyrazolo[2,3-a]pyridin-3-yl)-3oxypropyl)trimethyl ammonium iodide obtained in Stating Material Synthesis Example 16, 3-(3-(4-(4-fluorophenyl)piperazin-1-yl)propyl)-4,5,6,7-tetrahydro-2-methylpyrazolo[2,3-a]pyridine is obtained.

EXAMPLE 178

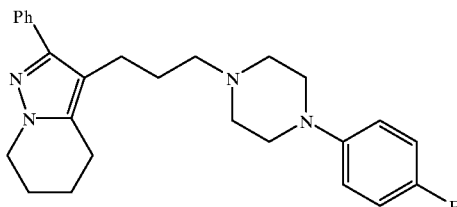

In the same manner as in Example 173 except that (3-(4,5,6,7-tetrahydro-2-phenylpyrazolo[2,3-a]pyridin-3-yl)-3-oxypropyl)trimethyl ammonium iodide is used instead of (3-(4,5,6,7-tetrahydropyrazolo[2,3-a]pyridin-3-yl)-3-oxypropyl)trimethyl ammonium iodide obtained in Staring Material Synthesis Example 16, 3-(3-(4-(4-fluorophenyl)piperazin-1-yl)propyl)-4,5,6,7-tetrahydro-2-phenylpyrazolo[2,3-a]pyridine is obtained.

EXAMPLE 179

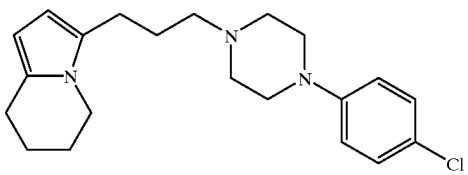

In the same manner as in Example 153 except that 3-(3-chloropropionyl)-5,6,7,8-tetrahydroindolidine obtained in Starting Material Synthesis Example 17 is used instead of 3-(3-chloropropionyl)-4,5,6,7-tetrahydro-1-methyl-1H-indazole obtained in Starting Material Synthesis Example 13, 3-(3-(4-(4-chlorophenyl)piperazin-1-yl)propyl)-5,6,7,8-tetrahydroindolidine is obtained.

EXAMPLE 180

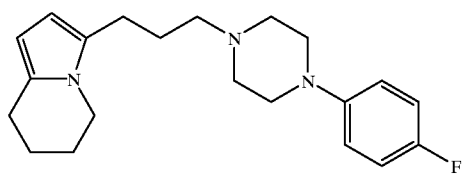

In the same manner as in Example 179 except that 1-(4-fluorophenyl)piperazine is used instead of 1-(4chlorophenyl)piperazine, 3-(3-(4-(4-fluorophenyl)piperazin-1-yl)propyl)-5,6,7,8-tetrahydroindolidine is obtained.

EXAMPLE 181

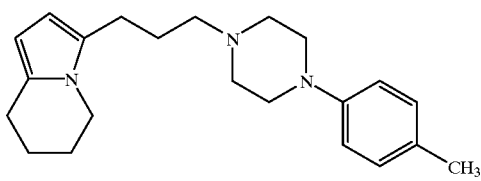

In the same manner as in Example 179 except that 1-(4-methylphenyl)piperazine is used instead of 1-(4chlorophenyl)piperazine 5,6,7,8-tetrahydro-3-(3-(4-(4-methylphenyl)piperazin-1-yl)propyl)indolamine is obtained.

EXAMPLE 182

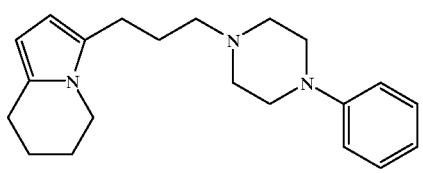

In the same manner as in Example 179 except that 1-phenylpiperazine is used instead of 1-(4-chlorophenyl) piperazine, 5,6,7,8-tetrahydro-3-(3-(4-phenylpiperazin-1-yl)propyl)indolamine is obtained.

EXAMPLE 183

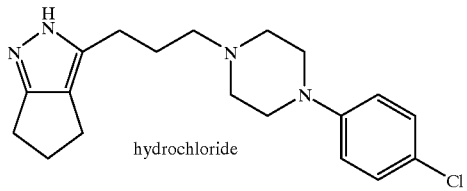

hydrochloride

In the same manner as in Example 102 except that 3-(2,4,5,6-tetrahydrocyclopentapyrazol-3-yl)propionic acid obtained in Starting Material Synthesis Example 4 and 1-(4-chlorophenyl)piperazine were used instead of 3-(4,5,6,7-tetrahydro-2H-indazol-3-yl)propionic acid obtained in Starting Material Synthesis Example 1 and 4-(4-chlorophenyl)piperidine, and then by a conventional treatment using hydrochloric acid, 3-(3-(4-(4-chlorophenyl)piperazin-1-yl)propyl)-2,4,5,6-tetrahydrocyclopentapyrazole hydrochloride was obtained, m.p. 228–230° C.

EXAMPLE 184

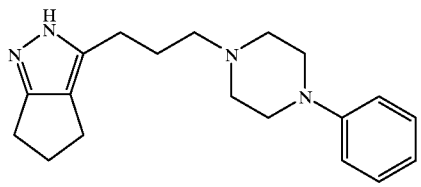

In the same manner as in Example 102 except that 3-(2,4,5,6-tetrahydrocyclopentapyrazol-3-yl)propionic acid obtained in Starting Material Synthesis Example 4 and 1-phenylpiperazine are used instead of 3-(4,5,6,7-tetrahydro-2H-indazol-3-yl)propionic acid obtained in Starting Material Synthesis Example 1 and 4-(4-chlorophenyl) piperidine, 2,4,5,6-tetrahydro-3-(3-(4-phenylpiperazin-1-yl)propyl)cyclopentapyrazole is obtained.

EXAMPLE 185

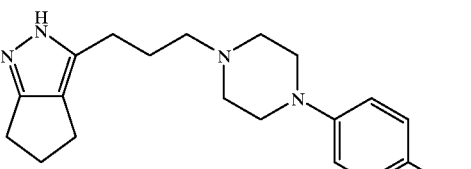

In the same manner as in Example 102 except that 3-(2,4,5,6,7,8-hexahydrocycloheptapyrazol-3-yl)propionic acid obtained in Starting Material Synthesis Example 5 and 1-(4-methylphenyl)piperazine are used instead of 3-(4,5,6,7-tetrahydro-2H-indazol-3-yl)propionic acid obtained in Starting Material Synthesis Example 1 and 4-(4-chlorophenyl)piperidine, 2,4,5,6,7,8-hexahydro-3-(3-(4-(4-methylphenyl)piperazin-1-yl)propyl)cycloheptapyrazole is obtained.

EXAMPLE 186

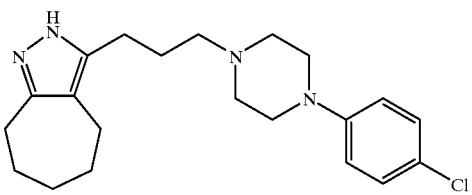

In the same manner as in Example 102 except that 3-(2,4,5,6,7,8-hexahydrocycloheptapyrazol-3-yl)propionic acid obtained in Starting Material Synthesis Example 5 and 1-(4-chlorophenyl)piperazine are used instead of 3-(4,5,6,7-tetrahydro-2H-indazol-3-yl)propionic acid obtained in Starting Material Synthesis Example 1 and 4-(4-chlorophenyl) piperidine, 3-(3-(4-(4-chlorophenyl)piperazin-1-yl)propyl)-2,4,5,6,7,8-hexahydrocycloheptapyrazol is obtained.

EXAMPLE 187

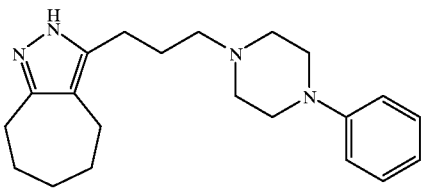

In the same manner as in Example 102 except that 3-(2,4,5,6,7,8-hexahydrocycloheptapyrazol-3-yl)propionic acid obtained in Starting Material Synthesis Example 5 and 1-phenylpiperazine are used instead of 3-(4,5,6,7-tetrahydro-2H-indazol-3-yl)propionic acid obtained in Starting Material Synthesis Example 1 and 4-(4-chlorophenyl) piperidine, 2,4,5,6,7,8-hexahydro-3-(3-(4-phenylpiperazin-1-yl)propyl)cycloheptapyrazole is obtained.

EXAMPLE 188

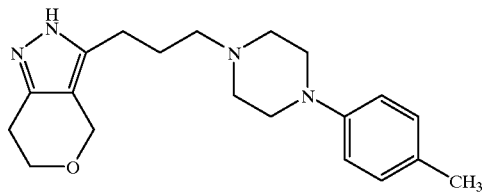

In the same manner as in Example 102 except that 3-(2,4,6,7-tetrahydropyrano[4,3-c]pyrazol-3-yl)propionic acid obtained in Starting Material Synthesis Example 6 and 1-(4-methylphenyl)piperazine are used instead of 3-(4,5,6,7-tetrahydro 2H-indazol-3-yl)propionic acid obtained in Starting Material Synthesis Example 1 and 4-(4-chlorophenyl)piperidine, 2,4,6,7-tetrahydro-3-(3-(4-(4-methylphenyl)piperazin-1-yl)propyl)pyrano[4,3-c]pyrazole is obtained.

EXAMPLE 189

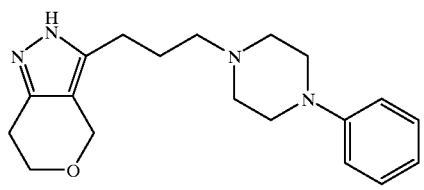

In the same manner as in Example 102 except that 3-(2,4,6,7-tetrahydropyrano[4,3-c]pyrazol-3-yl)propionic acid obtained in Starting Material Synthesis Example 6 and 1-(4-chlorophenyl)piperazine are used instead of 3-(4,5,6,7-tetrahydro-2H-indazol-3-yl)propionic acid obtained in Starting Material Synthesis Example 1 and 4-(4-chlorophenyl) piperidine, 3-(3-(4-(4-chlorophenyl)piperazin-1-yl)propyl)-2,4,6,7-tetrahydropyrano[4,3-c]pyrazole is obtained.

EXAMPLE 190

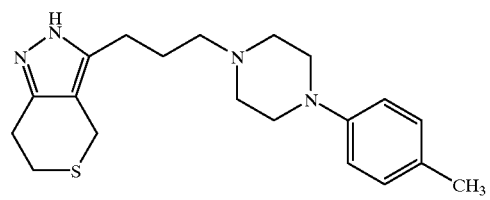

In the same manner as in Example 102 except that 3-(2,4,6,7-tetrahydropyrano[4,3-c]pyrazol-3-yl)propionic acid obtained in Starting Material Synthesis Example 6 and 1-phenylpiperazine are used instead of 3-(4,5,6,7-tetrahydro-2H-indazol-3-yl)propionic acid obtained in Starting Material Synthesis Example 1 and 4-(4-chlorophenyl) piperidine, 2,4,6,7-tetrahydro-3-(3-(4-phenylpiperazin-1-yl)propyl)pyrano[4,3-c]pyrazole is obtained.

EXAMPLE 191

In the same manner as in Example 102 except that 3-(2,4,6,7-tetrahydrothiopyrano[4,3-c]pyrazol-3-yl) propionic acid obtained in Starting Material Synthesis Example 7 and 1-(4-methylphenyl)piperazine are used instead of 3-(4,5,6,7-tetrahydro-2H-indazol-3-yl)propionic acid obtained in Starting Material Synthesis Example 1 and 4-(4-chlorophenyl)piperidine, 2,4,6,7-tetrahydro-3-(3-(4-(4-methylphenyl)piperazine-1-yl)propyl)thiopyrano[4,3-c] pyrazole is obtained.

EXAMPLE 192

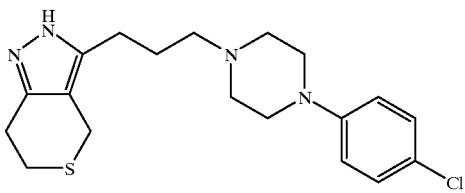

In the same manner as in Example 102 except that 3-(2,4,6,7-tetrahydrothiopyrano[4,3-c]pyrazol-3-yl)propionic acid obtained in Starting Material Synthesis Example 7 and 1-(4-chlorophenyl)piperazine are used instead of 3-(4,5,6,7-tetrahydro-2H-indazol-3-yl)propionic acid obtained in Starting Material Synthesis Example 1 and 4-(4-chlorophenyl)piperidine, 3-(3-(4-(4-chlorophenyl)piperazin-1-yl)propyl)-2,4,6,7-tetrahydrothiopyrano[4,3-c]pyrazole is obtained.

EXAMPLE 193

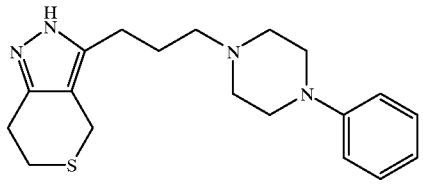

In the same manner as in Example 102 except that 3-(2,4,6,7-tetrahydrothiopyrano[4,3-c]pyrazol-3-yl)propionic acid obtained in Starting Material Synthesis Example 7 and 1-phenylpiperazine are used instead of 3-(4,5,6,7-tetrahydro-2H-indazol-3-yl)propionic acid obtained in Starting Material Synthesis Example 1 and 4-(4 halophenyl)piperidine, 2,4,6,7-tetrahydro-3-(3-(4-phenylpiperazin-1-yl)propyl)thiopyrano[4,3-c]pyrrole is obtained.

EXAMPLE 194

Compound A

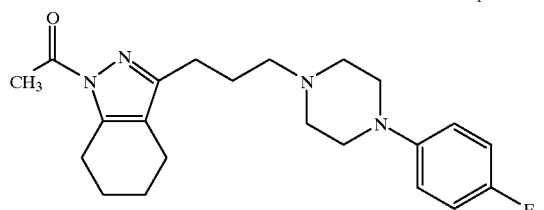

Compound B

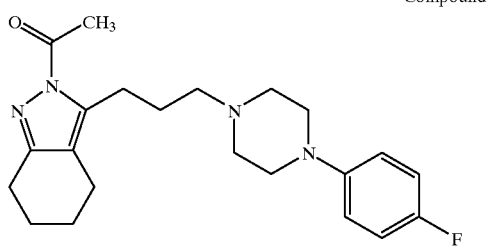

To a mixture of 3-(3-(4-(4-fluorophenyl)piperazin-1-yl)propyl)-4,5,6,7-tetrahydro-2H-indazole (3.1 g), dimethylformamide (30 ml) and triethylamine (2.5 ml) was dropwise added acetyl chloride (0.72 ml) under ice-cooling. The mixture was stirred as it was for 30 minutes. The reaction mixture was poured into ice water (200 ml). The mixture was extracted with ethyl acetate, washed with water and dried over anhydrous magnesium sulfate. The filtrate was concentrated under reduced pressure to give 3.4 g of an oily substance. The oil was subjected to silica gel column chromatography (eluent; hexane:ethyl acetate=1:2) to give 0.60 g of 1-acetyl-3-(3-(4-(4-fluorophenyl)piperazin-1-yl)propyl)-4,5,6,7-tetrahydro-1H-indazole (component eluted later (compound A)), and 0.30 g of 2-acetyl-3-(3-(4-(4-fluorophenyl)piperazin-1-yl)propyl)-4,5,6,7-tetrahydro-2H-indazole (component eluted first (compound B)). 1-Acetyl-3-(3-(4-(4-fluorophenyl)piperazin-1-yl)propyl)-4,5,6,7-tetrahydro-1H-indazole (compound A: m.p. 60–61° C.); 2-Acetyl-3-(3-(4-(4-fluorophenyl)piperazin-1-yl)propyl)-4,5,6,7-tetrahydro-2H-indazole (compound B: m.p. 104–106° C.).

EXAMPLE 195

Compound A

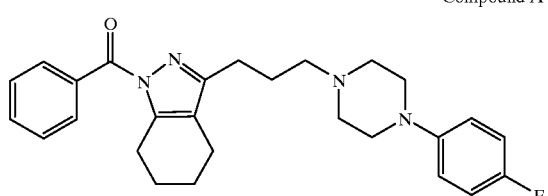

Compound B

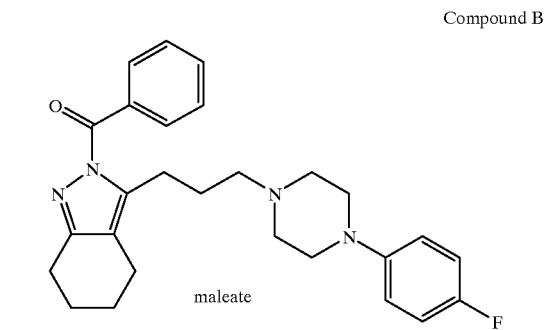

maleate

In the same manner as in Example 194 except that benzoyl chloride (1.2 ml) was used instead of acetyl chloride, 1.0 g of 1-benzoyl-3-(3-(4-(4-fluorophenyl)piperazin-1-yl)propyl)-4,5,6,7-tetrahydro-1 H-indazole (component eluted later compound A), and 0.45 g of 2-benzoyl-3-(3-(4-(4-fluorophenyl)piperazin-1-yl)propyl)-4,5,6,7-tetrahydro-2H-indazole (component eluted first: compound B) were obtained. 1-Benzoyl-3-(3-(4-(4-fluorophenyl)piperazin-1-yl)propyl)-4,5,6,7-tetrahydro-1H-indazole (compound A: m.p. 71–72° C.); 2-Benzoyl-3-(3-(4-(4-fluorophenyl)piperazin-1-yl)propyl)-4,5,6,7-tetrahydro-2H-indazole (compound B: m.p. as maleate 147–148° C.).

EXAMPLE 196

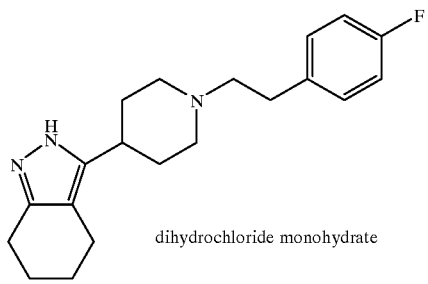

dihydrochloride monohydrate

Lithium diisopropylamide solution prepared from diisopropylamine (2.8 ml) and 1 M n-butyl lithium (11 ml) in tetrahydrofuran (40 ml) was cooled to −78° C. and cyclohexanone (2.0 ml) was added. The mixture was stirred at −78° C. for 1 hour and 1-tert-butoxycarbonyl-4-imidazocarbonylpiperidine (4.8 g) prepared from N-tert-butoxycarbonylisonipecotic acid was added. The mixture was stirred at room temperature for 1 hour. The reaction mixture was concentrated and water was added to the obtained residue. The mixture was extracted with ethyl acetate and the extract was dried over anhydrous magnesium sulfate. The filtrate was concentrated under reduced pressure to give 3.8 g of an oily substance. The oil was subjected to silica gel column chromatography (eluent; chloroform:methanol=20:1) to give 2-((1-tert-butoxycarbonylpiperidin-4-yl)carbonyl)cyclohexanone, m.p. 71–72° C.

2-((1-tert-Butoxycarbonylpiperidin-4-yl)carbonyl) cyclohexanone (1.0 g) was dissolved in trifluoroacetic acid (10 ml) and the solution was stirred at room temperature for 30 minutes. The solvent was evaporated and the residue was made alkaline with an aqueous potassium carbonate solution and extracted with ethyl acetate. After drying over magnesium sulfite, the solvent was evaporated under reduced pressure, dimethylformamide (10 ml), 4-fluorophenylacetic acid (0.5 g) and triethylamine (0.9 ml) were added to the obtained residue. Diethyl cyanophosphate (0.5 ml) was added dropwise in an ice bath while stirring the mixture. The mixture was stirred further for 3 hours. After the completion of the reaction, the solvent was evaporated under reduced pressure, and water was added to the obtained residue. The mixture was extracted with chloroform and the extract was dried over magnesium sulfate. The solvent was evaporated under reduced pressure. To a solution (50 ml) of the obtained 2-((1-(2-(4-fluorophenyl)-acetyl)piperidin-4-yl)carbonyl) cyclohexanone in ethanol was added hydrazine hydrate (0.2 g) and the mixture was refluxed for 1 hour. The solvent was evaporated under reduced pressure, and the obtained residue was subjected to silica gel column chromatography to give 3-(1-(2-(4-fluorophenyl)acetyl)piperidin-4-yl)-4,5,6,7-tetrahydro-2H-indazole.

$^1$H-NMR(CDCl$_3$)δ: 1.45–1.98(8H,m), 2.39(2H,t,J=6 Hz), 2.59(2H,t,J=6 Hz), 2.63–2.91(2H,m), 3.14(2H,dt,J=3.13 Hz), 3.72(2H,s), 3.94(1H,d,J=14 Hz), 4.78(1H,d,J=14 Hz), 6.93–7.06(2H,m), 7.18–7.30(2H,m)

To a solution of the obtained 3-(1-(2-(4-fluorophenyl) acetyl)piperidin-4-yl)-4,5,6,7-tetrahydro-2H-indazole in tetrahydrofuran was added lithium aluminum hydride under ice-cooling with stirring, and the mixture was stirred at room temperature for 1 hour. After the completion of the reaction, the reaction mixture was treated with a mixed solvent of water—tetrahydrofuran and filtered through celite. The filtrate was concentrated under reduced pressure, and the obtained residue was subjected to silica gel column chromatography to give 3-(1-(2-(4-fluorophenyl)ethyl)piperidin-4-yl)-4,5,6,7-tetrahydro-2H-indazole dihydrochloride monohydrate, m.p. 143–145° C.

EXAMPLE 197

Compound A

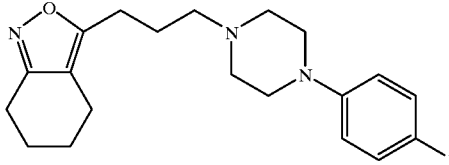

Compound B

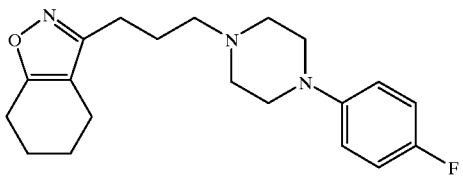

4-Oxo-4-(2-oxocyclohexyl)-n-butyric acid (4.0 g) and 1-(4-fluorophenyl)piperazine (3.6 g) were used instead of 3-(4,5,6,7-tetrahydro-2H-indazol-3-yl)propionic acid obtained in Example 102 and 4-(4-chlorophenyl)piperidine, 7.4 g of 4-(4-fluorophenyl)-1-(4-oxo-4-(2-oxocyclohexyl) butyryl)piperazine was obtained.

This compound (3.6 g) was refluxed under heating for 5 hours in methanol (100 ml) in the presence of hydroxylamine hydrochloride (3.2 g) and triethylamine (6.3 ml). After the completion of the reaction, the solvent was evaporated under reduced pressure and an aqueous potassium carbonate solution was added to the residue. The mixture was extracted with chloroform and the extract was dried over magnesium sulfate. The solvent was evaporated under reduced pressure to give 3.5 g of an oily substance. This compound and triethylamine (5.2 ml) were dissolved in ethylene dichloride (50 ml), and methanesulfonyl chloride (1.4 ml) was dropwise added under ice-cooling. After the completion of the reaction, the solvent was evaporated under reduced pressure, and an aqueous potassium carbonate solution was added to the residue. The mixture was extracted with chloroform and the extract was dried over magnesium sulfate. The solvent was evaporated under reduced pressure to give 3.7 g of an oily substance.

This compound was dissolved in tetrahydrofuran (50 ml), and lithium aluminum hydride (1.5 g) was added under ice-cooling. After the completion of the reaction, a mixed solution of tetrahydrofuran—water, then ethyl acetate, and magnesium sulfate were added, and the mixture was filtered through celite. The solvent was evaporated under reduced pressure. The obtained residue was subjected to silica gel column chromatography to give 3-(3-(4-(4-fluorophenyl) piperazin-1-yl)propyl)-4,5,6,7-tetrahydrobenzo [c]isoxazole (component eluted first: compound A), and 3-(3-(4-(4-fluorophenyl)piperazin-1-yl)propyl)-4,5,6,7-tetrahydrobenzo[d]isoxazole (component eluted later: compound B) from the eluate of chloroform:methanol=50:1.

Compound; $^1$H-NMR(CDCl$_3$)δ: 1.67–1.82(4H,m), 1.84–1.95(2H,m), 2.35–2.46(4H,m), 2.56–2.60(4H,m), 2.69–2.75(4H,m), 3.09–3.13(4H,m), 6.83–7.00(4H,m)

Compound B; $^1$H-NMR(CDCl$_3$)δ: 1.70–1.96(6H,m), 2.34–2.52(4H,m), 2.57–2.75(8H,m), 3.11–3.14(4H,m), 6.84–6.99(4H,m)

EXAMPLE 198

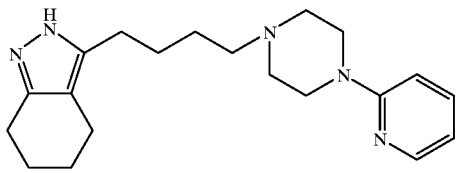

In the same manner as in Example 102 except that 4-(4,5,6,7-tetrahydro-2H-indazol-3-yl)-n-butyric acid obtained in Starting Material Synthesis Example 3 and 1-(2-pyridyl)piperazine were used instead of 3-(4,5,6,7-tetrahydro- 2H-indazol-3-yl)propionic acid obtained in Starting Material Synthesis Example 1 and 4-(4chlorophenyl)piperidine, 3-(4-(4-(2-pyridyl)piperazin-1-yl)butyl)-4,5,6,7-tetrahydro-2H-indazole was obtained.

$^1$H-NMR(CDCl$_3$)δ: 1.55–1.80(8H,m), 2.34–2.44(4H,m), 2.52–2.64(8H,m), 3.53–3.57(4H,m), 6.58–6.65(2H,m), 7.43–7.49(1H,m), 8.18(1H,dd,J=2.6 Hz)

EXAMPLE 199

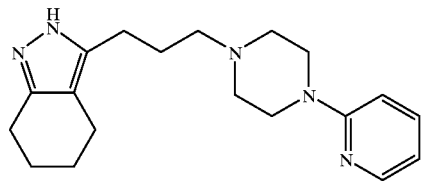

In the same manner as in Example 102 except that 1-(2-pyridyl)piperazine was used instead of 4-(4-chlorophenyl)piperidine, 3-(3-(4-(2-pyridyl)piperazin-1-yl)propyl)-4,5,6,7-tetrahydro-2H-indazole was obtained.

$^1$H-NMR(CDCl$_3$)δ: 1.66–1.92(6H,m), 2.40–2.48(4H,m), 2.56–2.72(8H,m), 3.55–3.59(4H,m), 6.59–6.65(2H,m), 7.43–7.50(1H,m), 8.18(1H,dd,J=2.4 Hz)

EXAMPLE 200

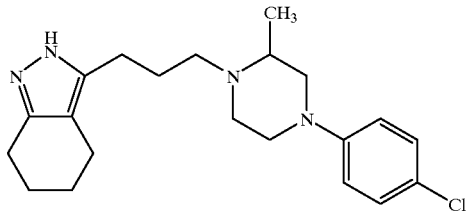

In the same manner as in Example 102 except that 1-(4chlorophenyl)-3-methylpiperazine was used instead of 4-(4-chlorophenyl)piperidine, 3-(3-(4-(4-chlorophenyl)-2-methylpiperazin-1-yl)propyl)-4,5,6,7-tetrahydro-2H-indazole was obtained.

$^1$H-NMR(CDCl$_3$)δ: 1.01(3H,d,J=6 Hz), 1.68–1.94(6H, m), 2.30–2.56(6H,m), 2.58–2.73(5H,m), 2.79–2.89(1H,m), 3.10–3.23(2H,m), 3.78–3.88(1H,m), 6.83(2H,d,J=9 Hz), 7.19(2H,d,J=9 Hz)

EXAMPLE 201

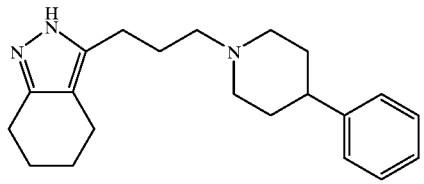

In the same manner as in Example 102 except that 4-phenylpiperadine was used instead of 4-(4-chlorophenyl)piperidine, 3-(3-(4-phenylpiperidin-1-yl)propyl)-4,5,6,7-tetrahydro-2H-indazole was obtained.

$^1$H-NMR(CDCl$_3$)δ: 1.69–1.92(10H,m), 1.98–2.13(2H, m), 2.40–2.52(5H,m), 2.61–2.71(4H,m), 3.02–3.24(2H,m), 7.14–7.34(5H,m)

EXAMPLE 202

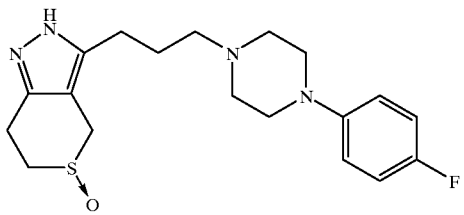

3-(3-(4-(4-Fluorophenyl)piperazin-1-yl)propyl)-2,4,6,7-tetrahydro-thiopyrano[4,3-c]pyrazole (0.5 g) obtained in Example 138 was dissolved in formic acid (5 ml) and 30% hydrogen peroxide (0.27 ml) was dropwise added under ice-cooling, and the mixture was stirred for 30 minutes at not more than 5° C. The reaction mixture was poured into ice water, made alkaline with potassium carbonate and extracted with ethyl acetate. After drying over magnesium sulfate, the solution was concentrated and recrystallized from isopropyl alcohol:isopropyl ether (1:2) to give 3-(3-(4-(4-fluorophenyl)piperazin-1-yl)propyl)-2,4,6,7-tetrahydrothiopyrano[4,3-c]pyrazole 5-oxide, m.p. 140–142° C.

EXAMPLE 203

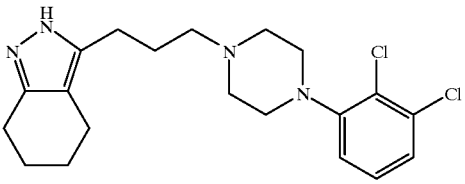

In the same manner as in Example 102 except that 1-(2,3-dichlorophenyl)piperazine was used instead of 4-(4-chlorophenyl)piperidine, 3-(3-(4-(2,3-dichlorophenyl)piperazin-1-yl)propyl)-4,5,6,7-tetrahydro-2H-indazole was obtained.

$^1$H-NMR(CDCl$_3$)δ: 1.68–1.95(6H,m), 2.43(2H,t,J=6 Hz), 2.51(2H,t,J=7 Hz), 2.56–2.77(8H,m), 3.02–3.16(4H,m), 6.92–6.99(1H,m), 7.08–7.17(2H,m)

EXAMPLE 204

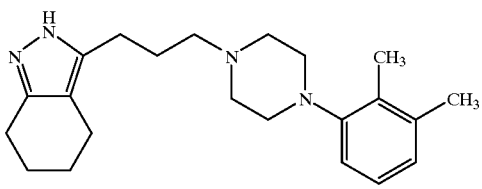

In the same manner as in Example 102 except that 1-(2,3-dimethylphenyl)piperazine was used instead of 4-(4-chlorophenyl)piperidine, 4,5,6,7-tetrahydro-3-(3-(4-(2,3-dimethylphenyl)piperazin-1-yl)propyl)-2H-indazole was obtained.

$^1$H-NMR(CDCl$_3$)δ: 1.68–1.92(6H,m), 2.21(3H,s), 2.26 (3H,s), 2.43(2H,t,J=6 Hz), 2.49(2H,t,J=7 Hz), 2.55–2.76 (8H,m), 2.89–3.02(4H,m), 6.99(1H,d,J=7 Hz), 6.93(1H,d, J=9 Hz), 7.07(1H,dd,J=9.7 Hz)

EXAMPLE 205

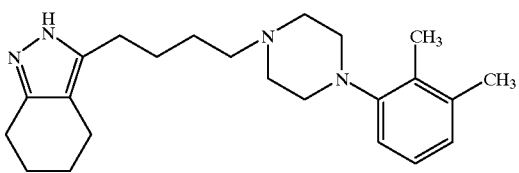

In the same manner as in Example 133 except that-1-(2,3-dimethyl-phenyl)piperazine was used instead of 1-(4-fluorophenyl)piperazine, 3-(4-(4-(2,3-dimethylphenyl)piperazin-1-yl)butyl)-4,5,6,7-tetrahydro-2H-indazole was obtained.

$^1$H-NMR(CDCl$_3$)δ: 1.56–1.83(8H,m), 2.26(3H,s), 2.34 (3H,s), 2.41–2.46(4H,m), 2.57–2.64( 8H,m), 2.90–2.94(4H, m), 6.90(2H,t,J=8 Hz), 7.07(1H,t,J=8 Hz)

EXAMPLE 206

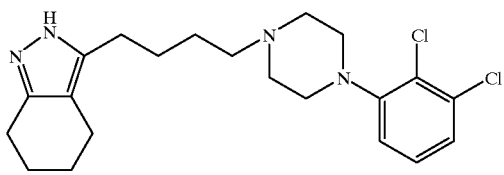

In the same manner as in Example 133 except that 1-(2,3-dichloro-phenyl)piperazine was used instead of 1-(4-fluorophenyl)piperazine, 3-(4-(4(2,3-dichlorophenyl) piperazin-1-yl)butyl)-4,5,6,7-tetrahydro-2H-indazole was obtained.

$^1$H-NMR(CDCl$_3$)δ: 1.53–1.88(8H,m), 2.41–2.47(4H,m), 2.57–2.65(8H,m), 3.07–3.10(4H,m), 6.96(1H,dd,J=3.6 Hz), 7.13–7.15(2H,m)

FORMULATION EXAMPLE 1

The inventive compound (0.5 part), lactose (25 parts), crystalline cellulose (35 parts) and corn starch (3 parts) were thoroughly admixed and kneaded well with a binder prepared from corn starch (2 parts). The kneaded product was passed through a 16 mesh sieve, dried in an oven at 50° C. and passed through a 24 mesh sieve. The kneaded powder thus obtained, corn starch (8 parts), crystalline cellulose (11 parts) and talc (9 parts) were thoroughly admixed and compressed to give tablets containing 0.5 mg of an active ingredient per tablet.

FORMULATION EXAMPLE 2

The inventive compound (1.0 mg) and sodium chloride (9.0 mg) are dissolved in injectable water, and the solution is filtered to remove pyrogen. The filtrate is aseptically charged in ampoules and sterilized, which is followed by melt-sealing of the ampoules to give injections containing 1.0 mg of an active ingredient.

The superior pharmacological activity of the compound of the formula (I) was evaluated by the following series of receptor binding tests, anti-methamphetamine action, catalepsy induction and suppressive effect on neurotoxicity by MK-801.

EXPERIMENTAL EXAMPLE 1

Affinity for D$_4$ Receptor; $^3$H-spiperone Binding

The D$_4$ receptor expression cell membrane specimen and $^3$H-spiperone were incubated at 27° C. for 2 hours in the presence of a test compound. Immediately after the completion of the reaction, the reaction mixture was filtered through a Whatman GF/B filter (trademark) by suction and the radioactivity on the filter was determined on a liquid scintillation counter. The amount of non-specific binding was determined in the presence of 10 μM haloperidol. The concentration of the test compound necessary for inhibiting by 50% (IC$_{50}$) was calculated from nonlinear regression curve, based on which the inhibition constant (Ki value) was determined.

EXPERIMENTAL EXAMPLE 2

Affinity for D$_2$ Receptor; $^3$H-spiperone Binding

Preparation of crude synaptic membrane and binding test followed the method of I. Creese et al., European Journal of Pharmacology, vol. 46, p. 377 (1977). The crude synaptic membrane was prepared from the cryopreserved striate body from rats and the membrane sample and $^3$H-spiperone were reacted at 37° C. for 20 minutes in the presence of a test compound. Immediately after the completion of the reaction, the reaction mixture was filtered through a Whatman GF/B filter (trademark) by suction and the radioactivity on the filter was determined on a liquid scintillation counter. The amount of non-specific binding was determined in the presence of 100 μM(±)-sulphide. The concentration of the test compound necessary for 50% inhibiting (IC$_{50}$) was calculated from nonlinear regression curve, based on which the inhibition constant (Ki value) was determined.

As a result of Experimental Examples 1 and 2, the inventive compound showed a Ki value for D$_4$ receptor of 0.01–10 nM, whereas it was not less than 10 nM for D$_2$ receptor. Therefore, the inventive compound was confirmed to have a stronger affinity for D$_4$ receptor than for D$_2$ receptor. In contrast, Dapiprazole barely showed affinity for D$_4$ receptor or D$_2$ receptor.

EXPERIMENTAL EXAMPLE 3

Affinity for 5-HT$_2$ Receptor

A specific serotonin 2 (5-HT$_2$) receptor binding test followed the method of Mol. Pharmacol., vol. 21, p. 301 (1981).

A crude synaptosome fraction was separated from hippocampus of 9–10 week-old Wistar rats, and suspended in 50 mM Tris-HCl buffer (pH 7.7) for the experiment. The test compound in several concentrations and tritiated ketanserin (final concentration 0.2 nM) were added to the synaptosome suspension, and each mixture was incubated at 37° C. for 20 minutes. After the incubation, the mixture was filtered with suction through Whatman GF/B (trademark) glass filter. The filter was washed with 50 nM Tris-HCl buffer (pH 7.7), and the radioactivity of the filter was measured by a liquid scintillation counter. Non-specific binding was determined in the presence of $10^{-5}$ M mianserin. The concentration necessary for 50% inhibition ($IC_{50}$) was determined on a graph, and inhibition constant (Ki value) was calculated.

As a result, the inventive compound showed strong affinity of 0.01–50 nM for $5\text{-}HT_2$ Receptor.

EXPERIMENTAL EXAMPLE 4

Evaluation of Mouse Anti-methamphetamine Action (major effect)

Male ddY mice (20–30 g, 4 weeks of age, 15 mice per group) were used for the experiment. A test compound was orally administered to the mice, and one hour later, an aqueous solution of methamphetamine (DAINIPPON PHARMACEUTICAL CO., LTD., 1 mg/kg) in physiological saline was subcutaneously administered. Immediately thereafter, the mice were placed in a measurement apparatus equipped with a pair of infrared beams and having an inner size of 25×15×14 (height) cm. The number of crossings through the infrared beams in 30 minutes from 10 minutes to 40 minutes after initiation of observation was used as an index to show promoted motion induced by methamphetamine, and the suppressive action of the $ED_{50}$ value of the test compound was calculated.

As a result, the inventive compound showed a strong activity as expressed by the $ED_{50}$ value of not more than 1.0 mg/kg (p.o.).

EXPERIMENTAL EXAMPLE 5

Evaluation of Catalepsy Induction (side effects)

Male ddY mice (20–30 g, 4 weeks of age, 8 per group) were used for the test. A test compound was administered to the mice, and 1, 3, 5 and 7 hours later, the time (catalepsy time) was measured for up to 30 seconds maximum, during which time the forelimbs were placed on a bar fixed at a height of 4 cm in the horizontal direction, and the body posture was kept at an angle of about 45 degrees. The strength of the catalepsy induction of the test compound was evaluated by adding the catalepsy times at 4 determination points at each dose (total time being a sum value) and calculating $ED_{10s}$ by regression to the dose that made the average time 10 seconds.

As a result, $ED_{10s}$ of the inventive compound was not less than 20 mg/kg, indicating weak catalepsy induction.

EXPERIMENTAL EXAMPLE 6

Suppressive Effect on Neurotoxicity by MK-801

Female SD rats (200–300 g, 9–12 weeks of age) were used for the test. An aqueous solution of the test compound (0.1 ml/kg) was intraperitoneally administered and an aqueous solution of (+)-MK-801 (0.5 mg/kg, 0.1 ml/kg, Research Biochemicals International, Natick, Mass., USA) was subcutaneously administered 15 minutes later. After 4 hours from the administration of MK-80 1, the rats were anesthetized with pentobarbital. An injection needle was inserted into the left ventricle of the rats and left auricle was opened. After exsanguination by perfusion with physiological saline (ca. 100 ml), the rats were fixed under perfusion with 4% paraformaldehyde ·1.5% glutalaldehyde ·0.1 M phosphate buffer (ca. 400–500 ml). The head was opened and the brain was removed. A part including posterior cingulate convolution was cut out and placed in said fixative for postfixation. Upon paraffin embedding, a thin section (3 μm) was prepared and stained with hematoxylin and eosin. After dehydration and sealing, the slide was observed with an optical microscope.

As a result of the test, the inventive compound was found to suppress neurotoxicity (vacuolation of cells) of posterior cingulate convolution, which is observed on administration of an NMDA receptor antagonistic drug MK-801. The test results reveal that the inventive compound improves degradation of NMDA receptor function.

EXPERIMENTAL EXAMPLE 7

Acute Toxicity

The inventive compound (100 mg/kg) was orally administered to 4 female SD rats (5 weeks of age) but no death was observed.

The inventive fused heterocyclic compound, an optical isomer thereof and a pharmaceutically acceptable salt thereof show a strong blocking action on $D_4$ receptor and $5\text{-}HT_2$ receptor, as well as blockage of NMDA receptor hyofunction. In addition, the inventive compound possesses a pharmacological action, such as anti-methamphetamine action, that is necessary as an antipsychotic agent, as well as a strong suppressive action on neurotoxicity induced by MK-801. On the other hand, catalepsy induction in mice, which is an index of extrapyramidal side effects, was found to be extremely weak. The results indicate greater dissociation of the major effect from the side effects of the inventive compound.

From the foregoing results, it is clear that the inventive compounds can make useful antipsychotic agents effective against not only positive symptoms centering on hallucination and delusion characteristic of the acute stage of schizophrenia, but also negative symptoms of apathy, abulia and autism. They are expected to be highly safe antipsychotic agents associated with less side effects, such as extrapyramidal symptoms and endocrine disturbance, which are observed when conventional antipsychotic agents having $D_2$ receptor blocking action are administered. Thus, the inventive compounds can be used as therapeutic agents for the diseases such as schizophrenia.

What is claimed is:

1. A compound of the formula (I)

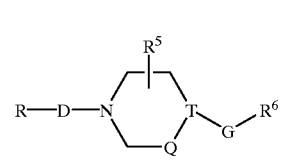

(I)

wherein
R is a group having the following formula (3),

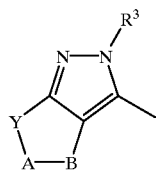

(3)

wherein
Y is a linear or branched $C_1$–$C_4$ alkylene optionally having a substituent $R^{1a}$ at an optional position, wherein $R^{1a}$ is alkyl, hydroxy, alkoxy, amino or alkylamino,
A is void, or an oxygen atom, a sulfur atom, SO, $SO_2$ or N—$R^7$ wherein $R^7$ is hydrogen, alkyl, arylalkyl or acyl,
B is a linear or branched $C_1$–$C_4$ alkylene optionally having a substituent $R^{1b}$ at an optional position, wherein $R^{1b}$ is alkyl, hydroxy, alkoxy, amino or alkylamino, and
$R^3$ is a hydrogen, an alkyl, an acyl or an aryl;
D is void, or a linear or branched alkylene having 1 to 8 carbon atoms;
Q—T is $CH_2$—N;
G is void, or a linear or branched alkylene having 1 to 8 carbon atoms or a carbonyl;
$R^5$ is a hydrogen or an alkyl; and
$R^6$ is an optionally substituted aryl, an optionally substituted heteroaryl or an optionally substituted fused heteroaryl, the optional substituent being selected from the group consisting of halogen, haloalkyl, alkyl, alkoxy, hydroxy, nitro, amino, methylamino and dimethylamino,
an optical isomer thereof or a pharmaceutically acceptable salt thereof.

2. The compound of claim 1, wherein, in the formula (I),
R is a group having the formula (3),
wherein
Y is a linear or branched $C_1$–$C_4$ alkylene optionally having a substituent $R^{1a}$ at an optional position wherein $R^{1a}$ is alkyl,
A is void, or an oxygen atom, a sulfur atom or N—$R^7$ wherein $R^7$ is hydrogen, alkyl, arylalkyl or acyl,
B is a linear or branched $C_1$–$C_4$ alkylene optionally having a substituent $R^{1b}$ at an optional position, wherein $R^{1b}$ is alkyl, and
$R^3$ is a hydrogen, an alkyl, an acyl or an aryl;
D is void, or a linear or branched alkylene having 1 to 8 carbon atoms;
Q—T is $CH_2$—N;
G is void;
$R^5$ is a hydrogen or an alkyl; and
$R^6$ is an optionally substituted aryl, an optionally substituted heteroaryl or an optionally substituted fused heteroaryl,
an optical isomer thereof or a pharmaceutically acceptable salt thereof.

3. The compound of claim 1, wherein, in the formula (I),
R is a group having the formula (3),
wherein
Y is a linear alkylene having 1 to 4 carbon atoms,
A is void, or an oxygen atom or N—$R^7$ wherein $R^7$ is hydrogen or acyl,
B is a linear or branched alkylene having 1 to 4 carbon atoms, and
$R^3$ is a hydrogen, an alkyl having 1 to 4 carbon atoms or an acyl;
D is void, or a linear or branched alkylene having 1 to 8 carbon atoms;
Q—T is $CH_2$—N;
G is void;
$R^5$ is a hydrogen or an alkyl having 1 to 4 carbon atoms; and
$R^6$ is an optionally substituted aryl, an optionally substituted heteroaryl or an optionally substituted fused heteroaryl,
an optical isomer thereof or a pharmaceutically acceptable salt thereof.

4. The compound of claim 1, wherein, in the formula (I),
R is a group having the formula (3),
wherein
Y is an ethylene,
A is void, or an oxygen atom or N—$R^7$ wherein $R^7$ is hydrogen or acyl,
B is a linear or branched alkylene having 1 to 3 carbon atoms, and
$R^3$ is a hydrogen or an alkyl having 1 to 4 carbon atoms;
D is void, or a linear or branched alkylene having 1 to 8 carbon atoms;
Q—T is $CH_2$—N;
G is void;
$R^5$ is a hydrogen or an alkyl having 1 to 4 carbon atoms; and
$R^6$ is an optionally substituted aryl, an optionally substituted heteroaryl or an optionally substituted fused heteroaryl,
an optical isomer thereof or a pharmaceutically acceptable salt thereof.

5. The compound of claim 1, wherein, in the formula (I),
R is a group having the formula (3),
wherein
Y is an ethylene,
A is void, or an oxygen atom or N—$R^7$ wherein $R^7$ is hydrogen or acyl,
B is a linear alkylene having 1 to 3 carbon atoms, and
$R^3$ is a hydrogen or a methyl;
D is a trimethylene;
Q—T is $CH_2$—N;
G is void;
$R^5$ is a hydrogen; and
$R^6$ is an aryl optionally having halogen or alkyl having 1 to 4 carbon atoms,
an optical isomer thereof or a pharmaceutically acceptable salt thereof.

6. The compound of claim 1, which is a member selected from the group consisting of the following compounds:
3-(3-(4-(4-chlorophenyl)piperazin-1-yl)propyl)-4,5,6,7-tetrahydro-2H-indazole,
3-(3-(4-(4-fluorophenyl)piperazin-1-yl)propyl)-4,5,6,7-tetrahydro-2H-indazole,
3-(3-(4-(4-methylphenyl)piperazin-1-yl)propyl)-4,5,6,7-tetrahydro-2H-indazole,
3-(3-(4-phenylpiperazin-1-yl)propyl)-4,5,6,7-tetrahydro-2H-indazole, 3-(3-(4-(4-fluorophenyl)piperazin-1-yl)propyl)-2,4,6,7-tetrahydropyrano[4,3-c]pyrazole, 3-(3-(4-(4-fluorophenyl)piperazin-1-yl)propyl)-4,5,6,7-tetrahydro-2H-pyrazolo[4,3-c]pyridine, and 5-acetyl-3-(3-(4-(4-fluorophenyl)piperazin-1-yl)propyl)-4,5,6,7-tetrahydro-2H-pyrazolo[4,3-c]pyridine, or a pharmaceutically acceptable salt thereof.

7. A pharmaceutical composition comprising the compound of claim 1, an optical isomer thereof or a pharmaceutically acceptable salt thereof, and a pharmaceutically acceptable additive.

8. A method for the treatment of psychosis which comprises administering to a patient in need of same, the compound according to claim 1.

9. The compound of claim 1, which is 3-(3-(4-(4-fluorophenyl)piperazin-1-yl)propyl)-4,5,6,7-tetrahydro-2H-indazole.

* * * * *

UNITED STATES PATENT AND TRADEMARK OFFICE
CERTIFICATE OF CORRECTION

PATENT NO. : 6,187,774 B1
DATED : February 13, 2001
INVENTOR(S) : Hiroshi Tanaka et al.

It is certified that error appears in the above-identified patent and that said Letters Patent is hereby corrected as shown below:

Title page,
Item [22], should be rewritten as follows:
-- [22] PCT Filed: Mar. 3, 1997

Signed and Sealed this

Twenty-sixth Day of March, 2002

*Attest:*

JAMES E. ROGAN
*Attesting Officer*     *Director of the United States Patent and Trademark Office*